(12) United States Patent
Granucci et al.

(10) Patent No.: US 7,442,547 B2
(45) Date of Patent: Oct. 28, 2008

(54) DENDRITIC CELLS AND THE USES THEREOF IN SCREENING CELLULAR TARGETS AND POTENTIAL DRUGS

(75) Inventors: Francesca Granucci, Merate (IT); Paola Ricciardi-Castagnoli, Segrate (IT)

(73) Assignee: Sekmed, S.R.L., Milan (IT)

( * ) Notice: Subject to any disclaimer, the term of this patent is extended or adjusted under 35 U.S.C. 154(b) by 280 days.

(21) Appl. No.: 10/210,141

(22) Filed: Jul. 31, 2002

(65) Prior Publication Data

US 2003/0152550 A1 Aug. 14, 2003

Related U.S. Application Data

(60) Provisional application No. 60/309,102, filed on Jul. 31, 2001.

(51) Int. Cl.
*C12N 5/00* (2006.01)
*C12N 5/02* (2006.01)
*C12N 5/06* (2006.01)

(52) U.S. Cl. ................................ 435/375; 435/355
(58) Field of Classification Search ................ None
See application file for complete search history.

(56) References Cited

U.S. PATENT DOCUMENTS

2003/0086900 A1* 5/2003 Low et al. ................. 424/85.2

OTHER PUBLICATIONS

Andrews et al., Infection of dendritic cells by murine cytomegalovirus induces functional paralysis, 2001, vol. 2 :1077-1084.*
Rescigno et al., "Coordinated events during bacteria-induced DC maturation", *Immunology Today,* Elsevier Publications, Cambridge, GB, vol. 20, No. 5, May 1999 pp. 200-203.
Rescigno et al., "Molecular events of bacterial-induced maturation of dendritic cells", *Journal of Clinical Immunology,* vol. 20, No. 3, May 2000, pp. 161-166.

Shimizu et al., "Systemic Administration of Interleukin 2 Enhances The Therapeutic Efficacy of Dendritic Cell-Based Tumor Vaccines", *Proc. Nat'l. Acad. Sci.,* Washington, U.S., vol. 96, Mar. 1999 pp. 268-2273.
Kronin et al., "Regulation of T Cell Cytokine Production by Dendritic Cells", *Immunology and Cell Biology,* vol. 78, No. 3, Jun. 2000 pp. 214-223.
Granucci et al., "Inducible IL-2 Production by Dendritic Cells Revealed by Global Gene Expression Analysis", *Nature,* Immunology, (Sep. 2001), vol. 2, No. 9, pp. 882-888.
Granucci et al., "IL-2 Mediates Adjuvant Effect of Dendritic Cells", *Trends In Immunology,* Elsevier, Cambridge, GB, vol. 23, No. 4, Apr. 2002, pp. 169-171.
Ricciardi-Castagnoli et al., "Opinion: Interpretation of the Complexity of Innate Immune Responses by Functional Genomics", *Nature Reviews,* Immunology, England Nov. 2002), vol. 2, No. 11, pp. 881-889.

* cited by examiner

*Primary Examiner*—G. R. Ewoldt
*Assistant Examiner*—Amy Juedes
(74) *Attorney, Agent, or Firm*—DLA Piper LLP (US)

(57) ABSTRACT

The present invention is based on the discovery that in response to different stimuli, dendritic cells initiate various immune responses by producing different transcription profiles, e.g., IL-2 production by dendritic cells in response to a microbial stimulus. The present invention provides methods of making libraries of gene expression profiles and libraries made thereof corresponding to dendritic cell maturation in response to a microbial stimulation. The present invention provides methods for activating lymphocytes or immune responses and methods for producing Il-2 in dendritic cells or preparing dendritic cells for cell-based therapy. The present invention also provides methods and systems for screening agents affecting dendritic cell maturation. In addition, it is the discovery of the present invention that dendritic cells are targets for immunosuppressive virus infections. Accordingly, the present invention provides methods for treating immunosuppressive virus infections or immunosuppression associated with immunosuppressive virus infection. The present invention also provides methods for screening candidate therapeutic agents suitable for treating immunosuppressive virus infection using dendritic cell system.

5 Claims, 28 Drawing Sheets

**Cytoskeleton/Integrins/
Extracellular Matrix**

0h 4h 6h 12h 18h 24h 48h

Myosin I
E-cadherin
Rabkinesin-6
Integrin β7
Tubulin Mα4
Gelsolin
TubulinMα3
Vav
Tubulin Mβ5
Vav-T
WASp
Collagen XVII
Fibronectin
LAMB 3
Vav2
Desmin
R-cadherin
Tenascin
Laminin B2
P-selectin
Adseverin
Integrin α5
A-X Actin
ICAM-1
LFA-1
Integrin associated
COL4A-1
Fascin
H2-calponin
SPNB-2
Integrin α4
Myosin IIB

**Inflammation/Chemokines/
Cytokines**

Amyloid A
TGFα
Flt3
IL6
MIP-1α
RANTES
IL12p40
MIP-1β
MIP2
IL1 α
IL1RA
TNFα
TGFβ1
C3
IL15
IL10
LT
VEGF
IP-10
MCSF
IL12p35
IL2
GM-CSF
EGF-BP
C1qC
C1qB
C1qα
MCP5
PDGF
LTβ
JE
mvrf186

Apoptosis

Bcl-2
BID
Bcl-X
LICE2
MORT-1
FAF-1
Miap1
Miap2
TRAF2
TNFR2
FAS
TRAF1
ICH3
TDAG8

Increasing expression

Signal Transduction

PKCλ
MEKK4a
Rab3D
VASP
Vav
Vav-T
PKCα
VAMP2
JAK3
Stat4
Stat6
Stat5b
Stat5a
TRAF6
Pim2
MEK
RhoC
MDK2
MEK2
Vav2
PK2
PAC1
Stat1
SEK1
MEP

**Transcription Factors/
DNA Binding Proteins**

GATA1
Krox20
Pmx
Pbx2
Pbx3b
KRAB
CP2
TCF2
NFIL3/E4BP4
Sp4
Cor1
NFκB p105
EF1
A20 Zn-finger
A20 Zn-finger
NF-YC
IKAROS
Myo-D
En1
NFAT1
Zfp92
BFCOL1
ID1
Mfz9
Leucin-zipper TF
Hoxd4

FIG. 15(III)

DENDRITIC CELLS AND THE USES THEREOF IN SCREENING CELLULAR TARGETS AND POTENTIAL DRUGS

CROSS REFERENCE TO RELATED APPLICATIONS

This application claims priority under 35 U.S.C. 119(e) to U.S. Provisional Application No. 60/309,102, filed on Jul. 31, 2001, which is incorporated herein by reference in its entirety.

FIELD OF THE INVENTION

This invention relates generally to the immune system and more specifically to dendritic cell activity in response to various stimuli.

BACKGROUND OF THE INVENTION

The immune system is characterized by the ability to respond to infectious agents without mounting a destructive response against self-tissues. The first line of defense to invading pathogens is represented by the innate immune response that detects and limits the infection. From the innate response, it originates the adaptive immune response, which discriminates among pathogens and gives rise to memory.

Dendritic cells (DC) are extremely versatile professional antigen presenting cells (APCs) involved in the initiation of both innate and adaptive immunity and in the differentiation of regulatory T cells required for the maintenance of self-tolerance. Key functions of DC include uptake and processing of antigens and priming of naive T cells1, functions which are segregated in time. Immature resting DC located in non-lymphoid tissues, such as skin and mucosae, take up antigen. Immature DC are highly fagocitic and continuously internalize soluble and particulate antigens that are processed and presented to T cells. The interaction of immature DC with T cells induces an abortive T cell activation with the induction of T cell anergy or the differentiation of regulatory T cells.

Mature DC loaded with antigens and capable of priming T cells migrate from non-lymphoid tissues to the T cell area of lymph nodes or spleen. Thus, when immature DC come in contact with inflammatory stimuli, they undergo a maturation process that transforms them from phagocytic and migratory cells to non-phagocytic, highly efficient stimulators of naive T cell responses. Mature DC are programmed to undergo apoptotic death in 9-10 days.

Inflammatory and microbial stimuli induce the DC maturation process that concludes 24 hours later. Mature DC express at the cell surface high levels of stable peptide-MHC complexes and costimulatory molecules and are capable of prime naive T cells. During the process of differentiation, DC undergo intermediate maturational stages in which they express, with a strictly defined kinetic, cytokines and cell surface molecules critical for activation and control of, first, innate and, then, adaptive immune responses.

Immature monocyte derived human DC (hMDC) or immature bone marrow-derived mouse DC (mBMDC) can be induced to mature in vitro using many different stimuli, including inflammatory cytokines, bacteria cell products like lipopolysaccharide (LPS) and lipoteichoic acid (LTA), bacterial DNA and double-stranded viral RNA, and live bacteria. This last stimulus represents one of the most potent catalysts of DC terminal differentiation process in the mouse, inducing a rapid and effective DC phenotypic and functional maturation4.

The extent and the type of innate and adaptive responses DC activate depend on the type of stimulus they receive. DC are, actually, able to distinguish different pathogens since they express pattern-recognition receptors (PRRs) that interact with specific microorganism molecular structures called pathogens-associated molecular patterns (PAMPs). These constitutive and conserved microbial structures are absent in host mammalian cells and represent the signature of different microorganisms.

Well-defined PRRs are Toll like receptors (TLRs). The stimulation of different TLRs at the DC surface results in the activation of different signaling pathways and in the induction of different maturation processes that influence the outcome of adaptive immunity. In this sense DC are able to respond in a pathogen-specific way.

The transcription profile, transcriptome, is a major determinant of cellular phenotype and function. Differences in gene expression are indicative of morphological, phenotypical and functional changes induced in a cell by environmental factors and perturbations. Microarrays have been successfully applied to identify genes that discriminate between Th1 and Th2 functions in humans and anergic and activated B cells in mice. Micro-array technology is, thus, a valid approach to investigate possible differences induced in particular cell types by diverse external factors.

Concerning DC, a transcriptional profile of immature and LPS-matured human monocyte-derived DC has been carried out revealing 225 differentially expressed genes in the two situations out of a total of 10,962 genes screened. These genes mainly consisted of chemokines (RANTES, ELC, PARK, MDC and TARC) and chemokine receptors (CCR7), enzymes (such as germinal center kinase-related protein kinase), and IFN-inducible proteins (lipase A, CD52, CD11b, CD23, and glucose 6 phosphatase). Nevertheless a comparison between different stimuli in their efficiency in inducing DC maturation has never been performed.

Immunosuppression represents a common outcome of viral infections. The down-regulation of immune responses imparts the infecting pathogens the opportunity to escape immune surveillance and thus maximizes their chances to survive within their host, to replicate and be transmitted as required. The generalized immunosuppression caused by viral infection is often associated with secondary infections with unrelated viral and/or bacterial pathogens and, as such, represents a serious clinical problem. Immunosuppression may also accompany the onset of tumors, again as a means for tumors to evade immune responses and reduce the chances of being eliminated. Understanding the mechanisms involved in the induction of immunosuppression is therefore a crucial step towards the development of better immunotherapies.

Cytomegalovirus (CMV) is one of three viral pathogens of humans known to induce transient, but profound immunosuppression. Unlike measles and HIV, the mechanisms underlying CMV-induced immunosuppression remain poorly understood despite the availability of a unique animal model. Murine cytomegalovirus (MCMV) infection is widely utilized as a model for human CMV infection. Human CMV (HCMV) causes serious complications in immunocompromised hosts such as newborns, transplant patients and AIDS patients. Since CMV infection is species specific, there are no experimental animal models to study HCMV pathogenesis. However, because of the similarity in structure and biology between HCMV and MCMV, the latter provides a unique model of human disease and importantly it permits the study of in vivo infection of the natural host.

In humans, CMV infection causes morbidity and mortality amongst neonates and immunosuppressed individuals. In immunocompetent hosts however, CMV can establish a persistent infection without causing overt disease. The ability to persist and establish a stable relationship with its host is critical to the survival of CMV and strongly underlies its success at evading host defense mechanisms. Amongst the strategies used by CMV to subvert normal defense mechanisms is the "hijacking" of cellular gene products that play critical roles in antiviral responses.

MCMV is capable of subverting the immune system by multiple mechanisms, including down regulation of MHC-I and II molecules, synthesis of chemokine homologues and production of a viral homologue of cellular MHC-I. Studies with mutant viruses lacking specific viral ORFs have clearly demonstrated the effects of MCMV proteins in the regulation of T cell activity and the inhibition of NK cell responses. Studies in murine models have also helped defining the role of specific cellular subsets, with monocytes and macrophages having been shown to be important in viral dissemination and pathogenicity. Interestingly, recent studies have shown that HCMV infects monocyte derived dendritic cells (DC). Importantly, however, there are no reports on the role of DC in MCMV infection, this being the only system that allows the analysis of the biological significance of DC infection in vivo.

There is a need in the art to develop methods and compositions useful for regulating DC, especially in association with DC related immune responses.

SUMMARY OF THE INVENTION

The present invention is based, in part, on the discovery that in response to different stimuli, dendritic cells initiate various immune responses by producing different transcription profiles, e.g., IL-2 production in dendritic cells in response to a microbial stimulus. Accordingly the present invention provides methods of making libraries of gene expression profiles and libraries made thereof corresponding to dendritic cell maturation in response to microbial stimuli. In addition, the present invention provides methods for activating lymphocytes or immune responses and methods for producing Il-2 in dendritic cells or preparing dendritic cells for cell-based therapy. The present invention also provides methods and systems for screening agents affecting dendritic cell maturation.

In addition, it is the discovery of the present invention that dendritic cells are targeted by immunosuppressive virus infections, e.g., cytomegalovirus (CMV) or HIV infection. Accordingly, the present invention provides methods for treating immunosuppressive virus infection, e.g., CMV or HIV infection or immunosuppression associated with immunosuppressive virus infections. The present invention also provides methods for screening candidate therapeutic agents suitable for treating immunosuppressive virus infections.

In one embodiment, the present invention provides a method for activating lymphocytes. The method includes contacting lymphocytes with IL-2 in the presence of dendritic cells, whereby the lymphocytes are activated.

In another embodiment, the present invention provides a method of activating an immune response in a subject contacted by a dendritic cell stimulus. The method includes administering to the subject an effective amount of IL-2, which activates the immune response in combination with dendritic cells stimulated by the stimulus.

In yet another embodiment, the present invention provides a method of inducing IL-2 production in a dendritic cell. The method includes contacting the dendritic cell with an agent activating a toll like receptor of the dendritic cell.

In still another embodiment, the present invention provides a method of making a dendritic cell for cell-based therapy. The method includes contacting the dendritic cell with an agent activating a toll like receptor of the dendritic cell, which induces IL-2 production of the dendritic cell.

In another embodiment, the present invention provides a method of screening an agent for affecting dendritic cell maturation. The method includes incubating in the presence and absence of a test agent, a microbial stimulus and immature dendritic cells, detecting IL-2 expression in the dendritic cells in the presence and absence of the test agent. An increase or decrease in the amount of IL-2 expression caused by the test agent is indicative of an agent affecting dendritic cell maturation.

In another embodiment, the present invention provides an assay system useful for testing an agent's ability to affect dendritic cell maturation. The system includes a container containing a test agent, a microbial stimulus, and immature dendritic cells and allows the detection of IL-2 expression of the dendritic cell.

In yet another embodiment, the present invention provides a method of making a library of a gene expression profile for dendritic cell maturation corresponding to a microbial stimulation. The method includes incubating immature dendritic cells with a microbial stimulus, identifying genes in the dendritic cells that have changed their expression levels due to the microbial stimulus, and generating a gene expression profile for the microbial stimulation which includes one or more genes that change their expression in the dendritic cells in the presence of the microbial stimulus.

In another embodiment, the present invention provides a method of treating an immunosuppression associated with an immunosuppressive virus infection in a subject. The method includes administering to a subject in need of such treatment an effective amount of IL-2 and an activator of dendritic cell.

In yet another embodiment, the present invention provides a method of treating an immunosuppressive virus infection. The method includes administering to a subject in need of such treatment an effective amount of IL-2 and an activator of dendritic cell.

In still another embodiment, the present invention provides a method of screening a candidate therapeutic agent for treating immunosuppressive virus infection. The method includes incubating in the presence and absence of a test agent, an immunosuppressive virus associated with the immunosuppressive virus infection and dendritic cells and determining the level of an activity specific for dendritic cell activation. An increase of the level of the activity in the dendritic cells caused by the test agent is indicative of a candidate therapeutic agent for treating immunosuppressive virus infection.

BRIEF DESCRIPTION OF THE FIGURES

FIG. 1a shows that DC were incubated with DH5α E. coli at a multiplicity of infection (MOI) 10 for 1.5 h and the activation was tested by measuring surface expression of CD40, B7.2 and MHC class II at the indicated time points. RNA was extracted from synchronized cells. FIG. 1b shows an example of gene expression comparison in duplicate experiments (time 0). FIG. 1c shows gene expression comparison of two different time points (time 0 and time 6). Gene expression levels are indicated by the Average Difference value (AvgDiff). The plot in B compares 3340 genes that were called present in the duplicates. The $R^2$ of duplicate linear regressions for each time point was never lower than 0.9. The plot in C compares gene expression of two different time points (0 and 6 h) excluding genes that were consistently called absent in both the analysis. $R^2$ of comparison analysis linear regressions were usually ranging from 0.7-0.8.

FIG. 2a shows that plot of PC2 coefficients against PC3 coefficients obtained by the PCA method (see Table 1). Results of experiments a and b are shown. FIG. 2b shows hierarchical clusters showing the different types of gene expression profiles obtained using the Xcluster program (Gavin Sherlock, http://genome-www.stanford.edu/~sherlock/cluster.html). A filter was used to consider genes that showed a difference in the level of expression of at least 3 among the maximum and minimum expression value in the kinetic. Genes were first clustered using the Self-Organizing Map (SOM) algorithm and subsequently the hierarchical method was applied to each SOM cluster.

The number of 36 clusters was chosen as the most appropriate after different attempts of clustering: higher numbers resulted in the multiplication of clusters with very similar 22 profiles and lower numbers did not give good correlation coefficients in the hierarchical clusters. In each group the kinetic points (0, 4, 6, 12, 18, 24, 48) are represented from left to right. The label in the upper left corner of each box identifies the cluster and the number in the upper right corner indicates how many genes are present in each cluster.

FIG. 3 shows transcription response of DC to bacteria. An example of 130 genes is shown. Genes are grouped according to their most likely function deduced by information available in public databases and in the literature.

Figure 4:
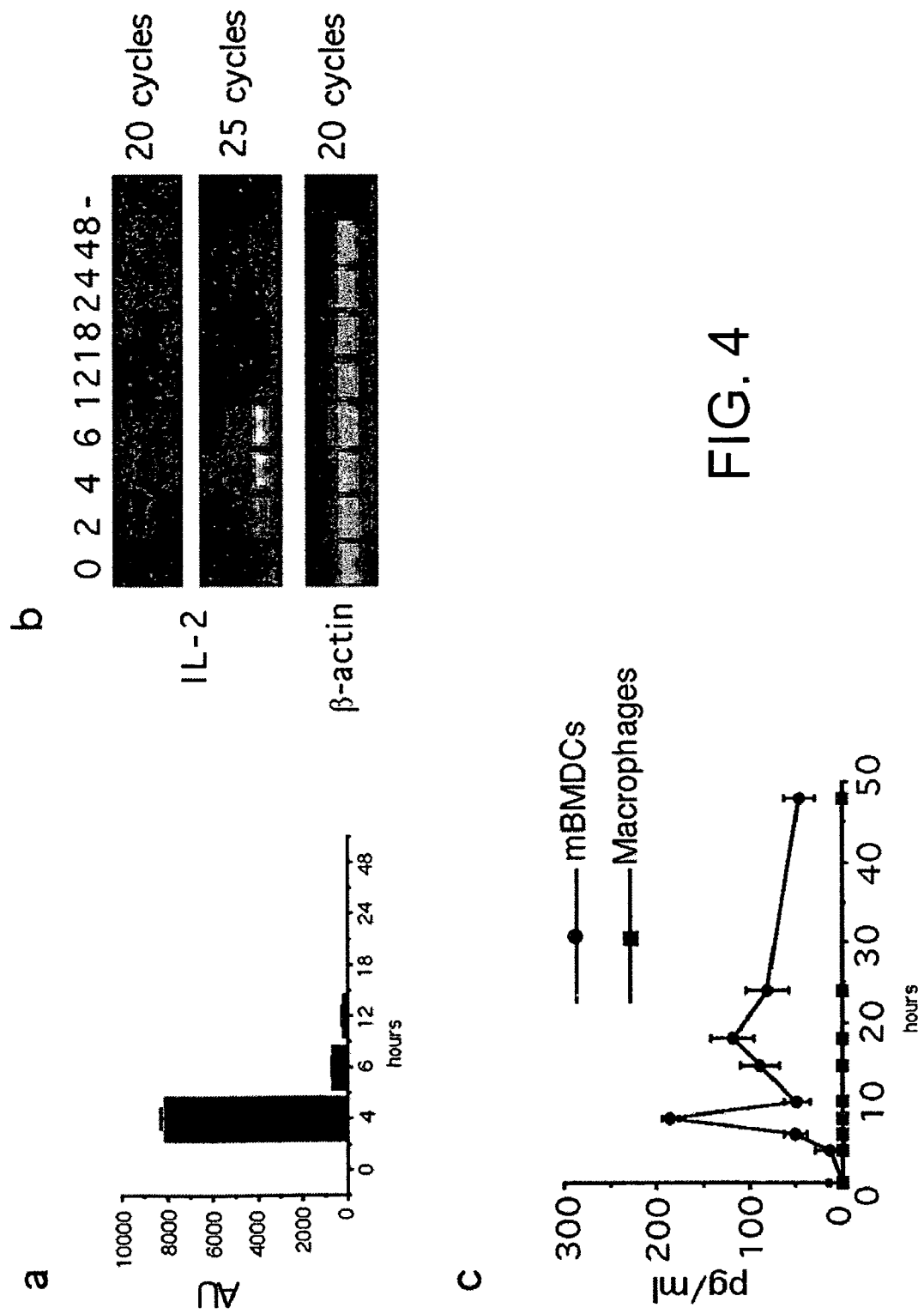

FIGS. 4a to 4c show IL-2 expression by DC. FIG. 4a shows IL-2 mRNA levels in D1 cells after activation with bacteria. Values represent mean average differences (AvgDiff) and standard deviations calculated from 4 probes distributed on 4 different chips. FIG. 4b shows semi-quantitative PCR showing IL-2 expression in mBMDC after bacteria stimulation at the indicated time points. mRNA was obtained from mBMDC. Double stranded cDNA was transcribed from mRNA, purified and quantified. 40 μg of cDNA were used for each sample in PCR reactions. FIG. 4c shows quantification of the amount of IL-2 present in the supernatant of bacteria-activated DC and macrophages. IL-2 was measured in the supernatants by ELISA at the indicated time points. The experiment was repeated 4 times with similar results.

Figure 5A:
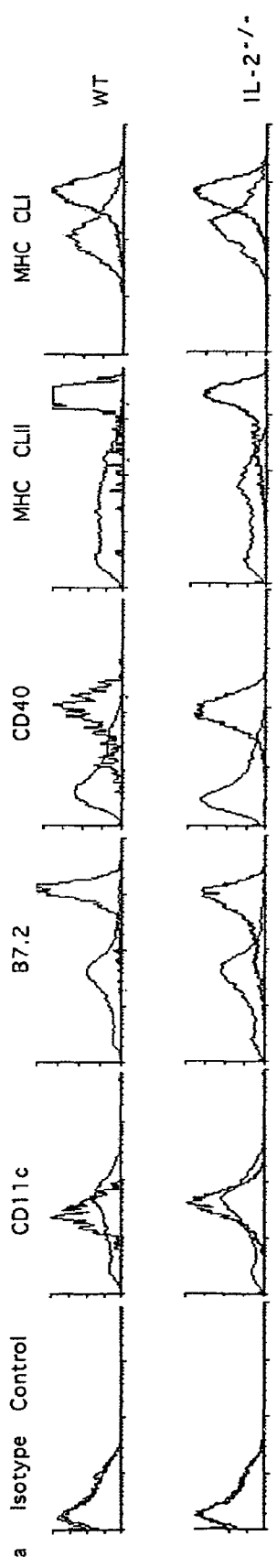
Figure 5B:
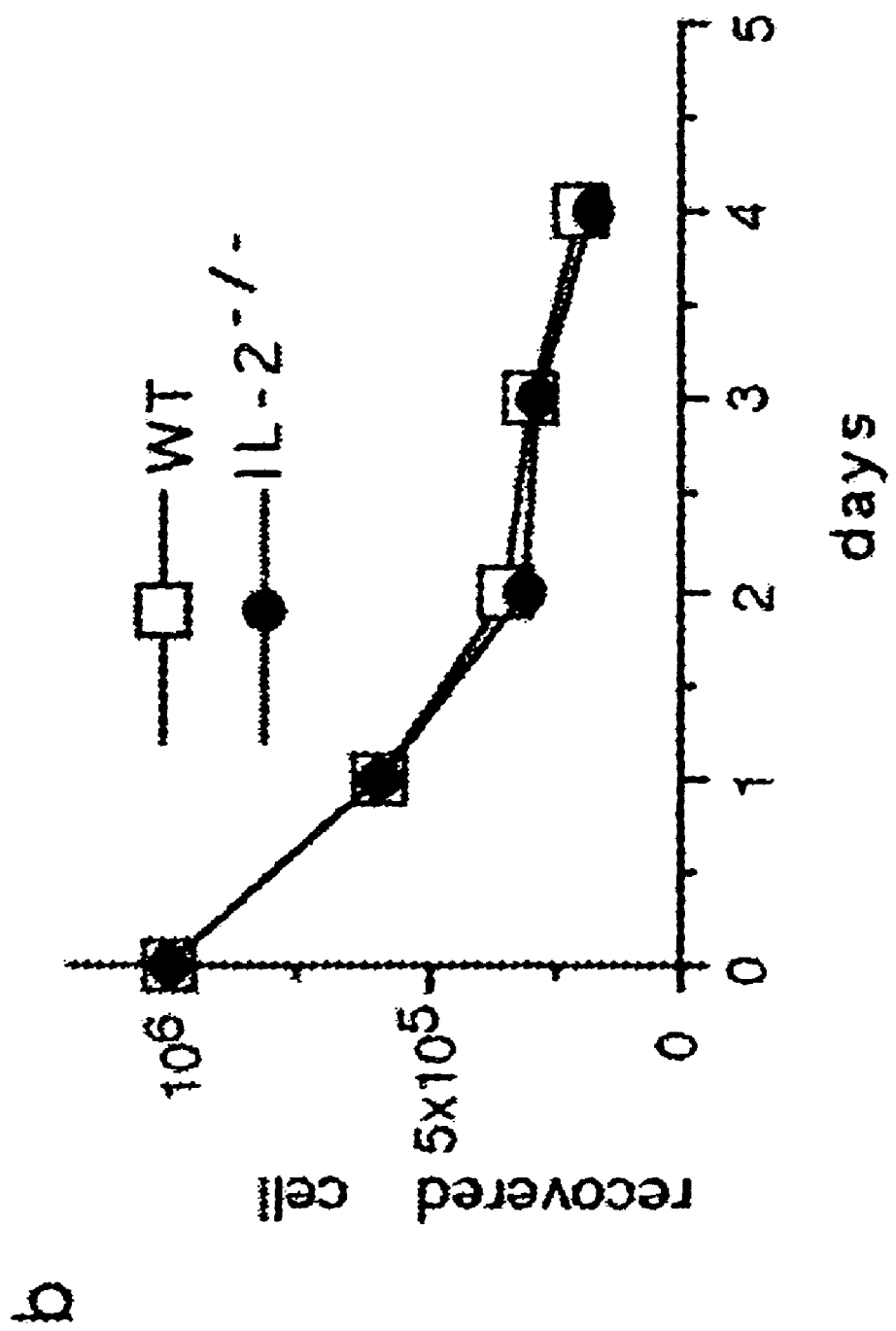
Figure 5C:
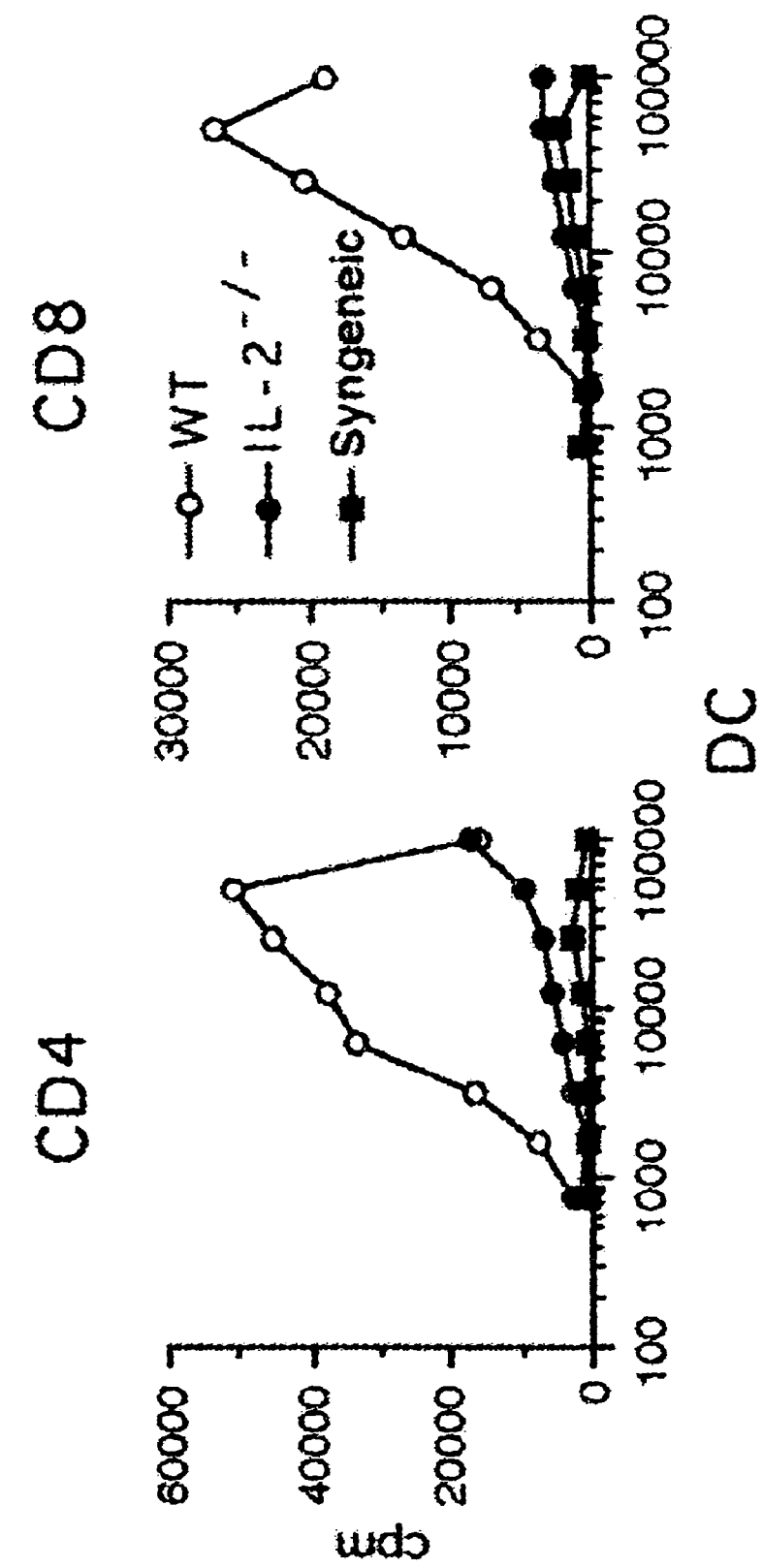
Figure 5D:
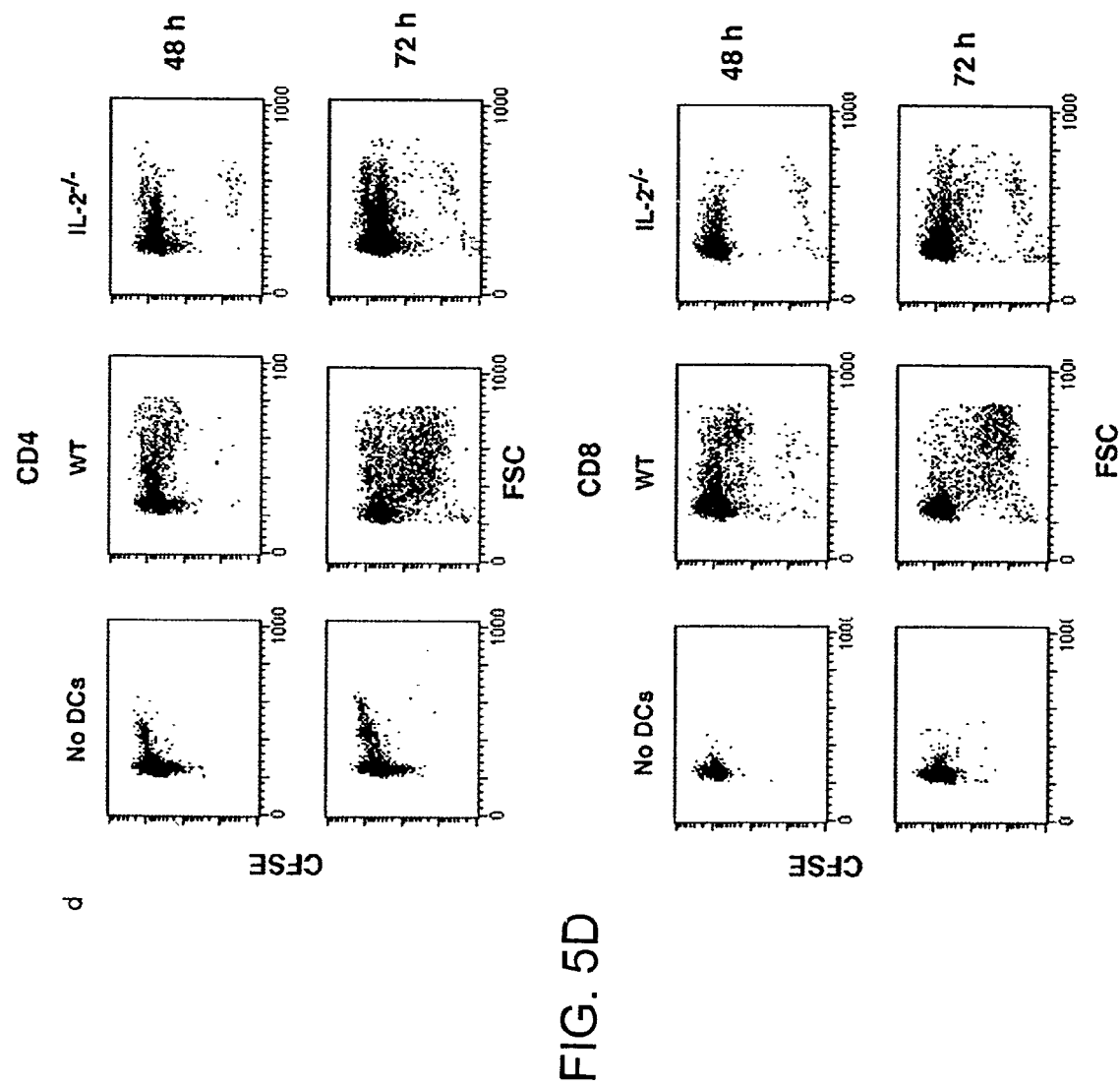
Figure 5E:
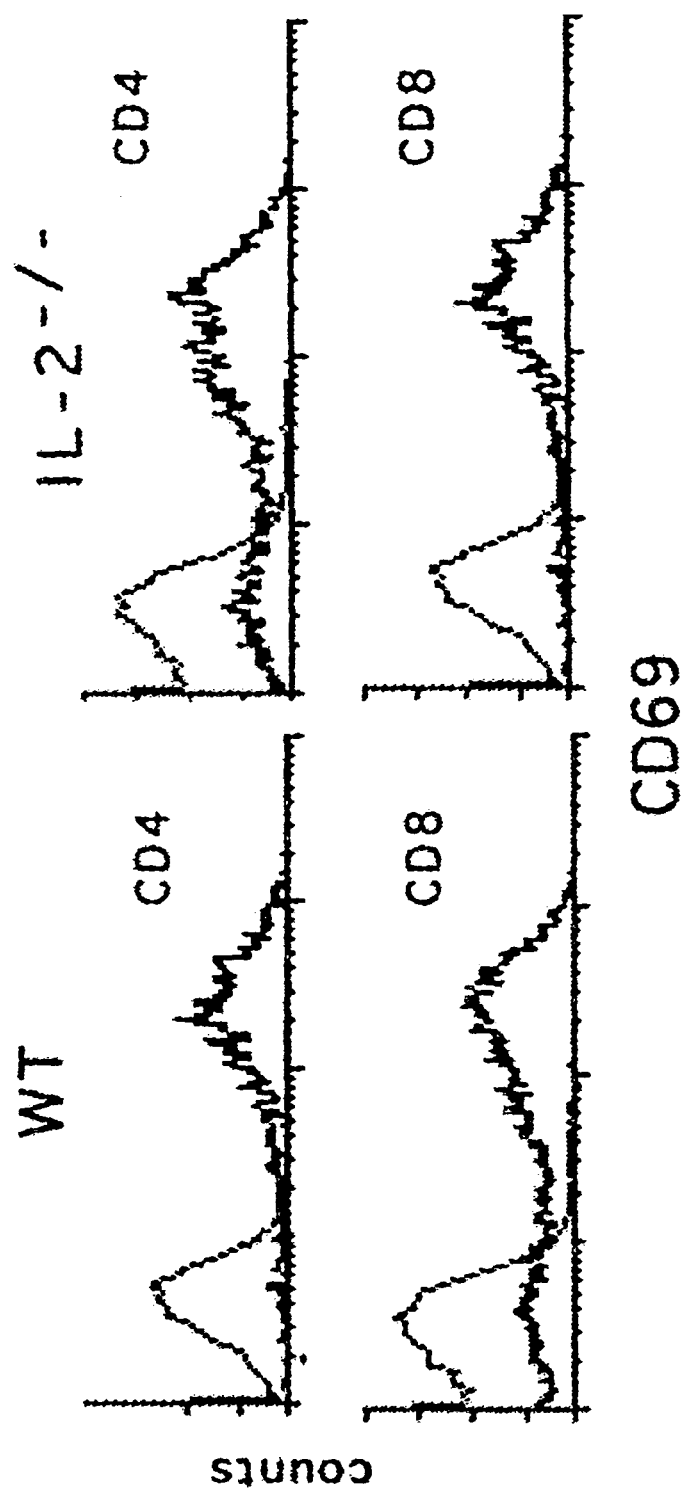

FIGS. 5a to 5e show that DC-derived IL-2 is a key molecule for T cell activation. FIG. 5a shows the activation profile of mBMDC after stimulation with bacteria. Unstimulated DC (thin lines) and 15 h bacterial-activated DC (thick lines) were analyzed by FACS for the expression of the indicated molecules. FIG. 5b shows survival curve of wild type and IL-2$^{-/-}$ DC after bacterial encounter. $10^6$ bacterial 23 activated DC were plated in six well plates and viable cells remaining at the different time point was evaluated by trypan blue exclusion. FIG. 5c shows proliferative response of alloreactive T cells measured by tritiated thymidine incorporation. Graded numbers of bacterial activated wild-type and IL-2$^{-/-}$ DC were incubated with 2×10$^5$ allogeniec T cells in 96 well plates. Background T cells proliferation was evaluated by co-culturing syngeneic T lymphocytes with wild-type DC. Proliferation was assessed after 72 h by 16 h exposure to [$^3$H]thymidine and is expressed as mean cpm of duplicates. (d,e) Alloreactive T cells activation. 5×10$^5$ DC were stimulated with bacteria in 24 well plates and 2×10$^6$ CSFE labeled CD4$^+$ or CD8$^+$ allogeniec T cells were added to the culture. FIG. 5d shows cycling cells were checked at the indicated time points by FACS analysis. FIG. 5e shows that after 48 h of culture the level of CD69 expression was evaluated on small non-cycling T lymphocytes (thin lines) and large T cell blasts (thick lines).

Figure 6:
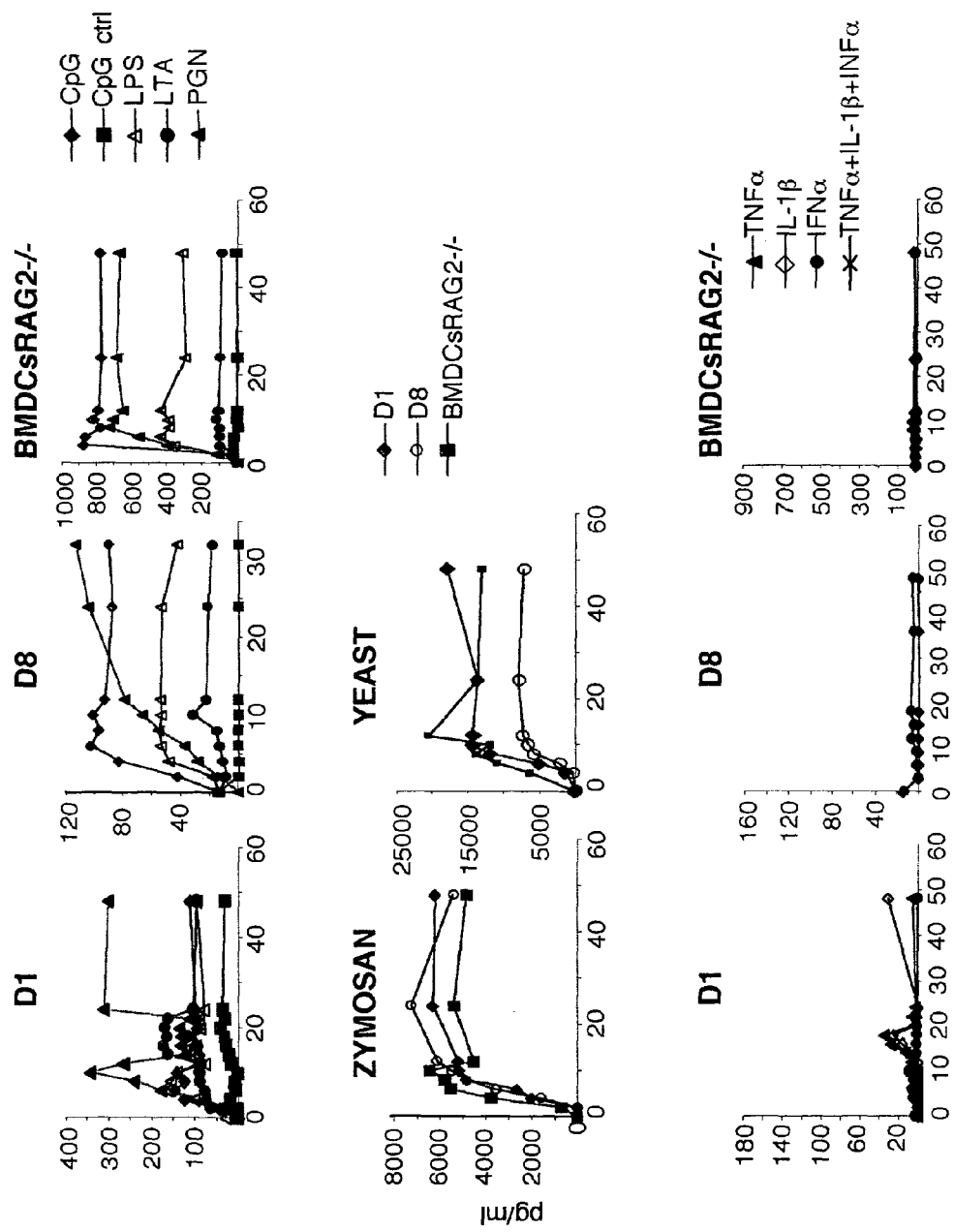

FIG. 6 shows microbial stimulation of IL-2 production by DC.

Figure 7:
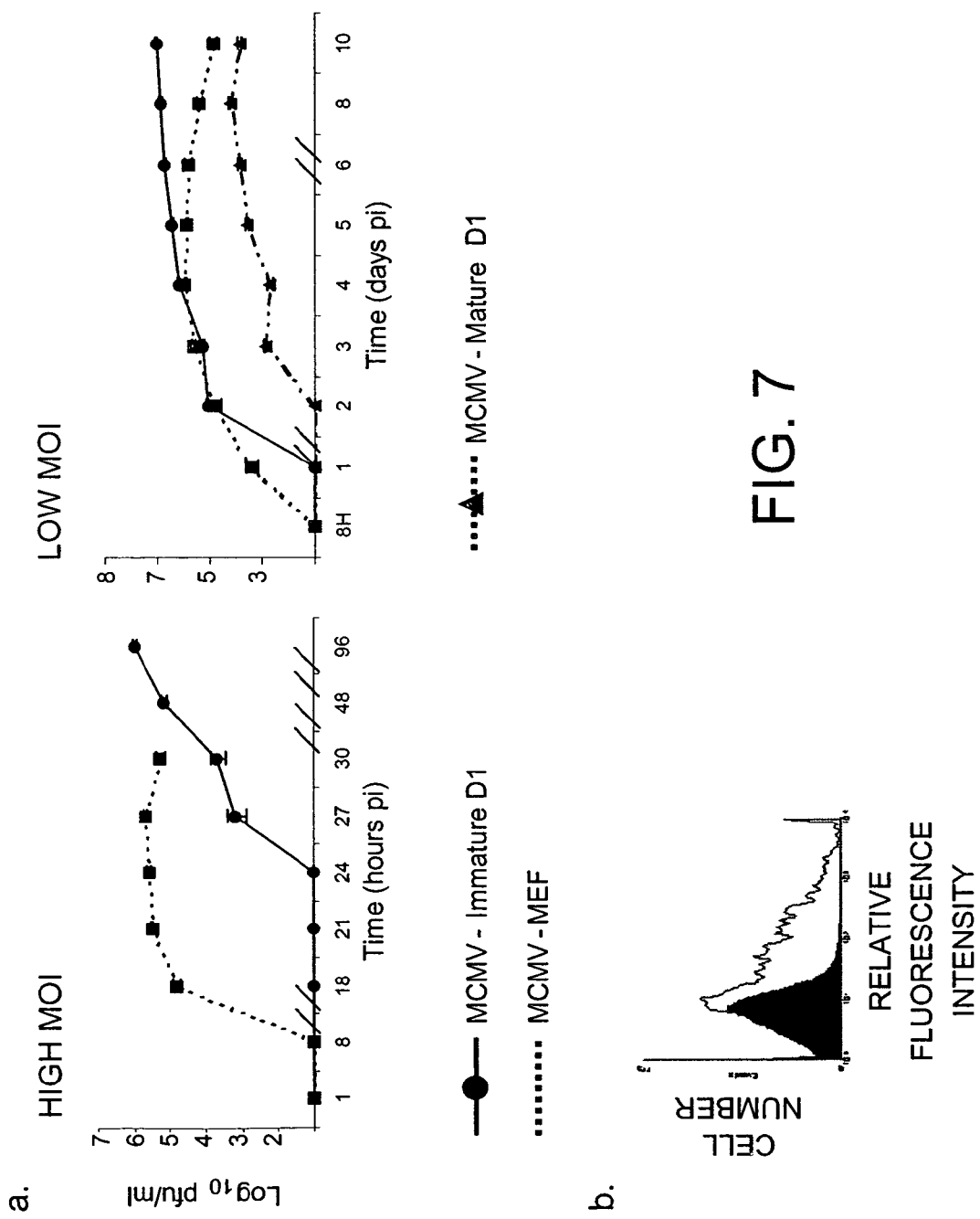

FIGS. 7a and 7b show MCMV infects DC in vitro and in vivo. FIG. 7a shows the replication of MCMV in DC after high and low MOI infection. Cells were infected with an MOI>3 pfu/cell (left panel) and total virus (cell associated and secreted) titers determined at the indicated times post-infection by plaque assay on MEF monolayers. Cells were infected with an MOI of 0.02 pfu/cell (right panel) and total virus titers determined at the indicated times post-infection by plaque assay on MEF monolayers. FIG. 7b shows that MCMV infection was detected by FDG staining to detect DC expressing β-galactosidase 2 days after infection with a LacZ expressing MCMV recombinant virus (unfilled histogram). The filled histogram corresponds to FDG staining of DC from mock-infected animals.

Figure 8:
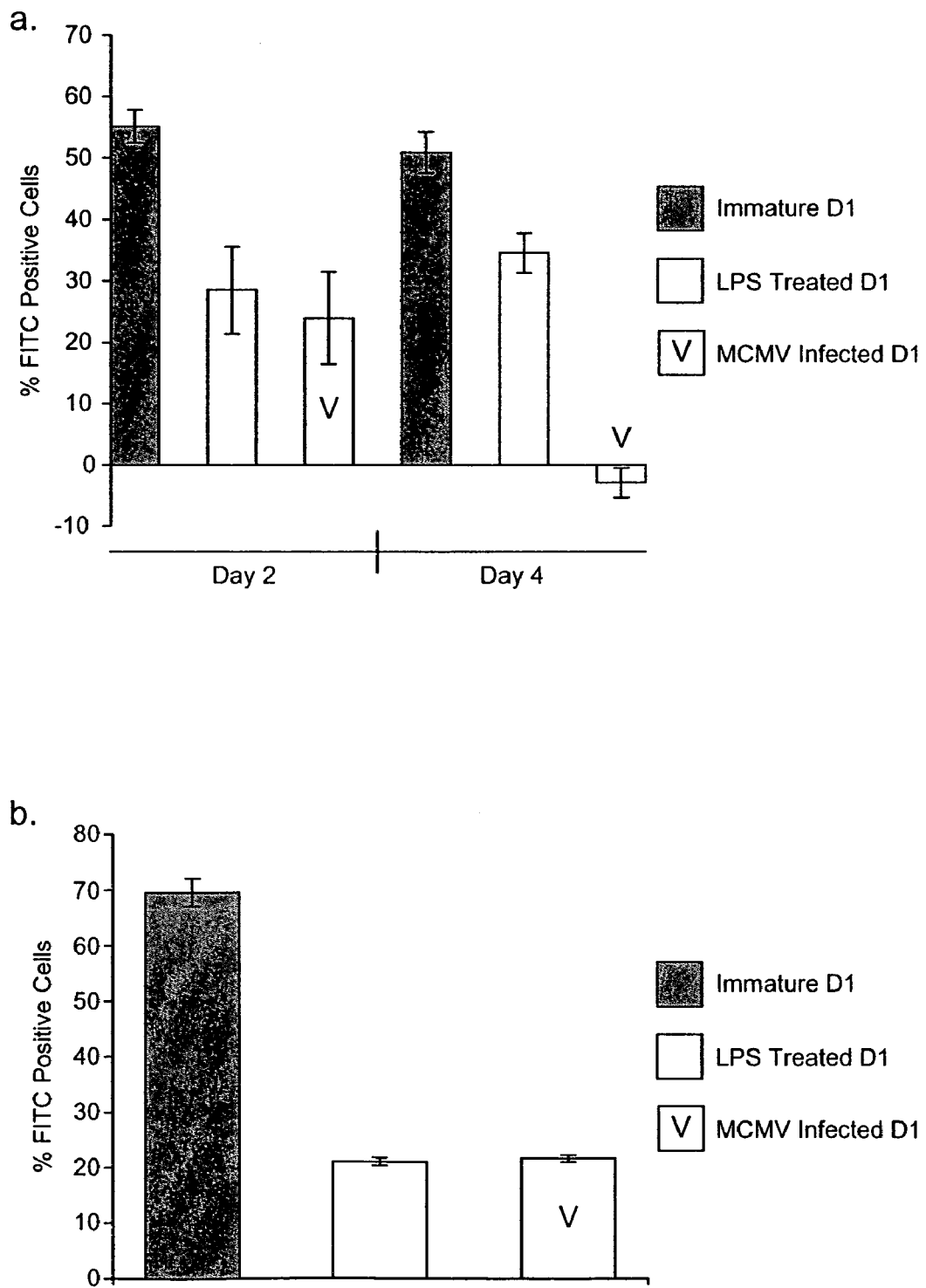

FIGS. 8a and 8b show that MCMV-infected DC show impaired antigen uptake. Antigen uptake (FITC-DX) by D1 cells and fresh DC at different maturation stages (immature vs mature) or following MCMV infection is shown. FIG. 8a shows the antigen uptake by D1 cells. The Mean Fluorescence intensity (MFI) values are as follows: Day 2—MFI values: Immature 62.47±1.36; Mature 9.28±2.44; MCMV-infected—0.57±9.30; Day 4—MFI values: Immature 21.95±1.25; Mature 9.06±0.26; MCMV-infected 2.61±1.22. FIG. 8b shows the antigen uptake by fresh DC. The MFI values of splenic DC harvested at day 2 post LPS or MCMV-infection are as follows MFI values: Immature DC from control animals 187.3±5.9; Mature DC from LPS-treated animals 56±1.65; DC from MCMV-infected animals 57.67±2.28.

Figure 9A:
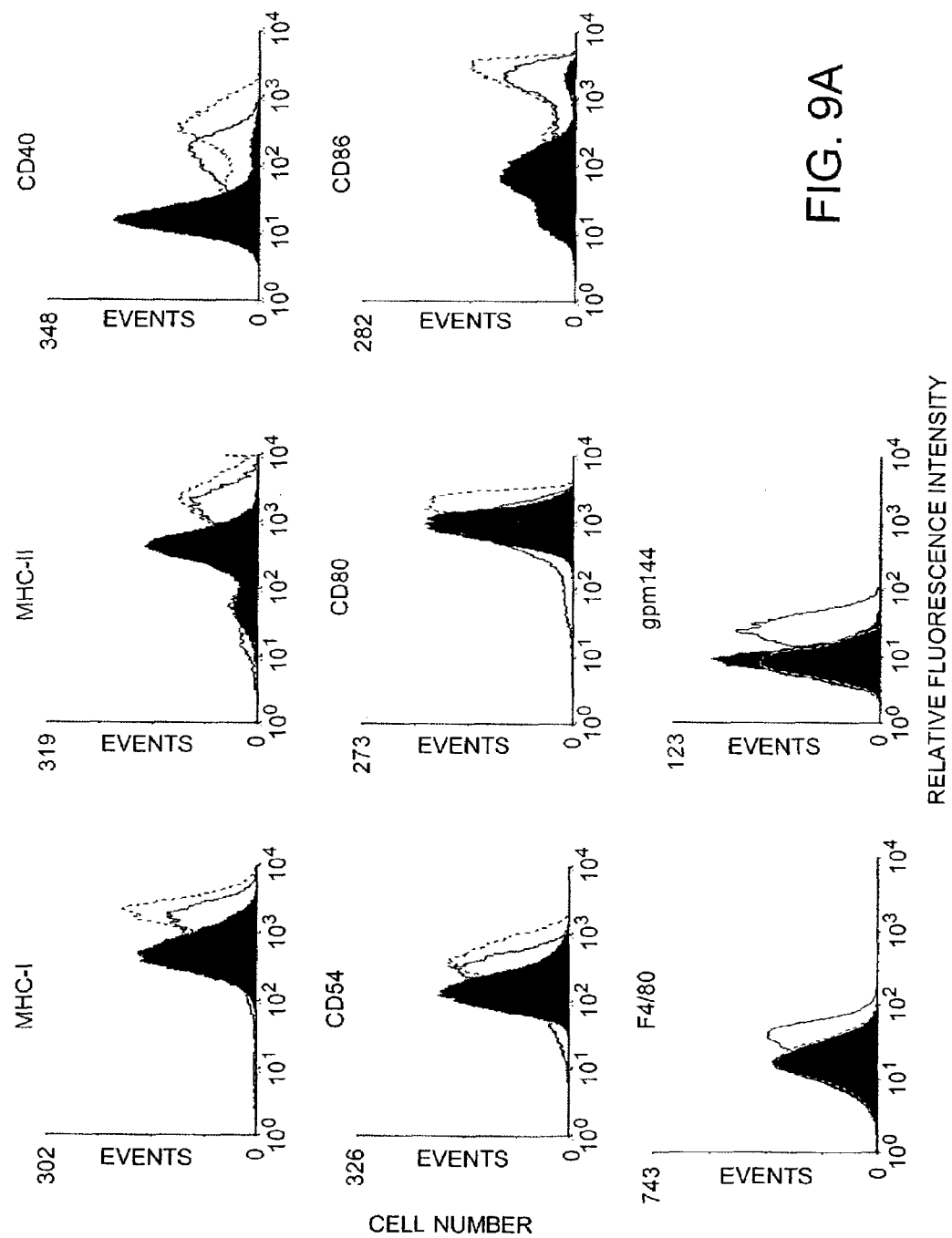
Figure 9B:
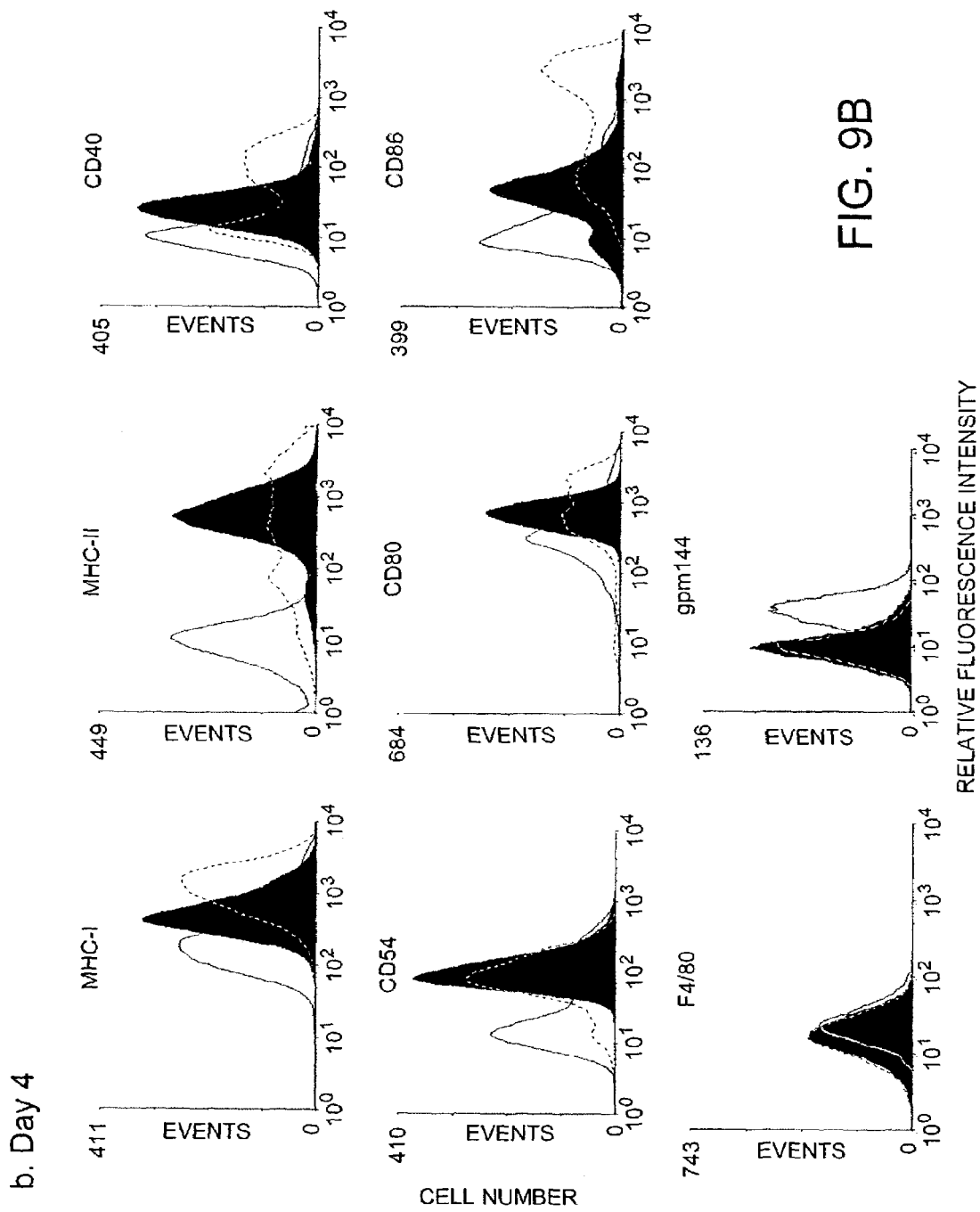

FIGS. 9a and 9b show MCMV infection alters the phenotype of immature DI cells. The expression of MHC and co-stimulatory markers is shown at days 2 (FIG. 9a) and 4 (FIG. 9b) post-MCMV infection (MOI>3) or LPS treatment. Control immature D1 (filled histograms), MCMV-infected (solid line) and LPS treated D1 cells (dotted line) are shown.

Figure 10:
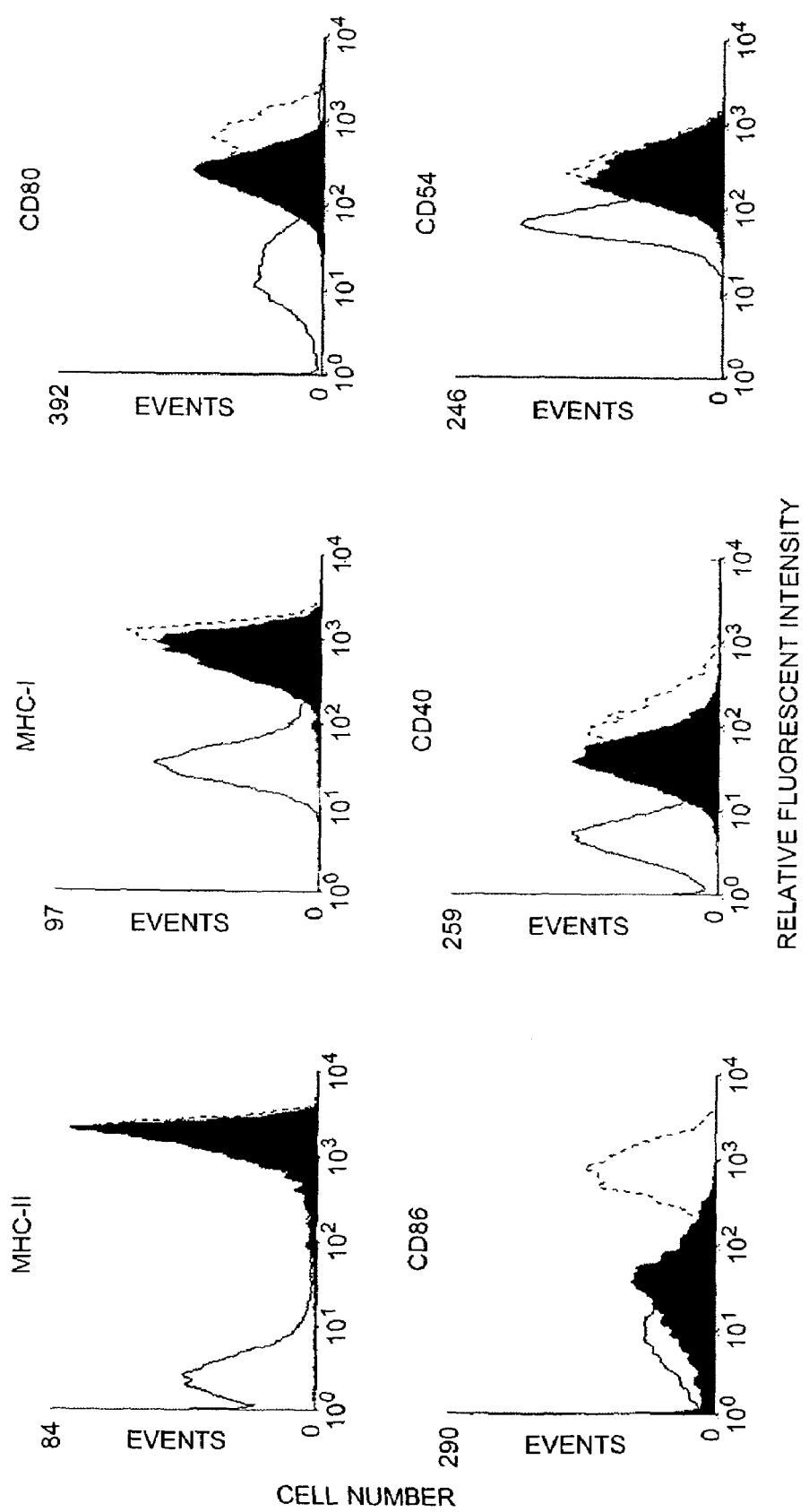

FIG. 10 shows that MHC and costimulatory molecules are down-regulated on MCMV-infected ex vivo derived DC. Expression of relevant markers on splenic DC (CD11c$^{++}$) purified from Flt3L treated mice and cultured with MCMV or LPS for 2-4 days is shown. Cell surface expression of MHC, adhesion and costimulatory molecules is shown on control DC (filled histograms), DC treated with LPS (dotted line) or DC infected with MCMV (MOI>3) (solid line).

Figure 11A:
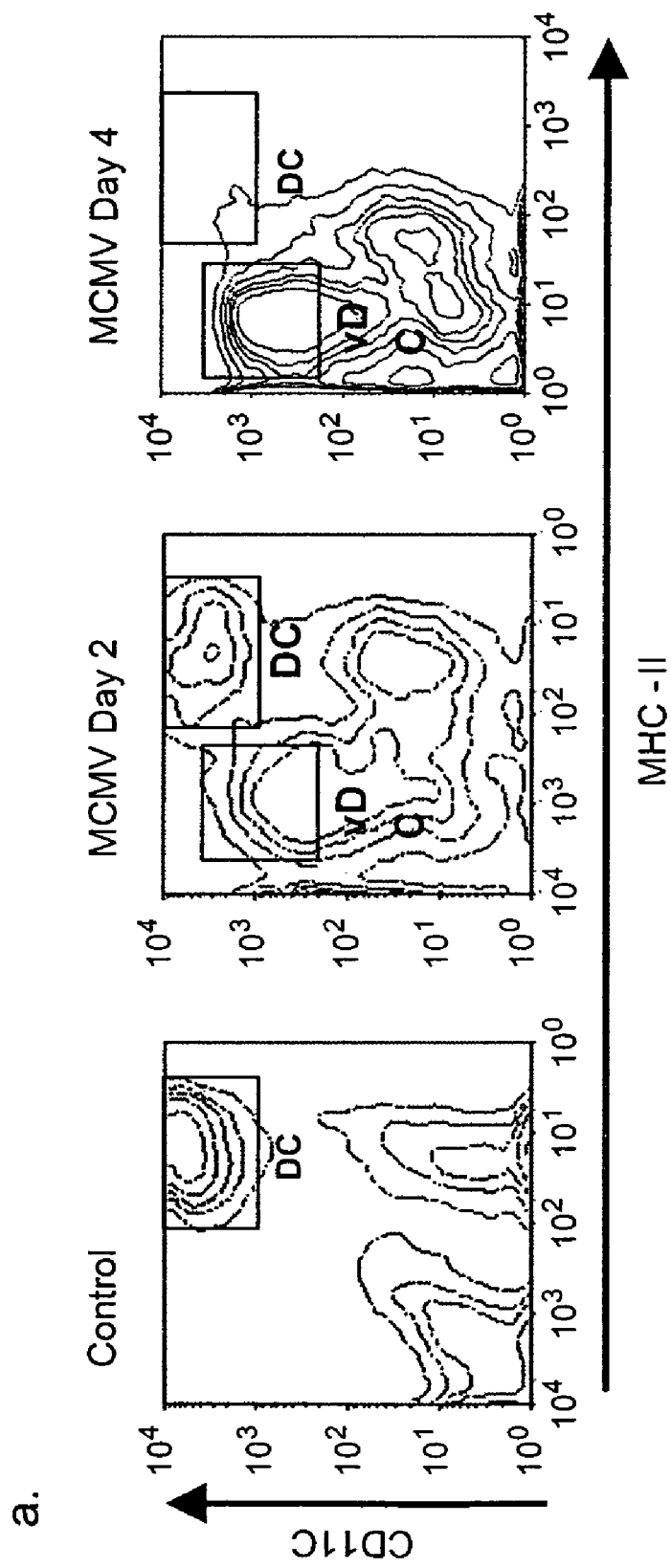
Figure 11B:
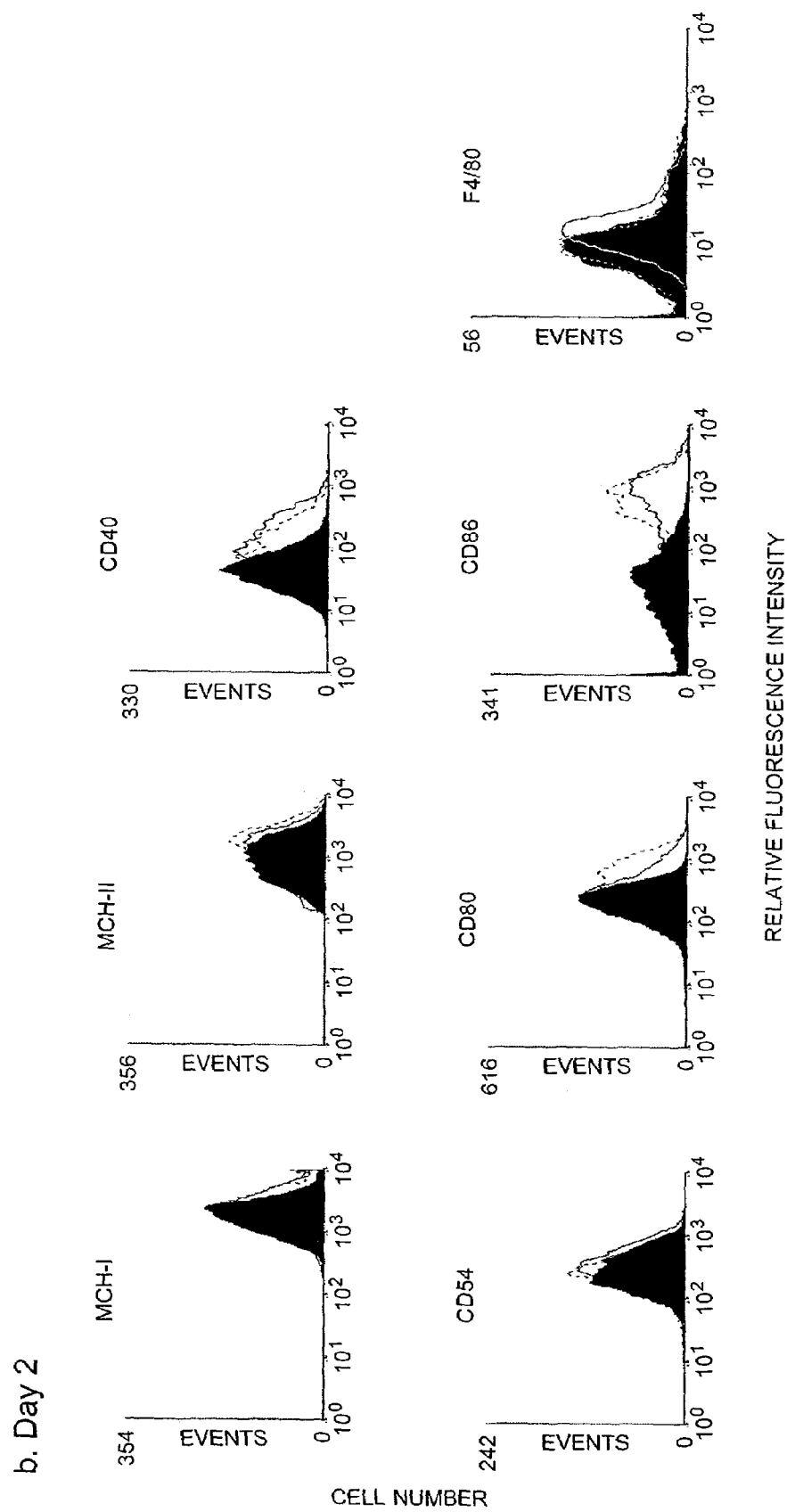
Figure 11C:
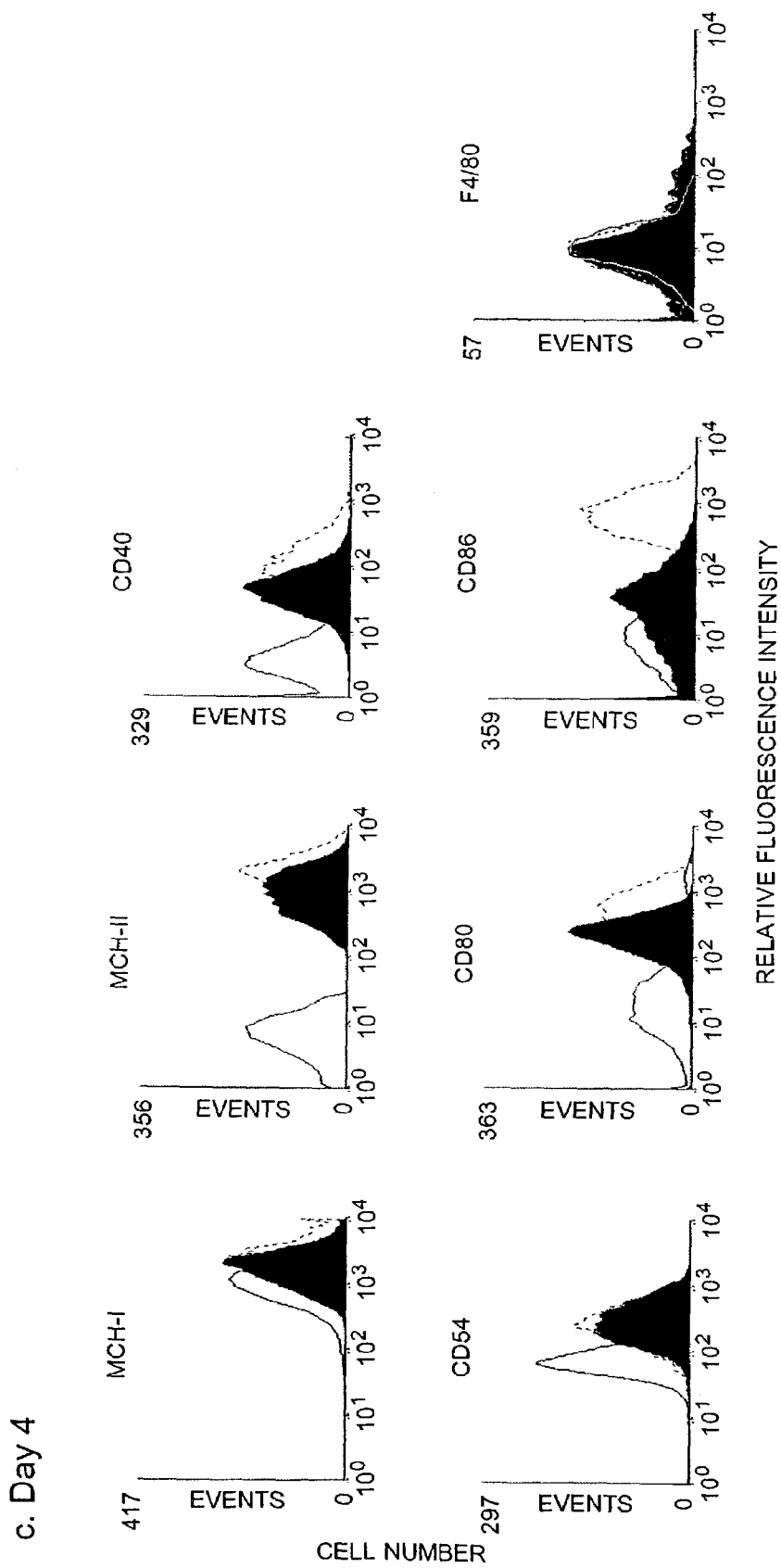

FIGS. 11a to 11c show that MCMV infection down-regulates expression of DC markers on DC in vivo. FIG. 11a shows that CD 11c and MHC-II expression of splenocytes enriched for DC by gradient centrifugation. DC from control mice were compared to DC from mice infected with MCMV for 2 or 4 days. vDC=virally altered DC. The expression of MHC-I/II, CD40, CD54, CD80 and CD86 on splenic DC from mock-infected (filled histogram), LPS-treated (dotted line) or MCMV-infected mice (solid line) is shown at 2 (FIG. 11b) and 4 (FIG. 11c) days post-treatment.

Figure 12:
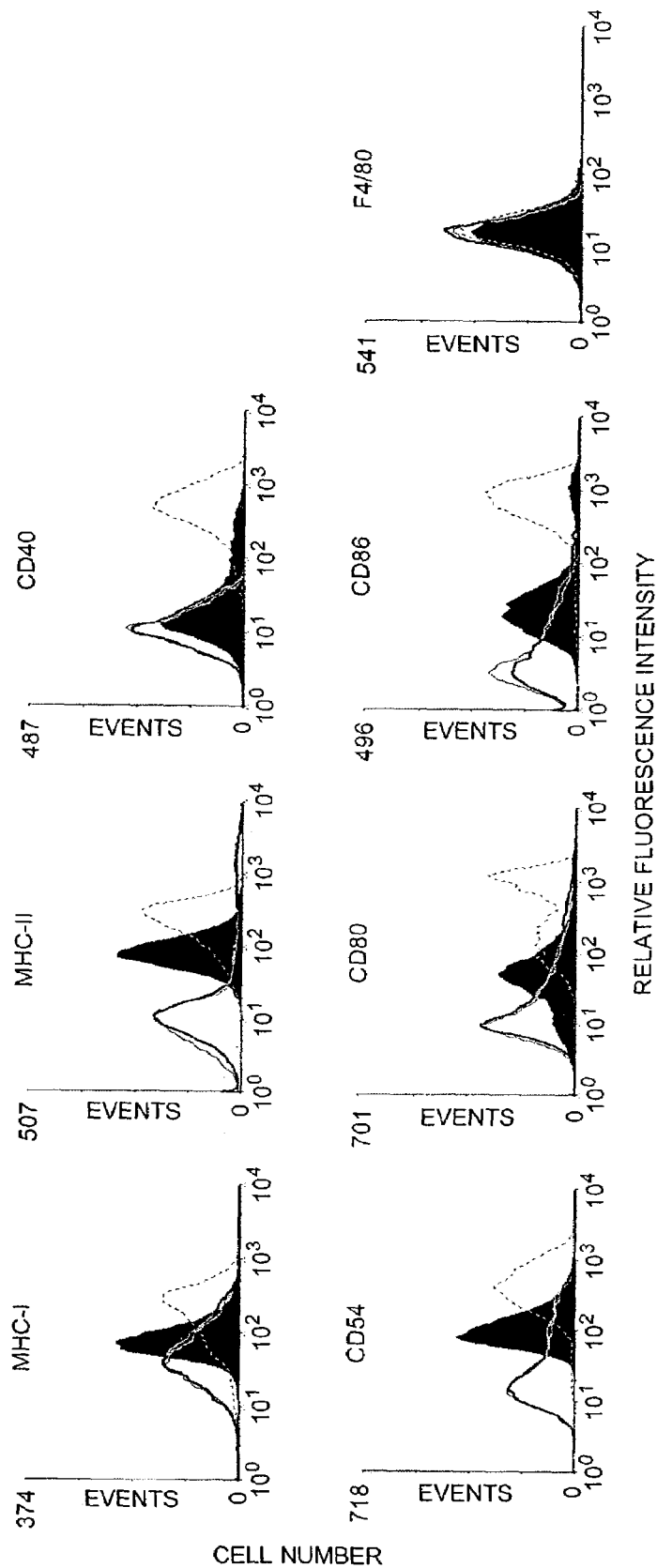

FIG. 12 shows that MCMV-infected DC are refractile to phenotypic maturation following LPS stimulation. The cell surface expression of CD40 and CD86 on D1 cells treated with LPS (10 μ/ml for 48 h) after being infected with MCMV for 4 days (thin solid line) is shown. For comparison expression of these markers on MCMV-infected non-treated D1 cells (thick solid line), immature D1 cells (filled histogram) and LPS activated uninfected D1 cells (dotted line) is shown.

Figure 13:
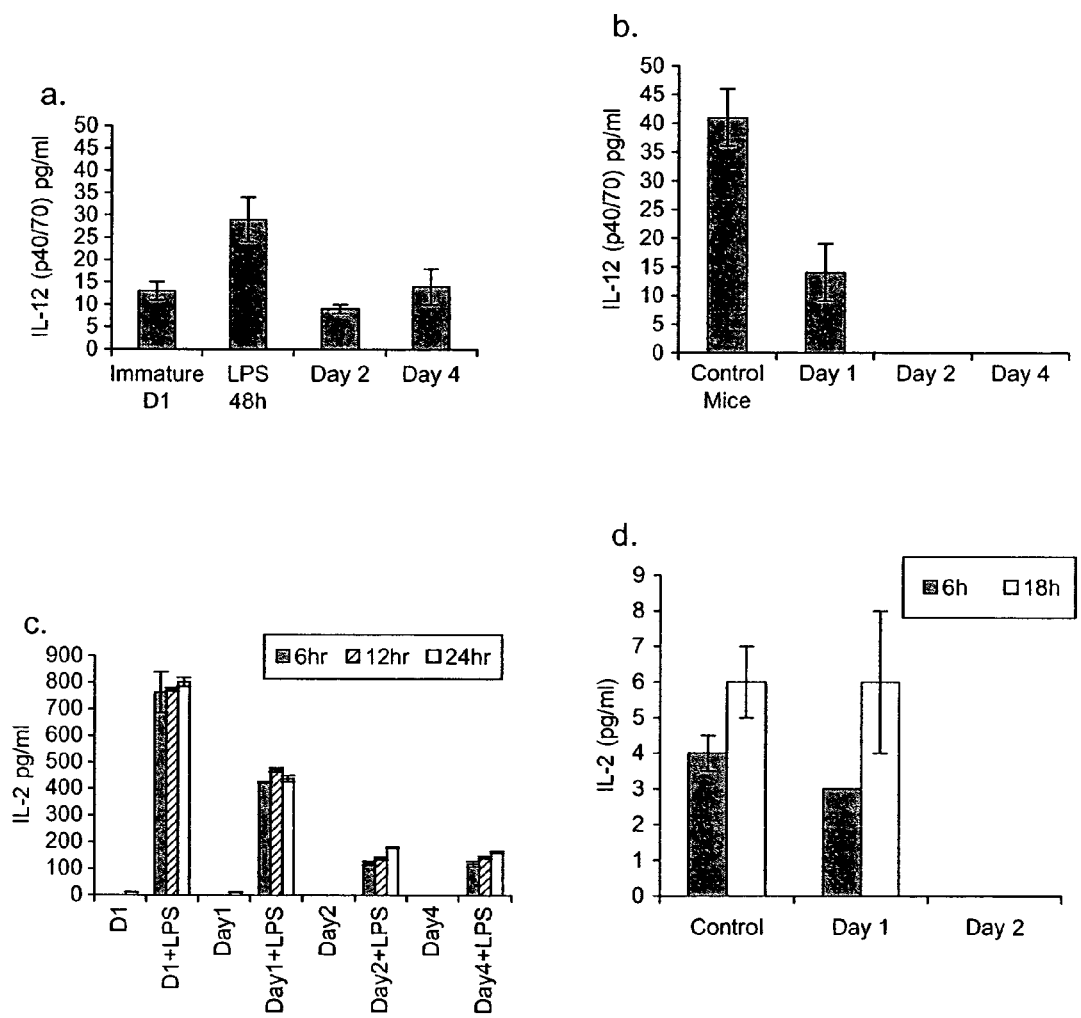

FIGS. 13a to 13d show that MCMV infection alters the secretion of IL-12 and IL-2 by DC. FIG. 13a shows the levels of IL-12 secreted after LPs treatment or MCMV infection of D1 cells. FIG. 13b shows the levels of IL-12 secreted by splenic DC harvested from control or MCMV-infected mice (days 1, 2 or 4 post-infection) and cultured in the presence of LPS for 18 h. FIG. 13c shows IL-2 secreted by MCMV-infected D1 cells treated with LPS for various periods of time. The amount of IL-2 secreted by control and uninfected LPS-treated D1 is shown for comparison. FIG. 13d shows the levels of IL-2 secreted by splenic DC harvested from control or MCMV-infected mice (days 1 or 2 post-infection) and cultured in the presence of LPS for 6 or 18 h.

Figure 14:
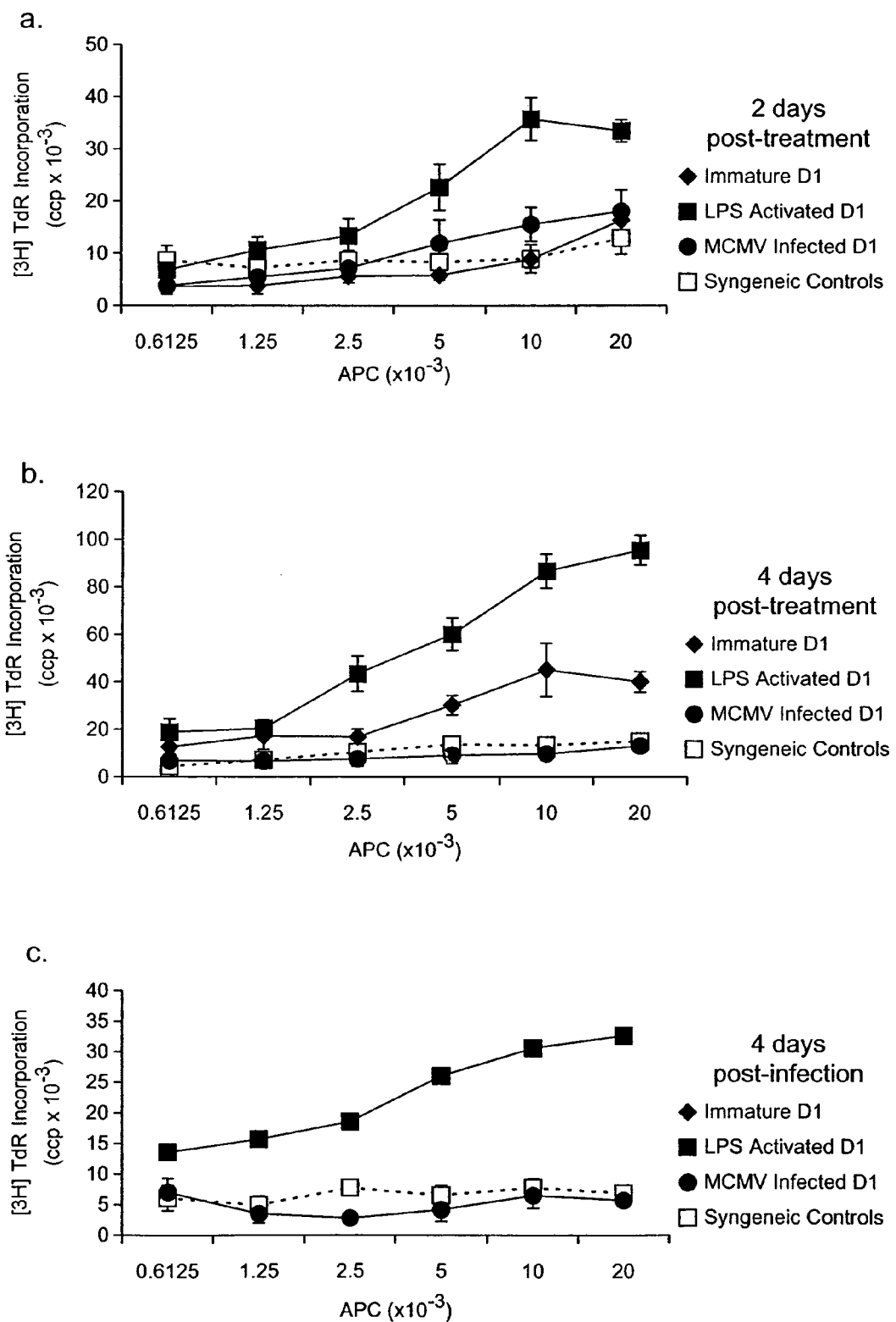

FIGS. 14a to 14c show that MCMV infection of DC impairs their allostimulatory capacity. The allostimulatory capacity of D1 cells infected with MCMV for 2 (FIG. 14a) or 4 (FIG. 14b) days is shown together with that of DC purified from the spleens of mice infected with MCMV for 4 days (FIG. 14c). D1 cells or purified splenic DC activated with LPS (10 μ/ml for 48 h) were used as controls. For the D1 ($H2^b$, $I-A^b$) experiments, splenocytes from BALB/c ($H2^d$, $I-A^d$) mice were used as the allogeneic responders and splenocytes from C57BL/6 mice were used as the syngeneic controls. Conversely, in experiments were the stimulators were DC purified from BALB/c mice, splenocytes from C57BL/6 mice were used as the allogeneic responders and splenocytes from BALB/c mice were used as the syngeneic controls.

Figure 15:
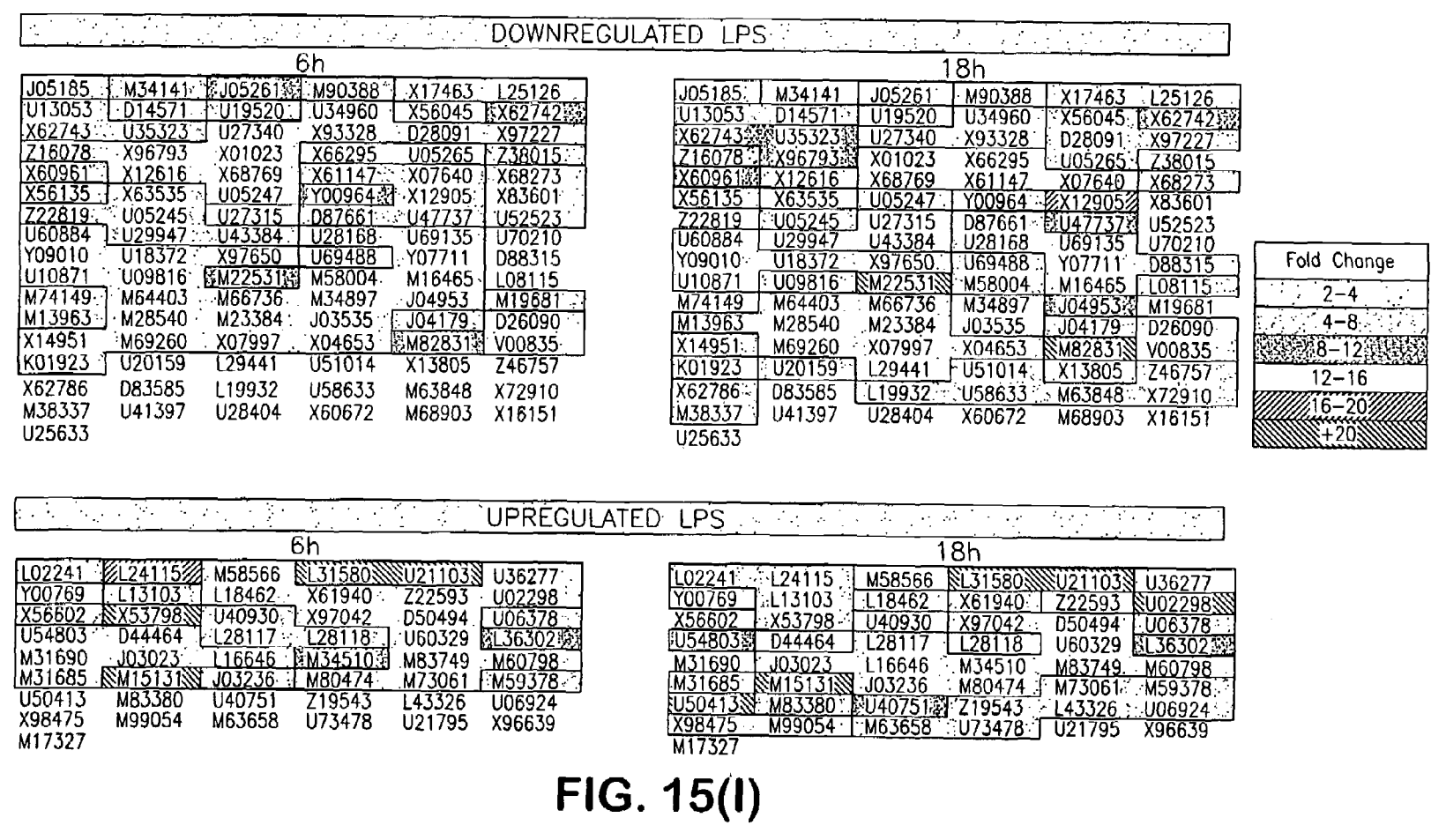
Figure 15II:
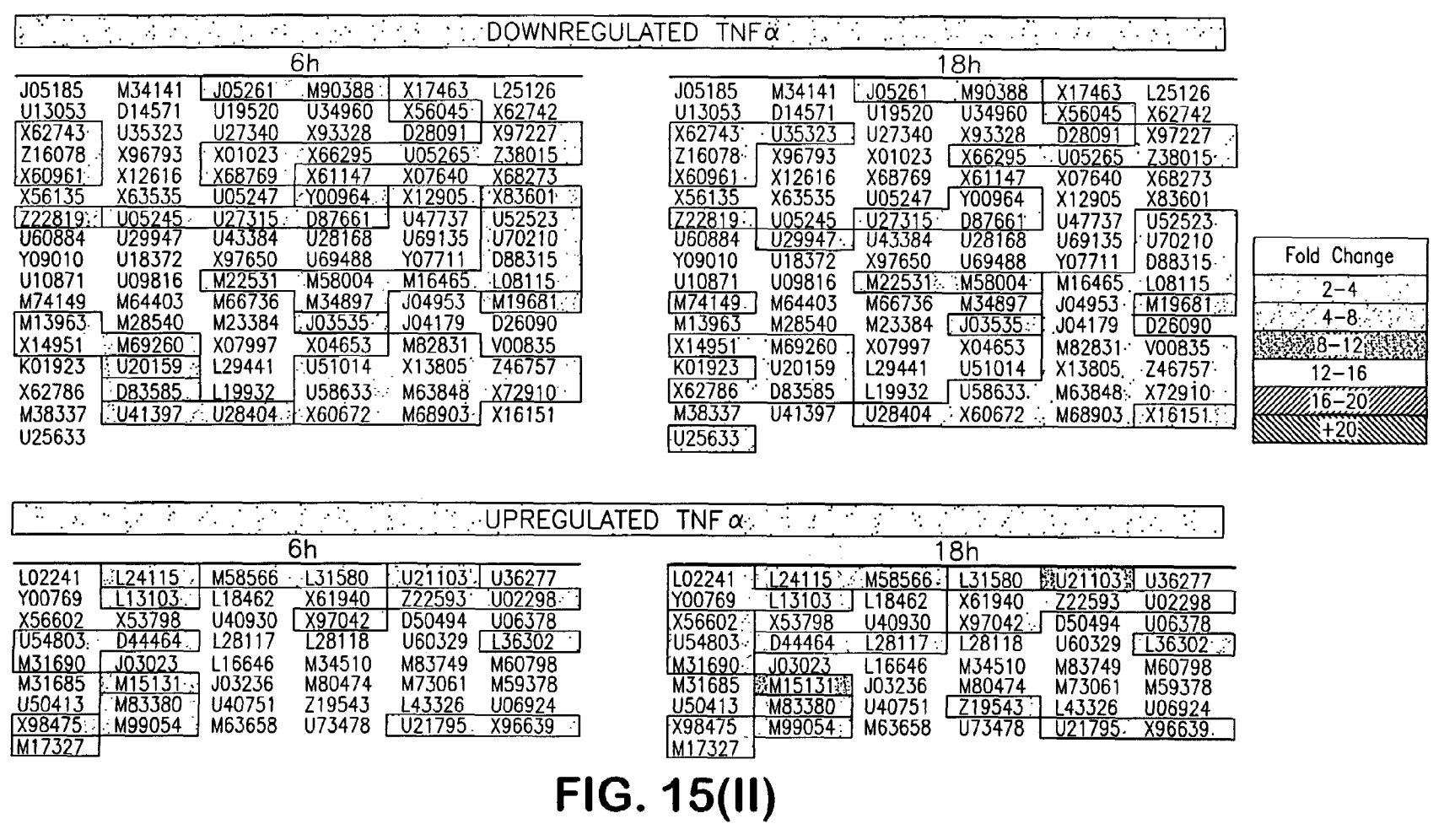
Figure 15III:
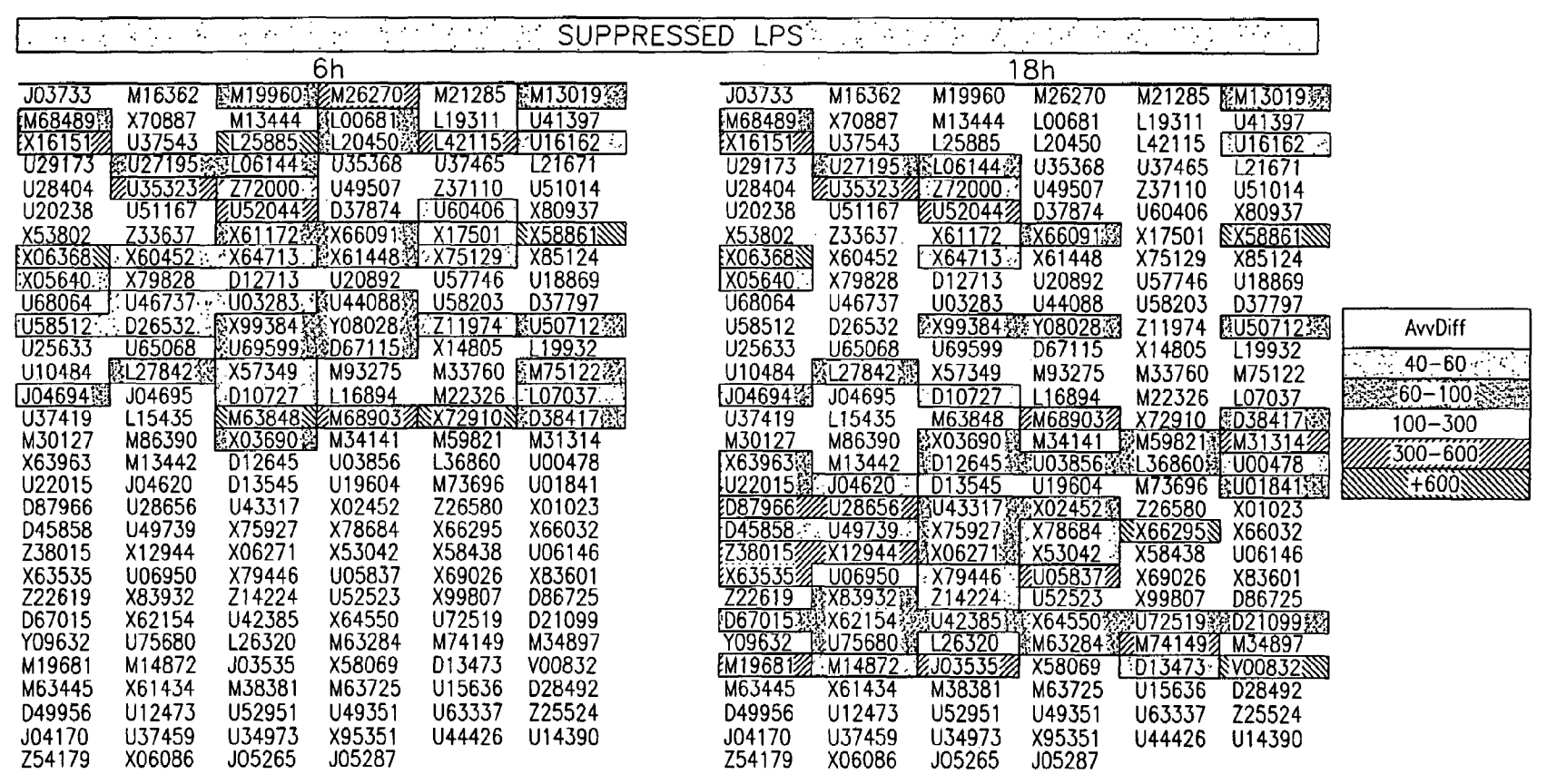
Figure 15IV:
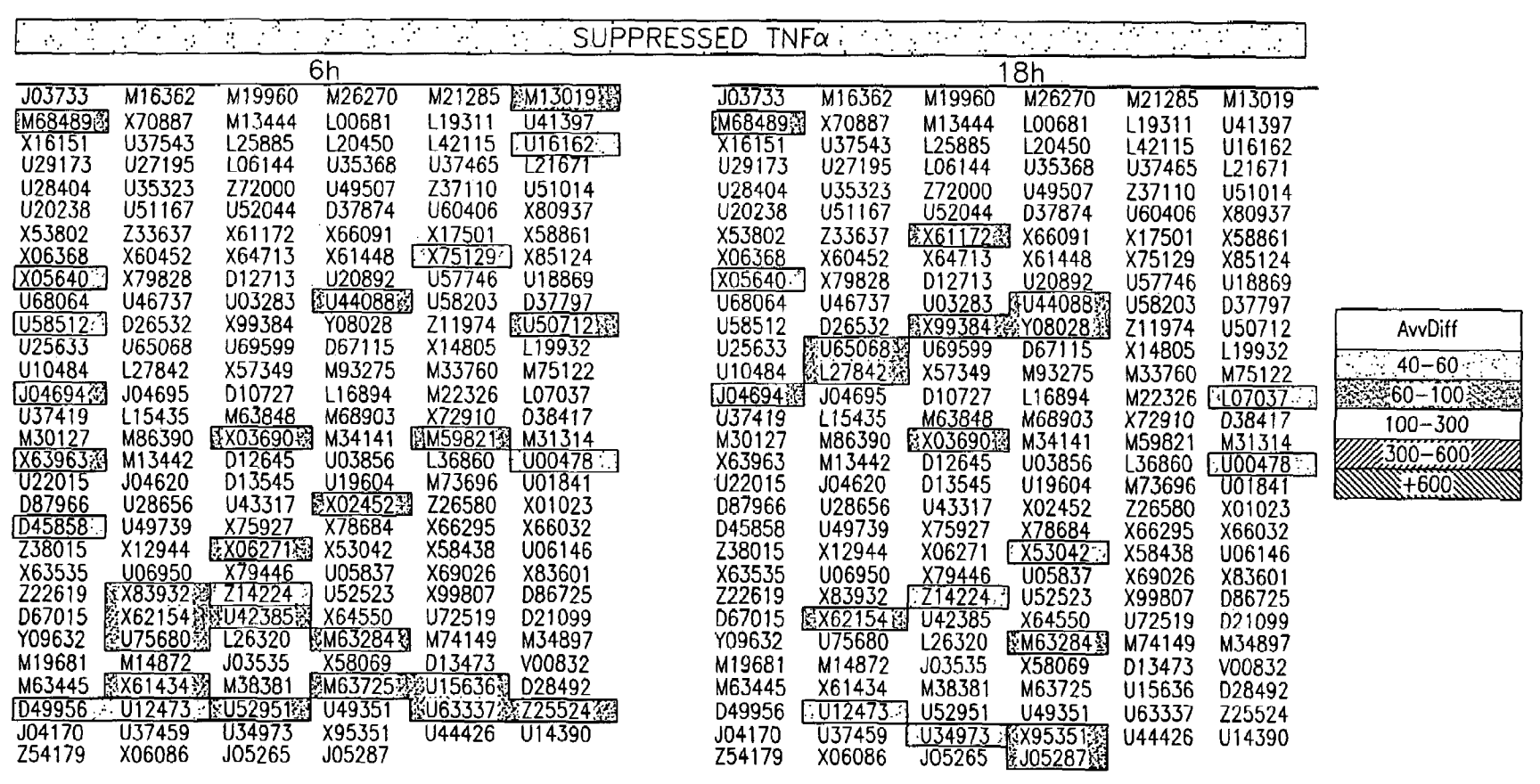
Figure 15V:
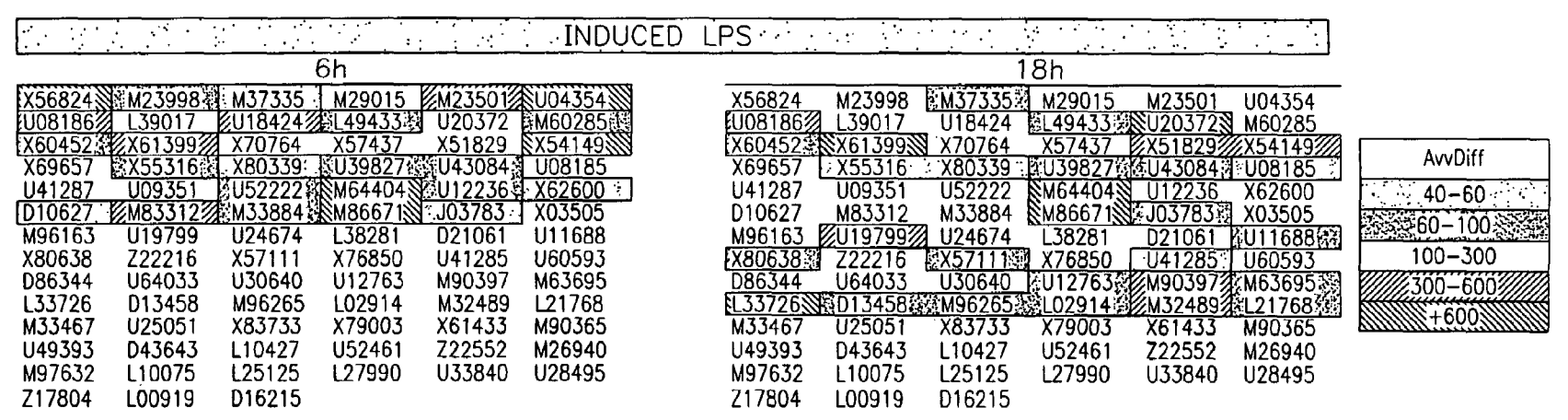
Figure 15VI:
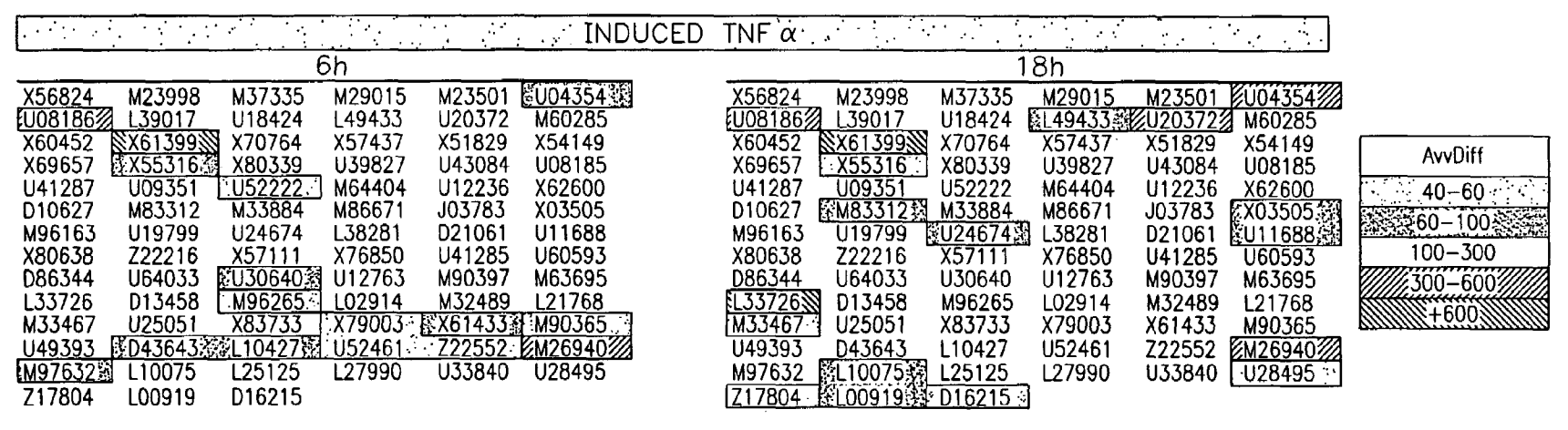

FIG. 15 shows known genes differentially expressed in LPS- and TNF-α-activated DC versus unstimulated cells. Genes were divided in four groups (induced, suppressed, up-regulated, down-regulated) and represented by their GenBank accession numbers. Fold change values are indicated for up-regulated and down-regulated genes. Intensity values before and after stimulation are shown for suppressed and induced genes, respectively. Genes in white boxes are not modulated under the indicated conditions.

Figure 16:
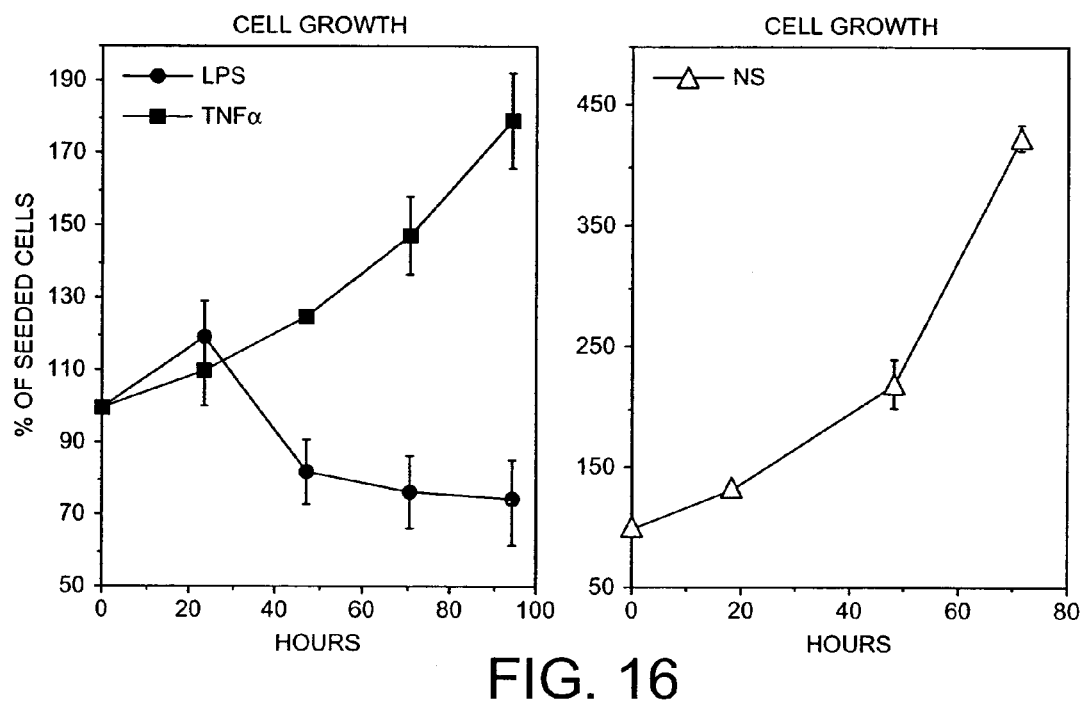

FIG. 16 shows that LPS but not TNF-α induces definitive growth arrest of DC. D1 cells were stimulated either with LPS or TNF-α for the indicated time. The number of viable cells at the indicated time points is expressed as percentage of seeded cells. LPS, LPS-stimulated cells; TNF-α, TNF-α-stimulated cells; NS, non-stimulated cells. Standard deviations of five independent experiments are reported.

Figure 17:
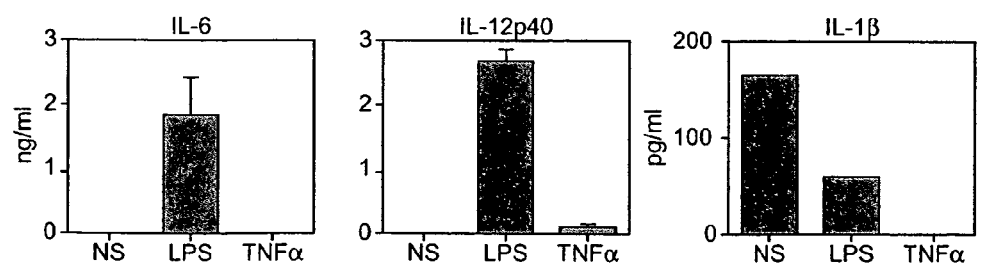

FIG. 17 shows cytokine production after LPS and TNF-α treatment. Supernatants of unstimulated, TNF-α-and LPS-treated DC were collected 18 h after stimulation and tested by ELISA for the presence of IL-6, IL-12p40 and IL-1β.

DESCRIPTION OF THE PREFERRED EMBODIMENTS

The present invention relates in general to dendritic cells and their association with immune responses. It is the discovery of the present invention that micorbial stimuli induce distinct gene expression profiles in dendritic cells which initiate various immune responses. Accordingly, the present invention provides methods of making dendritic cell gene expression profile libraries and the libraries made thereof in response to microbial stimuli. In addition, the present invention provides methods of inducing IL-2 in dendritic cells and using IL-2 to activate lymphocytes and immune responses in association with dendritic cells. The present invention also provides methods and systems useful for screening agents capable of affecting dendritic cell maturation.

It is also the discovery of the present invention that dendritic cells are targeted by immunosuppressive virus infections, e.g., CMV or HIV infection. Accordingly, the present invention provides methods for treating immunosuppressive virus infections and immunosuppresions associated with immunosuppressive virus infections. The present invention also provides methods for screening candidate therapeutic agents suitable for treating immunosuppressive virus infections. The present invention also provides methods for screening for the immunosuppressive effects of tumors on dendritic cells, thus providing methods for screening candidate therapeutic agents suitable for the treatment of such tumors.

According to the present invention, methods for making a gene expression profile library for dendritic cells exposed to a microbial stimulus include incubating immature dendritic cells with a microbial stimulus, e.g., dendritic cell maturation stimulus, identifying genes in the dendritic cells that have changed their levels of expression in response to the microbial stimulus, e.g., either a substantial increase or decrease of the gene expression level, and generating a gene expression profile, e.g., in a computer readable media indicating the genes and levels of changes corresponding to the stimulus.

In one embodiment, gene expression profiles are generated by identifying differentially expressed genes in dendritic cells upon exposure to a microbial stimulus. A microbial stimulus of the present invention can be any stimulation that triggers dendritic cell maturation, e.g., IL-2 production of dendritic cells. For example, a microbial stimulus can be a microorganism or one or more products or components thereof. In one embodiment, the microbial stimulus of the present invention includes microorganisms, e.g., bacteria, viruses, fungal organisms and prions. In another embodiment, the microbial stimulus of the present invention includes Gram+bacteria, lipoteichoic acid (LTA, a component of Gram+bacteria), Gram-bacteria, LPS (a component of Gram-bacteria), oligonucleotides containing unmethylated CpG motif, zymosan, yeasts, e.g., *Saccaromycies Cerevisiae*, and stimuli mediated by T cell help such as anti-CD40 antibodies.

Levels of gene expressions can be determined using any suitable means available to one skilled in the art. For example, levels of gene expression can be determined by detecting the levels of gene transcripts using microarrays representing 11000 genes and expressed sequence tags (ESTs). One way of analyzing levels of gene expression in general is by using Principal Component Analysis (PCA) method, which allows the dimensionality of complex data to be reduced.

Differentially expressed genes can be identified using any means known to one skilled in the art. For example, a first gene clustering algorithm can be used which groups genes according to the similarity of their expression patterns based on Self-Organizing Maps (SOMs). Genes or ESTs are excluded from the profile if the changes of their expression are below a predetermined level based on mean average differences. Each SOMs can also be further analyzed using a second gene clustering method, e.g., Hierarchical clustering.

According to the present invention, one of the dendritic cell gene expression profiles includes IL-2 production in response to a microbial stimulus. Therefore, one aspect of the present invention provides methods for activating lymphocytes or immune responses using IL-2.

In one embodiment, methods for activating lymphocytes include contacting the lymphocytes with IL-2 in the presence of dendritic cells. Lymphocytes to be activated according to the present invention can be any cells associated with an immune response, e.g., effector cells of an immune system including, without limitation, NK cells, NKT cells, B cells and T cells. Dendritic cells used in the methods can be dendritic cells in vivo or dendritic cells cultured in vitro. Usually dendritic cells of the present invention can be either mature or immature dendritic cells or a mixture thereof. In one embodiment, dendritic cells include D1 cells, Langerhans cells, CD8α positive cells, CD8α negative cells, and CD11c positive cells. In another embodiment, dendritic cells are endogenous to a subject, e.g., a mammal such as human containing the lymphocytes to be activated.

IL-2 used in the present invention can be any agent providing an IL-2 function upon either administering or contacting the lymphocytes to be activated. For example, IL-2 used in the present invention can be full-length IL-2, functional equivalents of IL-2, or an agent inducing IL-2 production in a predetermined manner in a subject containing the lymphocytes to be activated. In general, IL-2 used in the present invention can be either in active form or activated upon exposure to lymphocytes. In one embodiment, IL-2 is exogenous to the dendritic cells or lymphocytes to be activated.

Another embodiment of the present invention provides methods for activating immune responses in a subject contacted by or exposed to a dendritic cell stimulus. The method includes administering to the subject an effective amount of IL-2, which in combination with dendritic cells stimulated by the dendritic cell stimulus activates the immune response. The dendritic cell stimulus can be any stimulation that activates dendritic cells or induces maturation of dendritic cells. In one embodiment, a dendritic cell stimulus induces IL-2 production in dendritic cells. In another embodiment, a dendritic cell stimulus is a micorbial stimulus.

The method provided by the present invention is useful for activating any immune response associated with dendritic cells. In one embodiment, the immune response activated is an innate or adaptive immune response. In another embodiment, the immune response to be activated includes, without limitation, priming naïve T cells and activation of NK, B or T cell responses.

According to another aspect of the invention, IL-2 production in dendritic cells is associated with activation of toll like receptors (TLRs) of dendritic cells or T cell help mediated stimulation to dendritic cells. Therefore, the present invention provides methods for inducing IL-2 production in dendritic cells by contacting dendritic cells with an agent activating one or more TLRs in dendritic cells or stimulating dendritic cells via T cell help. Such agent can be any known or later discovered agent including, without limitation, a microbial stimulus. In one embodiment, such agent does not include any inflammatory cytokines.

TLRs activated by the agent can be any TLRs of dendritic cells including, without limitation, TLR2, TLR4, and TLR9. Dendritic cells obtained by such method can be used for any purpose either in vivo or in vitro. For example, dendritic cells containing activated TLRs can be used for cell-based therapies, e.g., inducing immune responses for therapeutic treatment of malignant growth or infectious diseases.

A method for identifying a compound that affects gene expression in dendritic cells.

A method for identifying a compound that affects gene expression in dendritic cells (DC) is presented. The method is based on the use of DC in a variety of specific-assays to monitor DC-specific activities. Dendritic cells are cells of the immune system that originate from bone marrow and belong to the myeloid lineage. DC are strategically located in tissues that represent pathogen entry routes (mucosal surfaces, skin etc.) where they continuously monitor the environment through the uptake of microorganisms. DC play a key role as "sentinels" of the immune system since they are professional antigen presenting cells initiating the antigen-specific immune response and activating NK (natural killers) innate responses. Both functions are inducible in DC by microorganisms or microbial products uptake. This perturbation induce the so-called "DC-maturation" process. DC maturation is associated with reduced phagocytic and endocytic capacities, enhanced production of inflammatory cytokines and chemokines and acquisition of migratory functions allowing antigen loaded DC to move from no-lymphoid tissue or within lymphoid tissues, to migrate from the marginal zones to the T cell areas. Mature DC have acquired high cell surface major histocompatibility complex (MHC) and costimulatory protein expression, have the ability to prime and activate CD8+ and CD4+ T cell responses and are programmed for apoptotic death.

We have found that one of the molecular mechanisms of KN and T cell activation by DC is mediated through interleukin-s (IL-2) production. Transcriptional reprogramming of DC occurs after few hours (4-8 hrs) after microbial uptake. As an example of inducible transcriptional reprogramming and regulation of DC expression, we show that phagocytosis, a Gram-bacterium, by DC leads to transcriptional activation and production of IL-2. In contrast, ingestion of immunosuppressive viruses, such as the cytomegalovinis (MCV) leads to the inhibition of inducible IL-2 transcription in DC. Thus, transcriptional regulation by different biologically relevant perturbations can occur in DC cultured in vitro.

We propose to use DC-based bioassays for the identification of induced/suppressed cellular targets following DC perturbation. As a example, we propose a DC-based bioassay in which regulation of IL-2 expression can be monitored. To establish such a bioassay it is essential to use DC lines with an immature phenotype and function. We have established immortal DC lines as well as long-term growth-factor dependent DC lines with an immortal phenotype that can grow indefinitely in the presence of a conditioned medium. The conditioned medium can be generated by transfecting the GM-CSF gene into NIH-3T3 fibroblasts using retroviral vectors. These cells will produce a low amount (50-100 ng/ml) of GM-CSF which maintain the immature DC phenotype. DC such as the D1 cell line are maintained in vitro indefinitely in standard IMDM medium supplemented with 30% conditioned medium. These immature DC cells are suitable for the establishment of a variety of specific-bioassays to monitor specific activities.

In the example that we report, immature dendritic cells, such as the D1 cells, are perturbed with microbial or viral stimuli in order to regulate gene expression, such as IL-2 gene transcription. Then D1 cells can be treated with test compounds and IL-2 gene expression can be monitored by standard methods such as ELISA, for the detection of IL-2 production in the culture medium. Using this method, cellular, bacterial, or viral targets can be screened. In addition this DC-based bioassays can be used for the screening of vaccinal adjuvants, using the same approach, e.g. induction of IL-2 gene transcription and production.

Finally, from microbial specific DC-based bioassays, global transcriptional profiling analysis can be done using microarray oligonucleotide technology as a screening system, to identify metabolic pathways and gene networks induced by host-pathogen interactions. Using these bio-assays a DC expression database can be generated using a variety of model organisms (wild-types or mutated bacteria e.g. carrying mutations in relevant genes responsible for pathogenicity). Perturbations in the DC gene function system can be generated with bacteria, viruses. Prions, fungi, and parasites. Specific screening of compounds, such as natural products or analogs from natural products can be conducted to generate more data for the integrated DC-expression database which ultimately will predict the effects of tested compounds on DC metabolic pathways and on DC-specific gene networks. Ultimately, the proposed DC-based bioassays will identify sentinel biomarkers genes (signature) for a variety of treatments including infectious diseases but also inflammatory and autoimmune diseases.

Thus, in one embodiment, the invention provides an in vitro method for identifying targets associated with DC perturbation by detecting IL-2 expression in DC cells prior to an following exposure to a perturbation-inducing agent, e.g., microorganisms including bacteria, fungal organisms, viruses (e.g., immunosuppressive viruses), prions and the like. The effect on IL-2 expression may be observed as no effect, inhibition of expression or stimulation of expression. The method further includes contacting the DC cells with a compound or small molecule and detecting the effect on IL-2 expression, thereby affecting directly or indirectly, a target cellular component associated with DC perturbation, e.g., immunostimulation or immunosuppression. In addition, such an assay can be utilized to identify adjuvants useful in vaccine preparations. It should be understood that the invention is not limited to IL-2 as the target cellular component induced or suppressed following DC perturbations. Using the DC cell system described herein, it may be possible to identify other genes or cellular targets indicative of DC perturbation.

The method as described above allows one of skill in the art to identify cellular targets, e.g., transcription factors, pathways, gene clusters, that are associated with immune responses in infectious diseases, inflammatory responses and autoimmune disease, for example.

According to another aspect of the invention, the present invention provides methods useful for screening agents capable of affecting dendritic cell activation or maturation. The method includes incubating in the presence and absence of a test agent, a microbial stimulus and immature dendritic cells, and detecting one or more activities that are specific to dendritic cell activation or maturation in the presence and absence of the test agent. An increase or decrease in the amount of the activities specific to dendritic cell activation or maturation caused by the test agent is indicative of an agent capable of affecting dendritic cell activation or maturation.

The test agents used in the screening methods of the present invention can be any agent to be tested for therapeutic uses. In one embodiment, the test agents are compounds, small molecules, polynucleotides, polypeptides, and any derivatives thereof.

Activities that are specific to dendritic cell activation or maturation include any activity associated specifically with dendritic cell activation or maturation. For example, several activities are specifically associated with dendritic cells upon their encountering of a microbial stimulus and these activities include, without limitation, antigen intake, production of cytokines, activation of lymphocytes such as priming naïve T cells, and expression of cell surface proteins such as MHC-I, MHC-II, CD40, CD54, CD80, and CD86. In one embodiment, IL-2 expression is used as one of the activities specific to dendritic cell activation and is detected in the presence and absence of a test agent.

The present invention also provides an assay system useful for testing an agent's ability to affect dendritic cell maturation. The system includes a container containing a test agent, a microbial stimulus and immature dendritic cells. The system can include one or more containers and can be used directly or in connection with other systems to detect IL-2 expression of dendritic cells in the presence and absence of a test agent and/or collecting data in a computer readable medium. In one embodiment, the system is a high-throughput system.

According to another aspect of the present invention, dendritic cells are targeted by immunosuppressive virus infections, e.g., cytomegalovirus (CMV) or HIV infection. Therefore, another feature of the present invention provides methods of using dendritic cells to screen candidate therapeutic agents for the treatment of immunosuppressive virus infections, e.g., CMV or HIV infection. In one embodiment, immunosuppressive viruses, e.g., CMV or HIV and dendritic cells, e.g., immature dendritic cells such as D1 are incubated in the presence and absence of a test agent and the level of an activity specific for dendritic cell activation is determined. An increase of the level of the activity caused by the test agent is indicative of a candidate therapeutic agent for the treatment of immunosuppressive virus infections, e.g., CMV or HIV infection.

Activities specific for dendritic cell activation include any activity specifically associated with dendritic cells' response upon their encountering of a microbial stimulus. For example, these activities can include, without limitation, antigen intake, production of cytokines, activation of lymphocytes such as priming naïve T cells, response to microbial stimuli, and expression of cell surface proteins such as MHC-I, MHC-II, CD40, CD54, CD80, and CD86. In one embodiment, IL-2 expression is used as one of the activities specific to dendritic cell activation and is detected in the presence and absence of a test agent.

Another feature of the present invention provides methods for treating immunosuppressive virus infections, e.g., CMV or HIV infection or immunosuppression associated with immunosuppressive virus infection in a subject, e.g., a mammal such as human by administering to the subject an effective amount of IL-2 and an activator of dendritic cells. An activator of dendritic cells can be any agent that induces dendritic cell maturation or production of IL-2. For example, an activator of dendritic cells can be an agent activating one or more TLRs in dendritic cells or an agent that mimics T cell help such as CD40 activation by anti-CD40 antibodies in stimulating dendritic cells.

The agents of the present invention useful for therapeutic treatment can be administered alone, in a composition with a suitable pharmaceutical carrier, or in combination with other therapeutic agents. An effective amount of the agents to be administered can be determined on a case-by-case basis. Factors should be considered usually include age, body weight, stage of the condition, other disease conditions, duration of the treatment, and the response to the initial treatment.

Typically, the agents are prepared as an injectable, either as a liquid solution or suspension. However, solid forms suitable for solution in, or suspension in, liquid vehicles prior to injection can also be prepared. The agent can also be formulated into an enteric-coated tablet or gel capsule according to known methods in the art.

The agents of the present invention may be administered in any way which is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The agents may also be directly applied to tissue surfaces, e.g., during surgery. Sustained release administration is also specifically included in the invention, by such means as depot injections or erodible implants.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Dendritic Cell Gene Expression Upon Maturation Stimuli

Dendritic cells (DC) are strong activators of primary T cell responses. Their unique priming ability is acquired upon the encounter of maturation stimuli. In order to identify genes differentially expressed upon maturation induced by exposure to Gram bacteria, a kinetic study of DC gene expression was performed using microarrays representing 11000 genes and expressed sequence tags (ESTs). Approximately 3000 differentially expressed transcripts were identified. Unexpectedly functional interleukin (IL)-2 transcript, giving rise to IL-2 production, was transiently upregulated at early time points following bacterial encounter. In contrast, macrophages did not produce IL-2 upon bacterial stimulation. We have shown that IL-2 represents an additional key molecule conferring unique T cell stimulatory capacity by DC.

Material and Methods

DC, macrophages and culture medium. D1 cells were cultured in IMDM (Sigma, St. Louis, Mo.) containing 10% heat-inactivated fetal bovine serum (GIBCO), 100 IU penicillin, 100 µg/ml streptomycin, 2 mM L-glutamine (all from Sigma), and 50 µM 2-mercaptoethanol (complete IMDM) with 30% supernatant from R1 medium (supernatant from NIH3T3 fibroblasts transfected with GM-CSF). Macrophages and DC were derived from the same bone marrow cells collected from 4 different mice and divided in two separate cultures. mBMDC were obtained after 14 days of bone marrow culture in 30% R1 medium. Macrophages were obtained after 14 days of bone marrow culture in presence of M-CSF. Wild type and DC were derived from mice of the same littermate. mBMDC were used for bacterial activation only if they were immature, as judged by low B7.2 expression and absence of CD40. Cells that showed a partial spontaneous activation were discarded.

Infection with bacteria. $E.$ $coli$ DH5α were grown overnight in LB medium. 100 µl of overnight culture were inoculated in 10 ml of fresh LB and grown for an additional hour at 37° C. Bacteria were added to cell cultures at a MOI of 10. Co-cultures were incubated for 1.5 h. DC or macrophage cultures were washed and supplemented with gentamicin and tetracycline at a final concentration of 50 µg/ml and 30 µg/ml respectively.

Sample preparation and array hybridization. Antisense cRNA was prepared following Affymetrix (Santa Clara, Calif.) recommendations. Briefly, total RNA was extracted from frozen pellets using the Trizol procedure. The Oligotex kit from Qiagen, (Chatsworth, Calif.) was used to purify mRNA. Double-stranded cDNA was retro-transcribed using a modified oligo dT primer with a 5' T7 RNA polymerase promoter sequence and the Superscript Choice System for cDNA synthesis (Life Technologies, Gaithesbourg, Md.). 1 µg of double-stranded cDNA was transcribed to cRNA with the ENZO kit (Affymetrix).

cRNA was purified on an affinity column (RNeasy; Qiagen) and then fragmented to an average size of 50-200 bases, by incubation for 35 min at 94° C. in 40 mM Tris-acetate pH 8.1, 100 mM potassium acetate and 30 mM magnesium acetate. Samples were diluted in the hybridization solution (1M NaCl, 10 mM Tris pH7.6, 0.005% Triton X-100, 0.1 mg/ml herring sperm DNA, BioB-, BioC-, BioD-, cre-control cRNAs at a concentration of 1.5, 5, 25, 100 pM respectively) at a final concentration of 0.05 µml and heated at 94° C. for 5 min.

Analysis of the samples was performed by hybridizing the fragmented cRNAs to the Affymetrix MUL-1K GENE-CHIP® array (i.e., cRNA microarray), consisting of 2 individual chips (called A and B) collectively representing approximately 11000 murine genes and ESTs. Probe array hybridizations were carried out as described32, by placing the samples in the hybridization cartridge at a final volume of 200 µl/chip. Hybridizations were performed under rotation at 45° C. for 16 h.

Following hybridization the chips were rinsed with 6× SSPE-T (0.9M NaCl, 60 mM NaH$_2$PO$_4$, 6 mM EDTA, 0.005%/ Triton X-100 adjusted to pH 7.6)and 0.5× SSPE-T and stained by incubation with 2 µg/ml streptavidin-phycoerythrin (Molecular Probes, Eugene, Oreg.)and 1 mg/ml acetylated BSA (Sigma). The arrays were read at a resolution of 7.5 µm, using a confocal scanner (Affymetrix) and analyzed with the MicroArray Suite 4.0 Gene Expression analysis program (Affymetrix).

PCA analysis. Briefly, we first rewrote our data-set in terms of a matrix in which the 9930 rows represented the genes and ESTs (data observations) and the 14 columns represented the 7 different time points in duplicate (independent variables). The $a_{ij}$-th element of the matrix was the Average Difference, which represents gene expression level14, of the i-th gene at the j-th experimental condition. The method proceeds in a unitary transformation (rotation)of the matrix, which returns two distinct matrices: the eigenvector matrix and the eigenvalue matrix. The columns of the eigenvector matrix are the principal components (PC) of the data set and the rows are the time points in duplicate. The eigenvalues represent the percentage of the overall variance that each component describes. PC1, PC2, PC3 and PC4 together were able to describe more than 98% of the entire variance.

PCR primers and IL-2 ELISA. The sequences of the PCR primer pairs (5' to 3') that were used are as follows:

IL-2, TCCTCACAGTGACCTCAAGTCC (SEQ ID NO. 1) and

TGACAGAAGGCTATCCATCTCC (SEQ ID NO. 2);

β-actin, CATCGTGGGCCGCTCTAGGCAC (SEQ ID NO. 3) and

CCGGCCAGCCAAGTCCAGACGC (SEQ ID NO. 4).

IL-2 ELISA was performed using the DuoSet kit (R and D, Minneapolis, Minn.) and following the manufacturer recommendations.

MLR. 5×105 wild-type and IL-2-'- DC were activated with bacteria and 4-7 h later incubated with 2×106 CFSE-labeled T cells. T cell division was assessed by FACS analysis 48 h or 72 h later. Alternatively graded numbers of bacterial activated DC were incubated with 2×105 T cells and proliferation tested by [$^3$H]thymidine incorporation 72 h later. CD4$^+$ and CD8$^+$ lymphocytes were purified (99% purity) from BALB/c or C57BL/6 mice lymph nodes by negative selection of macrophages, DC, B cells and CD4 or CD8 T cells. These cell populations were eliminated using the MiniMACS columns (Miltenyi Biotec, GmbH) after preincubation with Macl, Cdl lc, B220 and CD4 or CD8 antibodies (all from Pharmingen).

Mice. Pathogen free C57BL/6 and BALB/c mice were obtained from Harlan-Italy. C57BL/6 IL-2-/- animals were kept in pathogen free conditions. All experiments were performed in compliance with the relevant laws and institutional guidelines.

Transcriptional Analysis of Developmentally Synchronized DC

Transcription analysis requires homogeneous populations to avoid dilution and contamination of information. Due to their plasticity, mBMDC are extremely heterogeneous and it is not feasible to obtain homogeneous immature cells without contamination with mature and intermediate DC. We have described a DC culture system that allows the propagation of homogeneous immature growth factor-dependent (granulocyte monocyte colony-stimulating factor) mouse DC that can be fully matured in response to bacteria, bacterial cell products or inflammatory cytokines, mimicking the in vivo DC maturation process. Studies using a well-characterized DC line, D1, obtained using this culture system, show similar maturation as seen in fresh splenic or BMDC.

Figure 1:
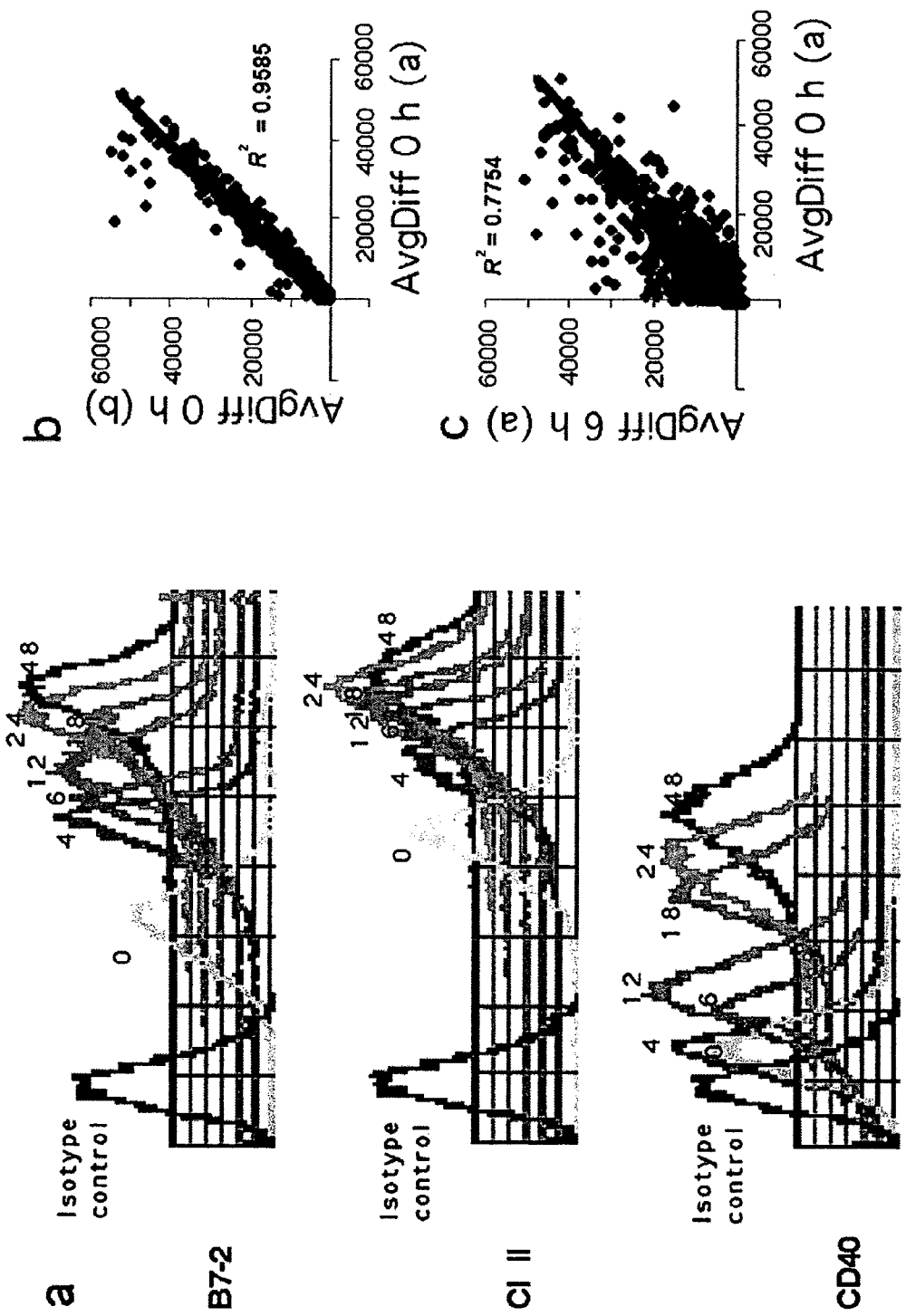
FIGS. 1a to 1c show developmentally synchronized DC.

In the present study, D1 cells were activated with Gram bacteria *Escherichia(E.) coli* and the transcriptional analysis was carried out on immature cells and cells stimulated for 4, 6, 12, 18, 24, 48 h using high-density oligonucleotide arrays displaying probes for 11000 genes and expressed sequence tags (ESTs). At each time point after stimulation, D1 cells were phenotypically characterized for their state of developmental synebronisation by analyzing the level of expression of major histocompatibility complex (MHC)class II, B7.2 and CD40 (FIG. 1). Biotin-labeled CRNA was produced and hybridized onto arrays. To assure the reproducibility of the assay, the entire experiment was performed in duplicate and the gene expression profiles compared (FIG. 1b).

The variability observed never exceeded 5% of the genes and usually affected transcripts at a level of expression close to the lower limit of detection (1.5 pM). Approximately 30% of the genes and ESTs displayed on the array were called present at each time point tested. Excluding genes that always remained below the detection limit during the entire kinetic assay, we obtained 9930 genes that were expressed at least at one time point.

Principal Component Analysis

To get an approximate visualization of our entire data set, without losing experimental information (variance), we first applied the Principal Component Analysis (PCA)method, which allows the dimensionality of complex data to be reduced. Thus we were able to globally describe features of the kinetic points that best explained the corresponding transcriptome (Table 1).

TABLE 1

Results of PCA on the entire data set.

| Independent variables | PC1 (n = 1) | PC2 (n = 2) | PC3 (n = 3) | PC4 (n = 4) |
|---|---|---|---|---|
| 0 h (a) | −0.26 | 0.53 | −0.161 | 0.347 |
| 0 h (b) | −0.252 | 0.643 | −0.337 | −0.228 |
| 4 h (a) | −0.264 | 0.142 | 0.468 | 0.328 |
| 4 h (b) | −0.267 | 0.164 | 0.327 | −0.441 |
| 6 h (a) | −0.268 | −0.017 | 0.36 | 0.186 |
| 6 h (b) | −0.269 | 0.015 | 0.339 | −0.351 |
| 12 h (a) | −0.272 | −0.149 | 0.111 | 0.209 |
| 12 h (b) | −0.273 | −0.163 | 0.043 | −0.121 |
| 18 h (a) | −0.271 | −0.185 | −0.013 | 0.232 |
| 18 h (b) | −0.27 | −0.223 | −0.14 | −0.289 |
| 24 h (a) | −0.268 | −0.229 | −0.246 | 0.093 |
| 24 h (b) | −0.27 | −0.196 | −0.252 | −0.243 |
| 48 h (a) | −0.266 | −0.139 | −0.256 | 0.319 |
| 48 h (b) | −0.271 | −0.121 | −0.259 | −0.036 |

TABLE 1-continued

Results of PCA on the entire data set.

| Independent variables | PC1 (n = 1) | PC2 (n = 2) | PC3 (n = 3) | PC4 (n = 4) |
|---|---|---|---|---|
| Eigenvalue | 0.932 | 0.022 | 0.019 | 0.008 |
| Cumulative (%) | 93.2 | 95.4 | 97.3 | 98.1 |

The values in the columns are the coefficients of the principal component (PC) indicated at the top. The eigenvalues at the bottom express the variance explained by that particular PC (overall variance = 1). The cumulative value is the percentage of information that is described by the first n PCs taken together.

We analyzed only the first four principal components (PC) since they globally explained more than 98% of the overall variance. Although PC1 was able to describe more than 93% of the total variance, it did not contain any kinetic information, as it was simply a measure of the time-independent average expression. Conversely, PC2 and PC3 were two time-dependent parameters. PC2 represented the trend of expression over time, giving a measure of gene down-regulation; PC3 described the shape of this trend, indicating the concavity of the expression curve. PC2 versus PC3 coefficients are plotted in FIG. 2a.

Qualitatively this analysis indicates that, following activation, the general organization of gene expression is immediately influenced. Cells, then, progressively return to gene expression similar to that of immature cells but clearly distinct from it. Thus, there is a notable wave of genes that are transiently modulated during activation in addition to genes permanently expressed in either immature or terminally differentiated cells, that characterize these two stages. The process of DC maturation differentiation stabilized 24 h after activation. PC4, (Table 1), was able to discriminate between two independent replicates, indicating the existence of a systematic experimental error that contributed to the overall variance of less than 1%. Given the systematic nature of the error and the R2 of linear regression in correlation plots (FIG. 1) it was correct to average the replicates and perform the following analysis on the average values.

Gene Clustering

To identify differentially expressed genes inside the collection of 9930 genes and ESTs obtained, we first applied a clustering algorithm, which groups genes according to the similarity of their expression patterns, based on Self-Organizing Maps (SOMs). Mean average differences (AvgDiff, parameter that indicates the level of expression) of the duplicates were utilized and data were filtered to exclude all of the genes or ESTs that showed a fold change between the maximum and minimum kinetic value lower than 3. With this filter, sequences to be clustered were reduced to 2951, about half of which were ESTs (FIG. 2b).

Figure 2:
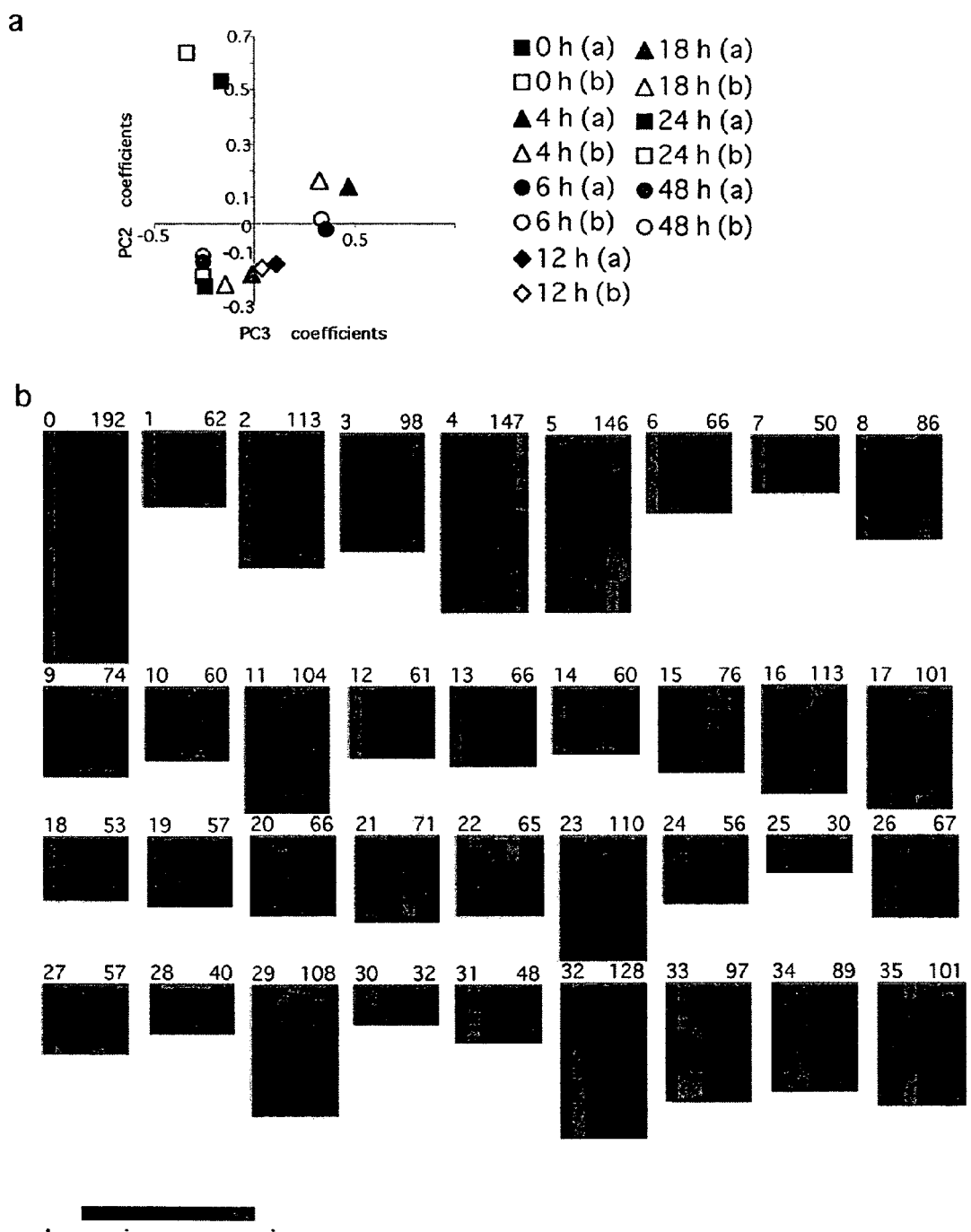
FIGS. 2a and 2b show PCA analysis.

Then, a second clustering method (Hierarchical clustering) was applied to each SOM cluster in order to further investigate smaller profile differences and to verify that all of the sequences were grouped correctly. Using this approach we obtained a good clustering of the genes, with each hierarchical cluster having a correlation coefficient higher than 0.79 (FIG. 2b). Details of FIG. 2 can be found at the www.btbs.unimib.it/DCgenes web site as supplementary information. Different databases (GenBank, SwissProt, Kegg, and Gene Ontology) were automatically queried to classify genes and divide them in functional families, (FIG. 3). As expected, most of the differentially expressed genes encoded transcription factors and signal transduction molecules. They were distributed in different clusters, some transiently induced at different time points and some stably induced or down-regulated.

An example of these genes affected by bacterial induction is shown in FIG. 3. To control the validity of this analysis, we checked, within the different clusters, if well-established markers for DC activation followed the described regulation. For example, inflammatory products, like tumour necrosis factor (TNF)α (cluster 26), macrophage inflammatory protein (MIP)-1α (cluster 23), MIP-1β (cluster 27), MIP-2 (cluster 28) were modulated during the kinetic assay as previously observed in other DC systems. They showed a peak of induction at early time points and were progressively down-regulated towards the end of the kinetic assay, suggesting that the inflammatory activity of DC is mainly elaborated early after activation, before DC have left the inflammatory site (FIG. 3).

Moreover, IL-12p35 was transiently induced during activation (cluster 32, FIG. 2, FIG. 3), with a peak of expression at 4 h. IL-12p35 temporary expression has also been documented in LPS-activated hMDC, but with a delayed kinetic. IL-12p40 mRNA (cluster 17) was strongly up-regulated at early time points after bacterial encounter and down-regulated at later time points (FIG. 2 and FIG. 3). Activation with bacteria induces DC maturation and survival. Anti-apoptotic genes, up-regulated after bacteria encounter, were mouse inhibitor of apoptosis protein (MIAP)-1(cluster 17), MIAP-2 (cluster 11), bcl-x (cluster 22), TNF receptor associated factor (TRAF)1(cluster 23) and TRAF2 (cluster 29).

Conversely, bcl-2 mRNA was already down-regulated 4 h after bacterial stimulation (cluster 0), indicating that it is not involved in maintaining mature-DC survival (FIG. 3). Expression of members of the Vav family and WASp, proteins involved in actin reorganization downstream specific signals, was regulated during maturation (FIG. 3).

Induction of IL-2 Production by DC

We observed that cluster 32 contained the transcript encoding the T cell growth factor IL-2. Bacterial encounter induced transient IL-2 mRNA up-regulation in D1 cells at early time points (4-6 h) after activation (FIG. 4a). We thus tested the hypothesis that this molecule could represent an important co-stimulatory molecule produced by DC. IL-2 expression was validated by semi-quantitative PCR on fresh mBMDC that showed expression kinetics similar to that of D1 cells. Protein secretion was measured by enzyme-linked immunosorbent assay (ELISA). Accumulation of IL-2 in the supernatant was observed between 4 h and 8 h and again between 14 h and 18 h following activation (FIG. 4b).

To test if IL-2 production after bacterial encounter was a DC-specific phenomenon, we performed the same analysis on bone marrow-derived macrophages. After activation with bacteria, supernatants were collected at similar time points and IL-2 was measured. As shown in FIG. 4b, no IL-2 production by macrophages was observed, indicating that, after bacterial activation, IL-2 was specifically induced only in DC.

DC-derived IL-2 Mediates T Cell Activation

The role of IL-2 produced by early bacterial-primed DC in T cell activation was investigated by analyzing the capacity of IL-2-/- and wild-type DC to stimulate alloreactive $CD4^+$ and $CD8^+$ T cells in a primary mixed lymphocyte reaction (MLR) assay. mBMDC were obtained from wild-type and IL-2-'-mice20 and activated with bacteria at a multiplicity of infection (MOI)of 10 (FIG. 1). Wild-type and IL-2-/-DC were equally activated by bacterial stimulation (FIG. 5a) and they did not shown any difference in viability (FIG. 5b).

$CD4^+$ or $CD8^+$ allogeneic T cells were added to early bacterial-primed DC (4-7 h after activation) and DNA synthesis tested by thymidine incorporation after three days of co-culture. As shown in FIG. 5c IL-2-'-DC were severely impaired in the ability to induce T cell proliferation. Moreover T cell division was directly investigated by FACS analysis. $CD4^+$ or $CD8^+$ allogeneic T cells labelled with the cell dye carboxyfluorescein diacetate succinimidyl ester (CFSE) were added to early bacterial-activated wild-type and IL2-/-DC. The number of mBMDC able to induce the maximal T cell proliferation activity, identified in the previous experiment, was used in the present MLR assay. Very few cycling T lymphocytes were observed in IL-2-'-DC cultures (FIG. 5d). This was not due non-specific lack of DC function since IL-2-/-DC were able to activate T cells as judged by the increased number of blast cells expressing the early activation marker CD69 after 48 h of culture (FIG. 5e). No CD69 upregulation was observed on T cells cultured in absence of DC.

Discussion

The entire data set was visualized using the PCA method. In these types of studies PCA allows one to describe and consequently to distinguish a process of cellular activation from a process of cellular differentiation. The activation is a reversible phenomenon: upon exposure to a given stimulus the cells undergo transitional functional and phenotypic modifications and then return to the original state. On the contrary, the differentiation event is an irreversible process that induces a progression toward a new functional state. As the gene expression profile is a major determinant of cellular phenotype and function, PCA applied to cell gene expression pattern in a kinetic study allows one to visualize similarities among different states within the same cell after stimulation.

In the case of DC, as visualized by PCA, the cells undergo differentiation since their gene expression profile reveals a profound reprogramming at early time points, consistent with an activation, but, subsequently, it progresses to a new distinct steady state. As indicated by the PCA the process of DC differentiation is quite rapid. During the 24 h following bacterial encounter DC experience all the transcription modification necessary to progress from immature to mature cells.

As expected, activation with bacteria induced the modulation of many genes involved in cytoskeleton rearrangements, antigen processing, control of migration and apoptosis, and in the regulation of inflammatory responses. In particular, many factors that modulate the dynamic properties of actin filaments were differentially expressed during maturation. These molecules were proteins involved in coupling actin filaments to the cell surface, such as protein of the VASP family, or proteins involved in cross-linking actin filaments, such as fascin, or in severing them, for example gelsolin22. Moreover the Vav proteins that induce typical Rac-1 and RhoG-like cytoskeletal changes including cell spreading, membrane ruffling and the formation of lamellipodia as a consequence of extensive reorganization of F-actin23, were also regulated at the transcription level.

Constitutive, but modulated, expression of the transcript overlapping myelin, the transcript expressed outside the central nervous system, was observed in D1 cells (cluster 23). It is well-established that thymic DC express tissue specific antigens to negatively select auto-reactive T cells. Analogously, peripheral DC expression of sequestered antigens could be a mechanism for maintaining peripheral tolerance.

The most unanticipated finding of this study was that DC produce IL-2 in a tightly regulated time frame. Thus, the adjuvant property of bacteria is explicated by inducing, in DC, not only the up-regulation of co-stimulatory surface proteins and the maximization of the efficiency in presenting antigens, but also by inducing the production of co-stimulatory molecules such as IL-2. This seems to be a unique feature of DC as we have found that macrophages are unable to produce IL-2 upon bacterial activation.

Two waves of IL-2 production by DC following bacterial encounter have been observed. The first wave is between 4 h and 8 h after bacterial uptake and the second wave is between 14 h and 18 h following activation. This timing is compatible with the appearance of MHC class II$^+$ peptide and MHC class I$^+$ peptide complexes at the cell surface. Notably, DC are able to present exogenous captured antigens to CD4 T cells in a few hours while at least 8 h are required to process and present bacterial antigens in association with MHC class I molecules. Thus, early-activated DC are perfectly equipped to prime CD4 T cells, despite their relatively low levels of MHC and membrane-associated co-stimulatory molecules and expression of T cell inhibitory cytokines, such as IL-10. At later time points, IL-2 could represent a key co-stimulatory protein in activating CD8 T cells, even though DC have not yet reached their terminal maturation stage. This data could explain the ability of activated DC to prime CD8 T cell in a CD4-independent manner.

Exogenous sources of IL-2 for induction of T cell proliferation may be also required when the frequency of responder antigen-specific T cells or their affinity for MHC$^+$ peptide complexes is low as it can frequently happen in vivo during immune responses to microorganisms.

Signals induced by TCR and IL-2 are involved in activating and maintaining IL-2Rα transcription that forms, together with β and γ chains, the high affinity IL-2 receptor. The α subunit has been described to be up-regulated in vivo at the surface of specific T cells just 8 h after super-antigen injection. The drastic reduction of IL-2 concentration in the supernatant, between 8 h and 10 h after activation, could be explained by re-uptake of the cytokine by DC expressing the IL-2 receptor. It could be extremely important that the release of IL-2 by DC is efficiently controlled to avoid a bystander activation of unrelated T cells. Secretion of IL-2 could be also necessary to counteract the effect of IL-10 that has been reported to be produced by early-activated DC and that we also found at a high concentration. In absence of IL-2, IL-10 has a well-documented inhibitory function in alloantigen responses.

IL-2 is also thought to activate NK cells in vitro. However, this effect has never been considered relevant in vivo during immunocompetent responses. It was commonly believed that IL-2 was exclusively produced by T cells during the acquired immune response, while the activation of NK cells occurs previously, during the innate response. As DC can produce IL-2 early after activation, this assumption should be revised. It is well established that DC are able to activate NK cell responses in direct NK-DC interactions, thus we believe that IL-2 is relevant and obvious co-stimulatory factor. The finding that DC can produce IL-2 at early time points after bacterial uptake suggests a primary role of DC in the activation of innate responses but also helps explain the unique ability of these cells to prime T lymphocytes. This observation was made more than 20 years ago by Cohn and Steinman but the molecular events responsible for T cell priming were never really understood.

Example 2

Stimulation of IL-2 Production By Dendritic Cells

In the present study we analyze different stimuli for their capacity to induce IL-2 production by DC and the ability of tissue resident immature DC, such as Langerhans cells, to produce IL-2 following activation. We show that only stimuli that are known to bind to TLRs but not inflammatory cytokines are able to induce IL-2 secretion by DC and that IL-2 production is independent from the DC tissue origin. Immature DC from either spleen, bone marrow or skin (Langerhans cells) are, indeed, able to secrete IL-2 following microbial stimuli activation. Interestingly, in early-activated DC interacting with T cells, IL-2 localizes at the site of T cell contact. Finally, here we show that IL-2 production by DC occurs also in vivo following bacterial or LPS injection.

Material and Methods

Antibodies and Reagents. LPS (*E. Coli* 026:B6, used at 10 µg/ml) and zymosan (used at 10 µg/ml) were obtained from Sigma Chem. (St. Louis, Mo.). rTNF, (San Francisco) and rIL-1. (Genzyme, Cambridge Mass.) were used at 100 U/ml and 10 µg/ml respectively. IFN was kindly provided by Schering-Plough (Dardilli, Fr.) and used at 1000 U/ml. CpG (TC-CATGACGTTCCTGATGCT)(SEQ ID NO. 5) and CpG control (TCCATGAGCTTCCTGATGCT) (SEQ ID NO. 6) oligos were purchased from Life Technologies and used at a concentration of 1☐M. PE-conjugated anti-IL-2, PE-conjugated rat Isotype control, biotinilated anti-CD8α and FITC-conjugated anti-CD11c monoclonal antibodies were purchased from Pharmingen. Quantum-red-conjugated streptavidin was obtained from Sigma. Anti-I-A$^d$/I-E$^d$ mAb (clone M5 /114, rat IgG2b) was kindly provided by Dr. A. Ager (NIMR, London, UK). FITC-conjugated anti-rat was from Jackson ImmunoResearch (West Grove, Pa.). Anti-CD40 antibody [clone FGK45 (10)] was used at a concentration of 20 µg/ml and crosslinked with a monoclonal anti-rat antibody (10 µg/ml, PharMingen).

Mice. Pathogen free C57BL/6 and BALB/c mice were obtained from Harlan-Italy or from Iffa Credo (L'arbresle, France) for Langerhans cells preparation and used at 6-10 weeks of age. C57BL/6 and BALB/c RAG2−/− animals were obtained from Centre de Distribution, de Typage et d'Archivage animal (CDTA, Orleans-Cedex, Fr.) and kept in pathogen free conditions. All experiments were performed in compliance with the relevant laws and institutional guidelines.

DC and culture medium. D1 and D8.1 long term DC were cultured in IMDM (Sigma, St. Louis, Mo.) containing 10% heat-inactivated fetal bovine serum (GIBCO), 100 IU penicillin, 100 µg/ml streptomycin, 2 mM L-glutamine (all from Sigma), and 50 µM 2-mercaptoethanol (complete IMDM) with 30% supernatant from R1 medium [supernatant from NIH3T3 fibroblasts transfected with GM-CSF].

Fresh BMDCRAG2−/− were derived from RAG2−/− BALB/c or C57BL/6 bone marrow cells. Usually bone marrow cells cultured for two days and frozen. BMDCRAG2−/− were obtained from defrost cells after 7 days of culture in medium containing 10% of supernatant of GM-CSF transduced B16 tumor cells. BMDCRAG2−/− were used for activation only if they were immature, as judged by low B7.2 and CD40 expression. Cells that showed a partial spontaneous activation were discarded.

IL-2 ELISA. IL-2 ELISA was performed using the DuoSet kit (R and D, Minneapolis, Minn.) and following the manufacturer recommendations.

In vivo analysis of IL-2 production by DC. C57BL/6 mice were transplanted with B16 tumor cells transduced with Flt3 ligand (FLT3L) or GM-CSF (12). After 18 days mice were injected with 50 µg LPS or $10^8$ E. Coli (DH5α) i.p. Three hours after treatment spleens were removed, unicellular suspensions were made and incubated with Brefeldin A (10 µg/ml, Sigma) for 1.5 hours. Cells were fixed with 2% paraformaldehyde, permeabilized with PBS containing 5% FCS and 0.5% saponin and stained with PE-labeled IL-2-specific and FITC-labeled CD11c-specific monoclonal antibodies (PharMingen).

Immunofluorescent labeling of the cells. Staining of DC and T cells was performed as described (13). In brief, DC were plated on coverslips and activated with LPS (10 µg/ml). $CD4^+$ T cells were purified from TCR OVA, DO11.10 BALB/c transgenic mice by negative selection of $B220^+$, $CD8^+$, Mac1+ and $CD11c^+$ cells using Dynabeads (Dynal A. S., Oslo, No) and added to DC, together with the OVA peptide (1 µg/ml) three hours after LPS-activation. After 20 minutes of incubation, cells were washed with phosphate saline buffer (PBS), fixed with 3% paraformaldehyde in PBS and permeabilized with PBS containing 5% FCS and 0.5% saponin. Cells were then labeled with anti-IL-2 and anti-CD11c antibodies for 30 minutes at 4° C.

Infection with bacteria and yeasts. E. Coli DH5α were added to DC at a multiplicity of infection (MOI) of 10. Cocultures were incubated for 1.5 h then washed and supplemented with gentamicin and tetracycline at a final concentration of 50 µg/ml and 30 µg/ml respectively.

For activation with yeasts DC were pulsed with live Saccharomyces cerevisiae for 2 hours before the addition of Amphotericin B (Sigma) at a final concentration of 2.5 µg/ml.

Langerhans cells. Epidermal cells containing 1-3% LC were prepared from ear epidermis by standard trypinization (14). Epidermal cells were incubated at 37° C. in 6-wells tissue culture plate in 3 ml of culture medium (RPMI 1640, supplemented with 10% fetal calf serum, 200 mM L-glutamine and 20 µg/ml gentamicin) (Gibco Laboratories). After 12 h incubation, epidermal cells were stimulated with LPS (10 µg/ml) and Brefeldin A was immediately added. As negative control, cells were pretreated with cyclosporin A 1 h before stimulation.

After 6 h stimulation, epidermal cells were double stained with anti-I-$A^d$/I-$E^d$ mAb (clone M5/114, rat IgG2b) followed by FITC-conjugated anti-rat Ab and PE-conjugated anti-IL-2 mAb. For the detection of intracellular antigens, cells were subjected to fixation with 2% paraformaldehyde and permeabilization with 0.1% saponin, 1% BSA in PBS after surface immunostaining.

IL-2 production by DC is induced by microbial stimuli but not by inflammatory cytokines DC express a variety of functional TLRs that, once activated, transduce signals inside the cells leading to the induction of genes, such as inflammatory cytokines, chemokines and costimulatory molecules, involved in the defense against invading pathogens. In order to investigate if the activation of different TLRs could induce IL-2 production, mouse DC were stimulated in vitro with LPS, a component of Gram-negative bacteria, and lipoteichoic acid (LTA), a component of Gram-positive bacteria that signal through TLR4, oligo DNA containing the unmethylated CpG motif of bacterial DNA that is recognized by TLR9, zymosan, yeast cell wall particles, and peptiglycan (PGN) from Gram-positive bacteria that are recognized by TLR2.

Two long-term growth factor dependent (GM-CSF) mouse DC lines, one derived from spleen (D1) and one derived from bone marrow (D8), were used. To exclude that DC culture conditions (see Materials and Methods) could influence the results, short-term bone marrow-derived DC, BMDC/RAG2−/−, differentiated in vitro in presence of a source of GM-CSF different from the one employed for long term DC lines (see Material and Methods) were also used.

As shown in FIG. 6, all of the microbial stimuli were able to induce IL-2 production by DC. In general, a larger amount of IL-2 was produced by fresh BMDC/RAG2−/− when compared to long-term DC lines, most likely because they have a lower threshold of activation. The only exception was zymosan that resulted a very efficient stimulus in inducing IL-2 secretion by both long- and short-term DC lines. In agreement with this, the best stimulus for IL-2 production by DC was represented by live yeasts (FIG. 6). CpG and PGN were also efficient in stimulating DC to secrete IL-2. A difference between splenic (D1) and bone marrow-derived DC (BMDC/RAG2−/− and D8 cells) was found in the ability to respond to LTA. Only splenic DC efficiently secreted IL-2 upon LTA-stimulation while BMDC/RAG2−/− and D8 cells produced only a measurable but limited IL-2 amount.

Three different inflammatory cytokines, TNFα, IL-1 β and INFα, were then tested for their ability to stimulate DC to produce IL-2. TNFα was selected since it is commonly employed to activate immature DC and to generate in vitro large amount of DC for cell-based therapies of cancer. IL-1β has been used since its intracellular signaling pathway partially overlaps with the one of LPS and IFNα was used because it has been described as a good stimulus for DC activation. In contrast to what observed for microbial stimuli, none of the inflammatory cytokines, used individually or added simultaneously to DC cultures, were able to promote IL-2 secretion by splenic or bone marrow-derived DC. Thus, DC produce IL-2 early after contact with a pathogen or its products regardless of their tissue origin but not in response to specific inflammatory cytokines.

Phagocytosis per se is not sufficient to induce IL-2 production by DC

To investigate if the phagocytic process per se could activate DC in terms of IL-2 production, DC were incubated with inert latex beads or Gram-negative bacteria E. Coli DH5α as control and IL-2 measured in culture supernatant. Our results demonstrated that inert latex beads alone were not able to induce IL-2 production in both splenic or bone marrow DC, confirming the previous observation that microbial stimuli are necessary for this process.

T cell-mediated stimuli induce IL-2 secretion by DC.

IL-2 secretion by DC could also be induced by stimuli that mimic T cell help, such as activation of CD40 by anti-CD40 antibody. Activation of CD40 was a stimulus as efficient as microbial stimuli in inducing IL-2 production by D1 cells. In contrast, in BMDCRAG2−/− cultures little amount of IL-2 could be detected in the supernatant at early time points following CD40 stimulation. This could be due to the fact that fresh immature BMDCRAG2−/− express, at the cell surface, less CD40 (almost undetectable by cytofluorimetric analysis) than D1 line. If DC were first treated with LPS for 12 hours and then subjected to CD40-activation a second late phase of IL-2 production could be induced, indicating that, early after activation with microbial stimuli, DC are not refractory to further stimulation.

IL-2 production by DC is not restricted to lymphoid tissues.

To test whether DC derived from non-lymphoid tissues could produce IL-2 upon stimulation, Langerhans cells, prepared by trypsinization from murine epidermal sheets, were stimulated with LPS and 6 h later IL-2 production was analyzed by flow cytometry. Our data showed that a very limited number of unstimulated Langerhans cells (MHC class II positive cells) were IL-2 positive. This number strongly increased following LPS stimulation. To verify the specificity of IL-2 production, epidermal cells were treated with cyclosporin A (CsA) before LPS stimulation. CsA strongly reduces IL-2 production by DC following LPS encounter. After CsA treatment, the number of IL-2 producing Langerhans cells was reduced in comparison to untreated cells.

DC produce IL-2 following bacterial or LPS injection in vivo.

We, then, investigated if the ability to produce IL-2 was a general DC property shared also by DC in vivo or a sole feature of in vitro differentiating cells. For this purpose, mice were transplanted with GM-CSF or FLT3L transduced tumors to expand $CD8\alpha^-CD11c^+$ or $CD8\alpha^+CD11c^+$ splenic DC populations respectively (21) and injected intra peritoneum with LPS or $E.\ Coli$ DH5$\alpha$ to prime DC. The presence of IL-2-expressing $CD11c^+$ DC in spleens of LPS- or bacterial-treated mice was revealed by cytofluorimetric analysis.

Three hours after bacterial- or LPS-treatment an IL-2-positive CD8 □⁻ $CD11c^+$ DC population was apparent in GM-CSF-treated mice. The possibility that the IL-2-positive cells were, in fact, T lymphocytes that formed doublets with DC, was excluded by performing an immunocytochemistry analysis of splenic single cell suspensions stained with anti-IL-2 and anti-CD11c antibodies. IL-2-positive cells expressed CD11c, indicating that IL-2 producing cells were, indeed, DC. The same analysis was performed on FLT-3L treated mice. After LPS injection around 19% of CD8 $\alpha^+CD11c^+$ cells produced IL-2. Immunocytochemistry analysis confirmed that IL-2-expressing cells were also CD11c-positive. Some IL-2-positive DC were visible already two hours after activation, though the peak was at three hours, and disappeared after six hours in both GM-CSF and FLT-3L treated mice.

In early-activated DC IL-2 localizes at the interface between DC-T cell interaction.

Naïve T cell priming needs prolonged T cell receptor stimulation that is achieved by the formation of an immunological synapse, a specialized molecular organization that takes place at the contact region between DC and T cells. The DC expression of high levels of costimulatory molecules and MHC-peptide complexes and the secretion of cytokines are at the origin of the high efficiency of DC as APCs. As IL-2 is an additional molecule conferring DC the unique naïve T cell stimulatory capacity, it has been investigated if IL-2 produced by early-activated DC is recruited at the contact region between interacting DC and T cells.

LPS-activated BMDC/RAG2−/− were loaded with OVA-peptide, incubated with $CD4^+$ T cells from DO.11.10 transgenic animals for 20 minutes and then stained with anti-CD11c and anti-IL-2 antibodies. IL-2 produced by DC prevalently localized at the interface between DC and T cells, confirming the relevance of DC-derived IL-2 in the process of T cell activation.

Discussion

Unique feature of DC is their ability to activate NK, B and T cell responses. While mechanisms responsible of NK and B cell activation by DC are mostly unknown, activation of T cells by DC depends on many factors such as the efficiency of processing machinery, the high levels of expression of costimulatory molecules and peptide-MHC complexes and the production of polarizing cytokines. Recently, our demonstration that DC produce IL-2 early after bacterial stimulation has opened new possibilities in understanding interactions of DC with T cells and, probably, also with NK and B cells. Thus, it was important to define the stimuli that induce IL-2 secretion by DC in vitro and the ability of DC to produce IL-2 in vivo.

DC were able to secrete IL-2 if activated with microbial cell products that signal through different TLRs. Thus, stimulation of TLRs on DC provokes not only a late upregulation of costimulatory molecules important for adaptive immune response activation but also an early production of IL-2, which may be involved in sustaining both innate NK and adaptive T cell responses. In contrast, none of the inflammatory cytokines examined were able to induce IL-2 secretion by DC indicating that these cells can distinguish between a cytokine-mediated inflammatory process and the actual presence of an infection. Therefore, IL-2 production by DC can presumably occur only during the early phases of an infection when microorganisms or microbial cell products are in fact present and not during the late phases of the inflammatory response, when microbes have been eliminated and inflammation is sustained by cytokines. DC were not able to secrete IL-2 even after IL-1β interaction, although IL-1 receptor (IL-1R), TLR4, TLR2 and TLR9 share several signaling components.

The fact that cytokines were not capable to stimulate IL-2 production by DC is in agreement with the evidences that the quality of the stimulus influences the DC maturation process and that inflammatory cytokines are not able to drive DC to a level of maturation suitable for efficient priming of T cell responses (24). In fact, it has been shown that DC matured in presence of TNF-α are rather tolerogenic.

Yeasts and zymosan, particles of yeast cell wall, were the most efficient stimuli for the induction of IL-2 secretion by DC. The massive production of IL-2 by DC following yeasts and zymosan encounter could explain why yeasts act as potent adjuvant, augmenting the ability of DC to prime $CD4^+$ and $CD8^+$ T cells and to induce protective anti-tumor immunity upon adoptive transfer in vivo.

DC-derived IL-2 induced by TLRs activation could be required to efficiently prime innate NK and acquired T cell responses to fight infections. The role of DC-derived IL-2 in T cell priming is supported by the fact that immunosuppressive viruses, such as cytomegalovirus (MCMV), that establish persistent infections, block IL-2 production by activated DC and affect the capacity of DC to activate T cells (27). Among APCs only DC and not macrophages are able to produce IL-2 following bacterial encounter.

Exogenous sources of IL-2 may be important, for effective T cell priming, when the frequency of antigen-specific T cells or their T cell receptor (TCR) affinity for peptide+MHC complexes is low. This could frequently happen in vivo during immune responses to microorganisms. Indeed, T cells able to mount a specific response are rare and carry different TCRs with heterogeneous affinities. Moreover, as DC display at the surface thousand of different peptides derived from the processing of entire microorganisms, the amount of a particular peptide-MHC complex that can be recognized by a given T cell may be extremely reduced. Thus, in this context, exogenous IL-2 may represent an important costimulatory molecule to help T cell proliferation by activating and maintaining the expression of IL-2Rα chain.

It is commonly believed that DC acquire the ability to prime naïve T cell responses late after activation when they express maximal levels of peptide+MHC complexes and costimulatory molecules. Nevertheless, the early kinetic of IL-2 production makes DC able to prime T cells almost immediately after microorganism encounter. This is in agreement with the observation that in vivo the first signs of naïve CD4⁺ T cell priming by DC can be detected within one or two hours following antigen administration.

Another role of IL-2 produced by DC could be the homeostatic maintenance of regulatory T cells that express high levels of high affinity IL-2 receptor and proliferate in response to IL-2 but are not able to produce it. In fact, it is quite clear that IL-2 and costimulatory molecules play an important role in the homeostasis of regulatory T cells as this population is strongly reduced in IL-2−/−, CD28−/−, CD40−/− and B7−/− mice. Thus, in the gastrointestinal tract CD4⁺ CD25⁺ regulatory T cells could survive by interacting with IL-2 producing and costimulatory molecules expressing DC that have been recently activated by LPS or LTA derived from the commensal flora.

It has been described that DC acquire the ability to directly prime CD8⁺ T cell responses after encounter of antigen-specific CD4⁺ T cells. The mechanism proposed to explain this phenomenon is the activation of DC though CD40-CD40L. IL-2 produced by DC after CD40 activation could be the key molecule that help CD8⁺ T cell priming. This may be true for both non-activated and LPS-matured DC, as CD40-stimulation induced IL-2 production by immature DC and also a second late phase of IL-2 secretion by LPS-activated DC. Interestingly, when early-activated DC interact with T cells IL-2 is recruited at the site of contact, suggesting that secretion of IL-2 by DC is well controlled. This could be necessary to avoid a bystander activation of unrelated T cells.

Different subsets of DC were able to produce IL-2. Tissue resident Langerhans cells as well as CD8 α⁺ and CD8 α⁻CD11c⁺ splenic DC became IL-2 positive following LPS-stimulation. CD8α⁺ and CD8α⁻CD11c⁺ DC are equally efficient in activating T cell responses and, consistently, both populations are able to produce IL-2 following LPS or bacterial activation.

IL-2 production by Langerhans cells could be important for early NK cell activation in peripheral tissues. This process may be relevant to promote macrophage activation and to sustain inflammation as activated NK cells produce large amount of IFNα. Taken together, these observations suggest a molecular mechanism to explain the DC central role in priming both early and late immune responses. DC-derived IL-2 could be a key factor regulating and linking innate and adaptive immunity.

Example 3

Dendritic Cell as a Target for CMV Infection

In this study, we demonstrate that DC are permissive to murine CMV (MCMV) infection. More importantly, infection of DC prevents subsequent delivery of the danger signals required for activation of T cell responses. This study provides the first evidence that CMV-mediated impairment of DC function may be crucial in inducing the immunosuppression that follows infection with this pathogen and implicates IL-2 as a-key factor.

Material and Methods

Animals. Inbred C57BL/6 ($H2^b$, I-$A^b$) and BALB/c ($H2^d$, I-$A^d$) mice of 6 weeks of age were obtained from the Animal Resources Center (Perth, Western Australia) and maintained in specific pathogen free conditions at the Animal Services Facility of the University of Western Australia. All animal experimentation was performed with the approval of the Animal Ethics and Experimentation Committee of the University of Western Australia and according to the guidelines of the National Health and Medical Research Council of Australia.

Cell lines and reagents. Mouse embryonic fibroblasts (MEFs) were cultured in minimal essential medium (MEM-Gibco Life Sciences, Sydney, Australia) supplemented with neonatal calf serum (NCS-Gibco Life Sciences, Sydney, Australia). The D1 cells were maintained as previously described. D1 cells or purified DC were cultured in complete Iscoves modified Dulbeccos medium (IMDM-Sigma Aldrich, St. Louis, Mo.) containing 10% heat inactivated fetal bovine serum (FBS-Gibco Life Sciences, Sydney, Australia); 100 IU/ml penicillin and 100 μg/ml streptomycin (Pharmacia and Upjohn, Sydney, Australia); 2 mM L-glutamine and 50 μM 2-mercaptoethanol and supplemented with 30% conditioned medium containing 10-20 ng/ml GM-CSF (complete IMDM-10). All media for DC suspension and isolation were iso-osmotic with mouse serum. Initial tissue digestion was performed in IMDM buffered with pH7.2 HEPES and supplemented with 2% FBS (IMDM-2). To avoid re-association of DC and T cells during washing and labeling a divalent metal free solution was used. Density separation of DC was achieved using a Nycodenz (Nycomed Pharma AS, Oslo, Norway) gradient, as previously described.

Preparation and purification of MCMV stocks. Monolayers of confluent MEFs were infected with MCMV salivary gland passaged stocks at a multiplicity of infection (MOI) of 0.05 for 1 h at 37° C. Cells were monitored daily for evidence of cytopathic effect (cpe) and the supernatant removed when 100% cpe was observed. The suspension was progressively filtered through 0.8 and 0.45 micron filters and centrifuged at 35 000×g for 2 h at 4° C. in a JA-20 rotor. The viral pellet was resuspended in ice-cold IMDM aliquoted and stored at −180° C. Viral titers were determined on MEFs, as described.

Infection of dendritic cells and MEFs with MCMV

Single Step Growth Curve

For the infection studies, MEFs were grown to confluence while D1 cells were infected on the day of passage. Purified CD11c⁺ cells (DC) were infected immediately following sorting. For infection of MEFs virus was added to the confluent monolayer at an MO1>3 and absorbed for 1 h at 37° C. Residual inoculum was removed after 1 h and the cells treated with citrate buffer (40 mM citric acid, 10 mM KCl, 135 mM NaCl pH3.0) for 1 min at RT to remove reversibly bound virus. Cells were then washed thoroughly, fresh MEM/2% NCS added and the cells incubated for various times before freezing at −70° C.

For infection of immature D1 cells or DC the total number of cells to be infected was resuspended in complete IMDM-10 to which virus (MOI>3) was added. DC plus MCMV inoculum were incubated for 1 h at 37° C. prior to centrifugation at 200×g. The pellet was then resuspended in Citrate buffer and washed extensively with complete IMDM-10. Cells were resuspended in complete IMDM-10 and $10^4$ cells aliquoted per well of a 96 well tray (Corning Glass Works, Corning, N.Y.). DC cultures were sampled at equivalent times to MEFs. Titers at the sample times were determined as previously described.

Multi-step Growth Curve

Multistep growth curves were determined as described above, except that the MOI was reduced to 0.02. For infection of mature D1 cells, LPS (*E. coli* 026:B 6 from Sigma) (10 μg/ml) was added to D1 cells 2 days before infection.

Expansion of CD11c⁺ cells by Flt3L. To expand DC, C57BL/6 mice were treated with Flt3 Ligand (Flt3L) as described. Briefly mice received once daily i.p. injections of 10 μg of Flt3-L in sterile HBSS for 9 days. FLt3L was kindly supplied by Immunex, Seattle, USA.

Injection of mice with MCMV or LPS. BALB/c mice were infected i.p. with $10^4$ pfu of MCMV-K181-Perth or MCMV-K181-LacZ, kindly provided by Dr H Farrell, in PBS/0.05% FBS. Control mice received PBS/0.05% FBS. LPS (30 μg/ml) diluted in PBS was injected i.v. into BALB/c mice; control mice received PBS only. At appropriate times the mice were sacrificed and their spleens removed for the isolation of DC.

Isolation of DC from mice. Single cell suspensions were prepared following the method described by Vremec et al., (2000) with modifications. Spleens were injected with modified IMDM-2 containing collagenase (1mg/ml; type II; Sigma) and Dnase I (Boehringer Mannheim, Germany), cut into small fragments and digested for 25 min at room temperature (22° C.). To disrupt DC-T cell complexes, EDTA was added at a concentration of 0.01 M and incubation continued for 5 min. Undigested material was removed by filtration through a stainless steel sieve. Cells were recovered centrifugation, resuspended in a 1.077 g/cm$^3$ iso-osmotic Accudenz solution, centrifuged at 1700×g for 15 min at 4° C. and the low density fraction collected. The low-density cells were diluted in EDTA-SS and recovered by centrifugation. Cells were then incubated with the appropriate monoclonal antibodies for sorting or analysis.

Phenotypic characterization of DC. Control, LPS-activated and MCMV-infected D1 cells or fresh DC were collected at appropriate time points. Aliquots of cells (1×10$^6$/sample) were preincubated on ice for 30 min with EDTA-SS-FCS containing 10% normal goat serum (NGS). Cells were then incubated with anti-CD11c (HL3), used as a FITC or biotinylated conjugate and anti-class II MHC (TIB-120) detected with $F_{ab}{}^2$-Cy5 conjugated goat anti-rat mAb (Jackson Immunoresearch Laboratories, West Grove, Pa.) or as a FITC conjugate (39-10-8). CD11c staining alone was used where DC were to be used for stimulating T cells, to avoid blocking class II MHC. Other mAb were used as follows: anti-CD11b-PE (M1/70); anti-CD54-FITC (3E2); anti-CD40-FITC (HM40-3); anti-CD86-PE (GLI); anti-CD80-biotin (16-10A1); anti-class I MHC (TIB-126)used purified.

The second step stain were was PE-streptavidin (Pharmingen, San Diego, Calif.) for the biotin-conjugated mAb, and $F_{ab}{}^2$-Cy$^5$ conjugated goat anti-rat mAb for the purified MHC-I. Anti-class I MHC (M1/42.3.9.8) and anti-class II MHC (m5/114.15.2) hybridomas were kindly provided by Dr A Scalzo. All other mAb were purchased from Pharmingen (San Diego, Calif.). Cells infected with MCMV-K181-LacZ were detected by addition of fluorescein di-β-D-galactopyranoside (FDG) (Molecular Probes, Eugene, Oreg.) for 1 min at 37° C. The percentage of MCMV-infected DC was determined by subtracting the fluorescence of DC from mock-infected animals. Infected DC were then defined as 95% of the population which remained following. Propidium iodide (PI) was incorporated into the final wash at 1 μg/ml to exclude dead cells. For apoptosis detection cells were incubated for 15 min in the presence of annexin-V-FITC (Boehringer Mannheim, Mannheim, Germany) and PI. Numbers of apoptotic cells were determined by analyzing the frequency of annexin-V$^+$ PI$^-$ cells within the DC population.

Flow cytometric analysis and sorting of DC. The fluorescence-labeled DC preparations were analyzed on a FACSCALIBUR® (i.e., fluorescence activated cell sorter, Becton Dickinson, San Jose, Calif.). The channels used were: FL1 for FITC, FL2 for PE, FL4 for Cy5 and FL3 to exclude PI-positive cells. Appropriately stained controls were used to check compensation for all fluorochromes used. Files of 2-5× 10$^4$ DC (CD11c$^{high}$/MHC-II$^{high}$, PI negative) events were collected and analyzed on Cell Quest software (Becton Dickinson, San Jose, Calif.). High speed sorting was performed with TURBOSORT® (i.e., optional fluidic, electronic, and drop deflection modification of fluorescence activated cell sorter, Becton Dickinson) on a FACSVANTAGE® (i.e., fluorescence activated cell sorter, Becton Dickinson, San Jose, Calif.) instrument at a sheath pressure of 18 PSI with a 70 μm nozzle. The FL3 and FL2 channels were used to exclude PI positive cells and detect PE-CD11 c$^{high}$ DC respectively. Cells were collected into 70% FBS supplemented with 30% conditioned medium and routinely contained >97% pure DC. Viability after sorting (normally >98%) was determined by trypan blue exclusion.

Endocytosis. FITC-dextran (FITC-DX 40,000 Dalton) was purchased from Molecular Probes (Oregon, USA). Groups of mice (8) untreated, LPS-treated or infected with MCMV for the appropriate time were injected with 0.1 mg FITC-DX. One hour later DC were isolated from spleens and single cell suspensions prepared as described above. Isolated splenocytes were labeled with CD11c and MHC-II antibodies and analyzed by flow cytometry. D1 cells were grown in the presence or absence of 10 μg/ml LPS or infected with MCMV (MOI>3). At appropriate times, cells were incubated at 37° C. or at 4° C. with 0.5 mg/ml FITC-DX for 1 h. Uptake was stopped by addition of ice-cold FACS® buffer (i.e., DPBS +0.1% NaN$_3$+2% FBS). Cells were washed and analysed using a FACSCALIBUR® (i.e., fluorescence activated cell sorter, Becton Dickinson, San Jose, Calif.). Cell surface binding of FITC-DX at 4° C. was subtracted from the uptake values obtained at 37° C. to give the values for true uptake.

Quantitation of IL-12 and IL-2 by ELISA. IL-12 production by D1 was measured by sampling supernatant from MCMV infected, LPS matured (10 μg/ml) or immature D1 at indicated times. IL-12 production by splenic DC was determined by culturing enriched DC for 18 hours with 10 μg/ml LPS and 100 U/ml IL-4 as previously described. IL-12 p40/p70 in the supernatant was detected using C15.6 (capture) and C17.8 biotin-conjugated rat anti-mouse (detection) antibodies (Pharmingen). IL-2 production by D1 was measured by sampling supernatants from immature D1, LPS treated D1 or MCMV infected D1 treated with LPS. Capture (JES6-1A12) and detection (JES6-5H4: biotin-conjugated rat anti-mouse IL-2) antibodies (Pharmingen) were used according to the manufacturer's recommendation. In both assays detection was achieved with poly-horse radish peroxidase (poly-HRP) conjugated to streptavidin (CLB, Amsterdam, Netherlands) and K-Blue (Elisa Systems, Brisbane, Australia). Absorbance was read at 450 nm with an automated ELISA reader (SpectraMAX 250; Molecular Devices, Sunnyvale, Calif.). The detection limit for both assays was 3 pg/ml.

Mixed Leukocyte Reaction Assay. A primary allogeneic MLR was performed using immature, mature (10 μg/ml LPS) or MCMV-infected D1. Alternatively DC were purified from the spleens of MCMV-infected or control BALB/c mice. Stimulators were treated with Mitomycin C (50 μM/ml, 20 min at 37° C.; Sigma) and co-cultured with 10$^5$ allogeneic splenocytes/well in 200 μl of complete IMDM. Cultures were pulsed with 1 μCi/well of [$^3$H]thymidine on day 3 (specific activity 2.0 Ci/mmol; Amersham, Amersham Place, UK). Incorporation of [$^3$H]thymidine was measured 18 h later in a liquid scintillation counter (TopCount NXT). Mean cpm from triplicate cultures are shown in the Figures. In the D1 assays the stimulators are on a C57BL/6 background, hence the responders were generated from allogeneic BALB/c splenocytes. Stimulators derived from MCMV-infected BALB/c mice were used with allogeneic C57BL/6 splenocytes.

MCMV Infects and Productively Replicates in Dendritic Cell Cultures

Given the central role played by DC in initiation and regulation of immune responses, we examined their susceptibility to infection and their ability to sustain productive MCMV replication. Our initial analysis, using the D1 culture system, specifically allowed us to assess the relevance of the DC maturation state in relation to MCMV replication. Infection of immature D1 cells, or standard mouse embryonic fibroblasts (MEF) cultures, at a high multiplicity of infection (MOI) (>3 pfu/cell) resulted in viral production; however, viral production in D1 cells was slower than in MEF (FIG. 7a). Following infection of MEF, virus progeny is released at 18 h post-infection (FIG. 7a). In contrast, in D1 cells, infectious virus was not detected until 27 h post-infection and titers of virus increased over a period of 4 days post-infection, eventually exceeding the levels produced by MEF.

To confirm that infection of D1 cells produced infectious virus, immature DC and MEFs were infected with a low MOI (0.02 pfu/cell). Infectious virus was produced in MEFs until 100% cytopathic effect (cpe) was observed at day 6 post-infection (FIG. 7a). A slower rate of viral production was again observed following infection of D1 cells (approximately 24 h slower than MEF) and again viral titers were observed to increase over time to eventually reach levels exceeding those observed in infected MEF (FIG. 7a).

To determine whether the maturation status of DC was relevant to MCMV infection and replication, LPS-activated D1 cells were infected as above (MOI=0.02 pfu/cell). Maturation of D1 cells was induced by stimulation with LPS for 48 h and the maturation status of the cultures confirmed prior to infection with MCMV by up-regulation of MHC-I/II, CD40, CD80 and CD86, as described previously. When LPS-activated D1 cells were infected with a low MOI, virus replication was observed, however the yield of productive virus was significantly reduced in comparison to infection of immature D1 cultures (FIG. 7a).

Infection of DC was confirmed using ex vivo-derived cells purified from the spleens of Flt3L treated mice. When the Flt3L-derived DC were infected with MCMV at a high MOI, we observed viral production similar to that obtained after infection of LPS-activated D1 cells. This would be expected since it is known that DC acquire an activated phenotype during the process of harvesting and sorting. Thus, MCMV is capable of infecting immature, and to a lesser extent mature DC, and infection leads to the production of high titres of virus. No significant differences were observed in the viability of DC post-MCMV infection, as-assessed by propidium iodide (PI)and annexin-V staining. In cultures tested every second day, out to day 8 after MCMV infection (low MOI), the percentage of viable cells remained>80% (85.25±4.66%), comparable with that observed for uninfected cultures (87%).

MCMV Infects Dendritic Cells in vivo

Having demonstrated that DC can be infected in vitro, it was important to determine what role they play in the context of an infection in vivo. To establish whether MCMV could infect DC in vivo we utilized a recombinant virus expressing the LacZ gene product. Expression of LacZ results from the stable insertion of a LacZ cassette in the intron of the M33 ORF. This insertion has previously been shown to result in stable expression of LacZ in the context of infection, with the expression having no deleterious effects on viral replication. Using FDG, as a substrate for the LacZ gene product β-galactosidase, it was possible to detect MCMV-infected cells by fluorescence analysis (FIG. 7b). The percentage of infected DC during the course of infection was determined after labeling with CD11c, MHC-II and FDG. Splenic DC became MCMV positive (10.10±4.21%) 24 h post-infection, with the majority becoming infected by day 2 (74.61±6.22%).

In accordance with the in vitro analysis, MCMV did not alter the overall viability of DC recovered from the spleens of MCMV-infected animals. Greater than 77% of splenic DC were viable at days 1, 2 and 4 post-MCMV infection, compared with 80% viability in DC from mock-infected mice and 65% in DC from mice infected with LPS for 2 days.

MCMV Affects the Endocytic Capacity of DC

The maturation of DC from immature antigen processing cells to mature antigen presenting cells is associated with a reduced capacity for endocytosis. The endocytic capacity of MCMV-infected D1 cells was compared to that of immature or LPS stimulated D1 cells by measuring uptake of fluorescin-conjugated-dextran (FITC-DX). Two days post-infection, a 50% reduction in uptake was detected in MCMV-infected cells relative to immature D1 cells (FIG. 8a), while complete inhibition was observed at 4 days post-infection (FIG. 8a).

The effect of in vivo MCMV infection on the functional endocytic capacity of spleen-derived DC was also tested. Enriched DC obtained from the spleens of control mice exhibited a high endocytic capacity, while DC from spleens of LPS-treated or MCMV-infected mice were less efficient at antigen uptake (FIG. 8b). Confirmation that FITC-DX was endocytosed, as opposed to it adhering to the cell surface, was obtained by fluorescence microscopy.

MCMV Infection Interferes with Phenotypic Activation of DC

Having established that MCMV can productively infect DC, it was important to determine the effects of such infection with respect to the phenotype of these cells. Initial analysis was undertaken using the D1 system. D1 cells express CD11c, CD11b and CD54, as well as MHC class I and II, CD40, CD80 and CD86. Post-infection of immature D1 cells with MCMV (MOI>3), two stages of phenotypic change were observed. At day 2 post-infection the levels of MHC class I and II, CD40, CD54 and CD86 were increased to levels similar to those observed following LPS activation (FIG. 9a). Interestingly, the levels of CD80 remained unchanged. When the same antigens were analyzed at 4 days pi, decreases in the expression of all markers tested were observed (FIG. 9b), with the most profound effects occurring for MHC class II.

To ensure that the down-regulation of adhesion, homing, MHC and co-stimulatory molecules observed following MCMV infection of D1 cells was not an artifact of this culture system, the effects of infection were tested using ex vivo purified splenic DC. In these experiments, expression of MHC-II, CD40, CD80, CD86 and CD54 was reduced at 2 and 4 days postinfection, as compared to untreated or LPS treated controls (FIG. 10). A reduction in MHC-I expression was only observed at day 4 post-infection (FIG. 10b). In these experiments the LPS mediated phenotypic maturation was marginal since the DC were partially activated during the extraction/purification protocol.

Ultimately, the effect of MCMV was tested in vivo by analysis of the phenotypic changes that occurred in DC from the spleens of MCMV-infected animals during the course of infection. Analysis of in vivo derived DC identified two populations of CD11c+/MHC-II+ cells in the spleens of mice infected with MCMV. A CD11c$^{high}$/MHC-II$^{high}$ population found in control animals was present in MCMV-infected mice until day 2 pi, but was no longer detectable at day 4 post-infection (FIG. 11a).

A second population of DC, characterized by a $CD11c^{int}$/$MHC-II^{dim}$ phenotype was detected in splenocytes from MCMV-infected animals at day 2 post-infection and reached maximal numbers at day 4 post-infection (FIG. 11a). This population of cells, which will hereafter be referred to as virally altered DC (vDC), was not detected in either mock-infected (FIG. 11a) or LPS (18 h) treated mice. In vitro culture of $CD11c^{high}$/$MHC-II^{high}$ cells isolated from MCMV-infected mice at 2 days post-infection showed that the vDC population arises from these classic DC. Phenotypic analysis of MCMV-infected ($FDG^+$) DC 2 days post-infection showed increased expression of CD40 and CD86, comparable to the expression observed post-LPS stimulation (FIG. 11b). In contrast, 4 days post-infection, infected ($FDG^+$) DC showed a severely reduced expression of MHC-II, CD40 and CD80 as well as reduced expression of CD54, MHC-I and CD86 (FIG. 11c). CD86 levels, increased significantly at day 2, were by comparison markedly reduced at day 4 post-infection.

MCMV Infected DC Lose Responsiveness to Maturation Stimuli

Given that MCMV infection interfered with phenotypic activation of DC it was important to determine whether post-infection with MCMV DC remain responsive to activation by other stimuli. MCMV-infected D1 stimulated with LPS for 48 h on days 2 or 4 post-infection, did not respond to the activation stimulus and no increase was observed in the expression of co-stimulatory molecules (FIG. 12).

MCMV Infected DC Exhibit Altered Cytokine Profiles

To determine whether the phenotypic changes observed in DC post-infection with MCMV affect their function, we examined whether there was a functional correlation with cytokine production. D1 cells secreted IL-12 in response to activation stimuli, such as LPS treatment (FIG. 13a). However, D1 cells infected with MCMV exhibited a reduced capacity to secrete IL-12 by days 2 and 4 post-infection (FIG. 13a). The same was true of DC isolated from the spleens of mice infected with MCMV for 2 or 4 days (FIG. 13b).

In keeping with the up-regulation observed early after infection, splenic DC were found to secrete some IL-12 when harvested from MCMV-infected mice a day 1 post-infection, but levels were absent in DC harvested at days 2 or 4 post-infection.

We have recently shown that post-activation induced by bacterial stimuli DC secrete IL-226. The ability of DC to secrete IL-2 was tested by stimulating D1 cells infected with MCMV with LPS for various periods of time. D1 cells infected with MCMV showed a marked reduction in their ability to secrete IL-2 (FIG. 13c). Similarly, following LPS stimulation, IL-2 was secreted by splenic DC isolated from untreated mice, but not by DC isolated from MCMV-infected animals (FIG. 13d).

MCMV-Infected DC are not Capable of Priming Naive Allogeneic T Cells

The ability of MCMV-infected DC to stimulate the proliferation of naïe allogeneic T cells was assessed in vitro using D1 cells (FIGS. 14a and b) or purified DC (FIG. 14c). LPS-activated D1 cells were the most efficient stimulators of allogeneic T cells at both 2 and 4 days post-treatment inducing 5-10 fold more proliferation than syngeneic controls (FIGS. 14a and b).

As previously described, immature D1 cells were less efficient at priming a T cell response (FIGS. 14a and b). At day 2 post-infection, MCMV-infected D1 induced T cell proliferation to levels similar to those observed following culture with immature D1 cells and syngeneic controls (FIG. 14a). At 4 days post-infection, co-culture of allogeneic T cells with MCMV-infected D1 cells resulted in proliferation levels equivalent to those observed following syngeneic culture (FIG. 14b). Interference with priming naïve allo-reactive T cells was also observed when DC, purified from the spleens of MCMV-infected mice at 4 days post-infection, were compared to DC purified from spleens of uninfected control animals (FIG. 14c).

Discussion

One striking feature of CMV infection is the transient, but severe immunodeficiency that characterizes the initial stages of the infection process. Although transient, lasting from a few weeks to a few months, the CMV-associated immune deficiency has important bearing on host survival. In individuals undergoing transplant surgery, this viral induced suppression can indeed be beneficial, and it has been shown to be associated with a decrease in transplant rejection. Often however, CMV-induced immunosuppression leads to an unfavorable clinical outcome due to the increased incidence of secondary opportunistic infections. A better understanding of CMV-induced immunosuppression is therefore an important consideration in the design of improved viral therapies.

Further importance in understanding the mechanisms leading to CMV-induced immunosuppression arises from the recent interest in using viruses, including CMV, as vectors for gene therapy or vaccine delivery. Unlike measles and HIV, the other two human pathogens known to induce immunosuppression, very little is known about the mechanisms that underlie the immunosuppression that occurs during CMV infection.

In our studies we observed that infection of D1 cultures with MCMV resulted in production of viral progeny. Although the kinetics were slower than those observed post-infection of fibroblast cultures, titers of infectious virus eventually reached levels exceeding those observed in MEF. When mature, or purified DC, were infected we observed a decrease in viral progeny production and a further increase in the length of time before infectious virus was detected. Although the exact reasons for the retarded kinetics observed following infection of DC, as compared to fibroblasts, are unknown, it is possible that this occurs because, unlike MEF, DC cultures are not synchronized in $G_0$ when infected. Importantly, the comparison of viral growth kinetics in immature and mature DC, suggests that MCMV preferentially infects and replicates in immature DC as compared to activated, mature DC. Preferential infection of immature DC may provide the virus with the opportunity to interfere with subsequent activation of these cells (see below).

Having shown that DC can be infected in vitro and having confirmed our findings in the context of an in vivo infection using a recombinant MCMV carrying a LacZ reporter, we addressed the possibility that MCMV may phenotypically and functionally impair DC. We showed that following MCMV infection the fluid-phase endocytic capacity of DC was impaired. These data suggest that infected DC lose their capacity to capture antigen, a property of immature DC and in this respect they exhibit a functional phenotype similar to that observed following LPS stimulation and typical of mature DC.

To further understand the relevance of MCMV infection with respect to DC function, the regulation of cell surface proteins involved in induction of immune responses was examined. After a transient increase in the expression of MHC-I/II, CD40, CD54 and CD86, infected DC exhibited a decreased expression of all the above cell surface antigens, as well as CD80. The initial activation observed following infection of D1 cells in vitro could not be tested using ex vivo purified splenic DC as these cells become activated during the process of tissue digestion and sorting. However, as for D1 cultures, a decrease in the expression of MHC-I/II, CD40, CD54, CD80 and CD86 was observed after MCMV infection of ex vivo purified splenic DC.

The phenomenon of CMV induced down-regulation of MHC-I and II has been well documented in fibroblasts and macrophages, the latter escaping MHC-I down-regulation. The data presented here provide the first evidence for MCMV mediated down-regulation of MHC-I/II, CD40, CD54, CD80 and CD86 expression in DC. Significantly, infection of macrophages was shown to have no effect on surface expression of CD86, yet we have observed a significant reduction in CD86 expression following infection of DC.

Recently it has been shown that DC selectively accumulate MHC-II and CD86 into specialized vesicular carriers prior to delivery to the plasma membrane. The observed down-regulation of MHC-II and CD86 that follows MCMV infection may result from MCMV interference with release from these vesicular carriers and/or enhanced internalization.

The consequences of down-regulation of MHC molecules may be both beneficial and detrimental for MCMV. A loss of MHC-I would interfere with the subsequent activation of virus-specific CTL, however it would also render infected DC more susceptible to NK cell mediated lysis. Previous studies have shown that CD80 acts as a triggering signal for NK cell mediated cytolysis over-riding the protective effects of MHC class I. MCMV infection prevents the up-regulation of CD80 (FIGS. 3, 4 and 5) and results in surface expression of gpm144, a viral protein known to interfere with NK cell mediated lysis.

Consistent with the phenotypic changes, altered cytokine profiles were observed at different times post-MCMV infection. At early times we observed an increase in IL-12 production which quickly disappeared, so that very little IL-12 was produced by day 4 post-infection.

We have shown in Example 1 that IL-2 is secreted by DC which have encountered bacteria. The ability to secrete IL-2 is crucial for the activation of T cell responses. In this report we have shown that post-infection with MCMV, DC lose their ability to secrete IL-2 in response to bacterial stimulation. Several studies have reported a defect in IL-2 synthesis following CMV infection, and have associated this defect with the development of the T cell anergy that characterizes the early stages of CMV infection.

Interestingly, IL-2 therapy has been shown to correct some of the impaired T cell responses associated with CMV infection. Indeed, IL-2 immunotherapy in vivo has been shown to enhance the anti-viral effects of CD8$^+$ CTL resulting in improved control of viral replication. Despite the CMV associated T cell anergy having been the focus of numerous studies, and in spite of the described effects of IL-2, the relevant cellular effecters remain uncharacterized. Indeed, the cells responsible for the IL-2 defect that often accompanies the CMV-associated immunosuppression, have been the subject of some controversy. Interestingly, CMV infection of monocytes has been shown to play a central role in the subsequent immunosuppression. Here, for the first time, we provide evidence that MCMV interferes with the ability of DC to release IL-2 and ultimately impairs the capacity of DC to prime T cell responses.

On the basis of the observed effects of MCMV infection on DC phenotype, it was expected that infected DC would be efficient at priming T cell activation at 2 days pi, when they appear to have a "mature" DC phenotype. This was not the case, and when these DC were tested in an allogeneic MLR, they were found to be very inefficient at stimulating T cell proliferation. Based on the knowledge that the ability of DC to produce IL-2 is already affected at this time post-infection, the observed inability of MCMV-infected DC to prime T cell responsiveness when they appear "phenotypically activated" is likely to result from the MCMV-mediated interference with IL-2 secretion. At 4 days pi, when the infected DC exhibit an "immature" phenotype, their ability to prime T cell proliferation decreased further.

The impaired capacity to prime T cell responses was confirmed when vDC, purified from the spleens of infected mice, were tested. Preliminary data suggest that, in addition to the inability of DC to prime T cells, apoptosis is occurring in the T cell population.

Further evidence of the immunosuppressive effects of MCMV infection on DC functionality came from our findings that post-infection DC lost the ability to respond to bacterial stimuli. Phenotypically no increase in MHC or co-stimulatory markers was observed post-LPS stimulation of infected DC and, as discussed above, the ability to produce cytokines, including IL-12 and IL-2 was impaired. These results may provide an explanation for the increased incidence of opportunistic infections that often accompanies infection with this virus in immunosuppressed individuals.

In this report we have shown that, following MCMV infection, DC exhibited a mixed phenotype of impaired endocytic capacity, an almost complete absence of surface MHC and co-stimulatory molecules and an impaired capacity to fully prime T cells. By targeting dendritic cells and interfering with their functionality, MCMV has been capable of converting the professional initiators of immunity to "novices" incapable of transducing the "danger" signals required to initiate antiviral immune responses. A targeted interference with IL-2 secretion, followed by down-regulation of stimulatory (signal 1—MHC-I/II) and costimulatory (signal 2—CD80, CD86 etc) molecules, resulting in a complete absence of T cell activation, prevents infected DC from executing their tasks and indeed may allow them to contribute to immunosuppression and permit viral persistence. In conclusion, we have demonstrated for the first time that MCMV infection of DC represents a mechanism of viral induced immunosuppression and that the ability of MCMV to interfere with DC-mediated IL-2 secretion maybe of crucial importance.

Example 4

Transcriptional Reprogramming of Dendritic Cells by Differentiation Stimuli

Immature and mature dendritic cells (DC) have been well characterized functionally and phenotypically. Microorganisms or bacterial products such as lipopolysaceharide (LPS) and inflammatory molecules, including tumor necrosis factor (TNF-α), are both believed to activate the DC maturation program which allows DC to initiate and amplify innate and adaptive immune responses. However, there is increasing evidence that the functional state of DC, induced by different stimuli, may be relevant for the immune response outcome. Thus, we compared the transcriptional program of mature, transitional and immature DC, after either LPS or TNF-α stimulation. GENECHIP® (i.e., DNA microarray) oligonucleotide microarrays, representing approximately 6,500 murine genes and ESTs, were used for this analysis. A very diverse modulation of gene expression was observed with the two stimuli. Only LPS-treated cells showed a pattern of expression of genes compatible with a definitive growth arrest and with a suitable activation and control of the immune response.

Materials and Methods

Cells and reagents. The D1 cells were derived from murine splenic DC and maintained in vitro in IMDM supplemented with 30% R1 conditional medium as previously described. LPS (*Escherichia coli* sero- type 026:B6) was purchased from Sigma Chemical Co. and used at 10 µg/ml. Muriner TNF-α (Genetech Inc., San Francisco. Calif.) was used at 100 U/ml. Cells were grown and harvested at the same time.

RNA extraction, amplification and labeling for hybridization. Antisense cRNA was prepared following Affymetrix (Santa Clara, Calif.) recommendations. Briefly, mRNA was directly extracted from frozen pellets using the DIRECT OLIGOTEX KIT (i.e., column chromatography kit for mRNA purification) from Qiagen (Chatsworth, Calif.) and converted to double-stranded cDNA using a modified oligo dT primer with a 5'T7 RNA polymerase promoter sequence and the SUPER-SCRIPT CHOICE SYSTEM (i.e., reverse transcriptase system) for cDNA synthesis (Life Technologies, Gaithesbourg, Md.). Double-stranded cDNA (0.5 µg) was transcribed to cRNA with the T7 RNA polymerase (T7 MEGASCRIPT KIT (i.e., phage specific in vitro transcription kit); Ambion, Austin, Tex.) in the presence of a mixture of unlabeled ATP, CTP, GTP, UTP and biotin-labeled CTP and UTP (ENZO Diagnostics, Farmingdale, N.Y.). cRNA was purified on an affinity column (RNEASY (i.e., a RNA purification column); Qiagen).

Probe array hybridization and scanning. The Mu6500 GENECHIP (i.e., DNA microarray) array consists of a set of four individual chips, A-D, collectively representing 6,500 murine genes and ESTs. Analysis of the D1 samples was performed by hybridizing the cRNA to the GENECHIP (i.e., DNA microarray) arrays A-D. Probe array hybridizations were carried out as described. cRNA was fragmented to an average size of 50-200 bases, by incubation for 30 min at 94° C. in 40 mM Tris-acetate pH 8.1, 100 mM potassium acetate and 30 mM magnesium acetate.

Samples were then diluted in the hybridization solution (1 M NaCI, 10 mM Tris pH7.6, 0.005% Triton X-100, 0.1 mg/ml herring sperm DNA, BioB-, BioC-, BioD-, cre- control cRNA at a concentration of 1.5, 5, 25, 100 pM, respectively) at a final concentration of 0.05 µg/ml heated at 94° C. for 5 min and placed in the hybridization cartridge (200 µl/chip). Hybridizations were performed at 40° C. for 16 h. Following hybridization the chips were rinsed with 6× SSPE-T (0.9 M NaCI, 60 mM $NaH_2PO_4$, 6 mM EDTA, 0.005% Triton X-100 adjusted to pH 7.6) and 0.5× SSPE-T and stained by incubating with 2 µg/ml streptavidin-phycoerythrin (Molecular Probes, Eugene, Oreg.) and 1 mg/ml acetylated BSA (Sigma, St. Louis, Mo.).

The arrays were read at a resolution of 7.5 µm. using a confocal scanner (Affymetrix) and analyzed with the GENE-CHIP 3.3 GENE EXPRESSION ANALYSIS PROGRAM (i.e., gene expression analysis software) (Affymetrix). Genes, that showed, in two independent experiments, a fold change of at least 2 in stimulated cells over the baseline were considered differentially expressed.

ELISA. IL-1β, IL-12p40 and IL-6 were quantified using DUOSET ELISA DEVELOPMENT SYSTEM (i.e., enzyme linked immunosorbant assay system) (R&D Systems, Minneapolis, Minn.).

Genomic-Scale Gene Expression Analysis

To investigate the differential effects of TNF-α versus LPS on DC priming we have used the Affymetrix GENE-CHIP (i.e., DNA microarray) technology, that permits the simultaneous analysis of the expression of thousands of genes. These analyses require homogeneous cell populations to avoid dilution and contamination of information. Bone marrow-derived mouse DC are extremely unstable and it is not possible to obtain homogeneous immature DC without contamination with mature and intermediate DC. Cell lines that closely parallel fresh DC functions are a valid alternative. Thus we took advantage of the previously described mouse DC line, D1. D1 cells are a splenic, myeloid and growth factor-dependent DC line that can be maintained indefinitely in culture in the immature state. This cell line can be driven to full maturation using different stimuli. In particular, D1 cells reach a mature state 18 h after LPS or TNF-α stimulation, as assessed by phenotypical (up-regulation of class II and costimulatory molecules) and functional characteristics, like antigen presentation, inhibition of migration, block of antigen uptake, cytoskeleton rearrangements.

Gene expression analysis was performed on immature, transitional (6 h LPS and TNF-α-activated) and mature (18 h LPS- and TNF-α-activated) D1 cells using GENECHIP (i.e., DNA microarray) oligonucleotide probe arrays representing approximately 6,500 distinct mouse genes and ESTs. The 6,500 probe sets are subdivided in four individual chips, A-D, each containing oligonucleotide probes for about 1,600 genes and ESTs. The hybridized arrays were analyzed using the GENECHIP 3.3 GENE EXPRESSION ANALYSIS PROGRAM (i.e., gene expression analysis software). Data analysis protocols, sensitivity and quantitative aspects of the method have been previously precisely described. In brief, gene probes are represented by 20 perfectly matched 20-mer oligonucleotides (PM) and 20 control oligonucleotides with a single mismatch (MM). Gene expression levels are defined averaging the differences (AvgDiff) between the PM and MM of every probe pair over the entire probe set:

$$AvgDiff = \frac{\Sigma(PM - MM)}{n \text{ of pairs}}$$

An AvgDiff of 20 approximates the lower value of fluorescence intensity for detected genes. An absolute (individual) analysis of each probe array was performed to determine gene expression levels in each target cRNA analyzed. Signal intensities were then normalized among hybridized arrays by measuring the average value of signal intensities for each chiparray and scaling to a fixed arbitrary value (target intensity). We used a target intensity of 100, calculated considering average values of signal intensities for mouse GENECHIPS (i.e., DNA Microarrays). This particular procedure has been developed in order to minimize the variability of GENECHIP (i.e., DNA microarray) performance and sample preparation.

Subsequently, probe arrays hybridized with TNF-α- and LPS-activated D1 cell samples were compared to the same baseline sample (non-stimulated cells) to determine differences in expression levels between treated and untreated cells. Among the genes and ESTs displayed on the chip 25% were called present in non-stimulated and 6 h and 18 h LPS- and TNF-α-activated DC. Hybridization efficiency was assessed for each array by measuring the signal intensities of the three control bacteria BioB, BioC, BioD and one phage cre gene cRNA (see Sect. 4). BioB "spikes" at 1.5 pM were usually detected. Thus, under these hybridization conditions the detection limit was around 1.5 pM.

Genes modulated in treated cells with respect to untreated cells were divided into four main groups: induced (not detected in non-activated but detected in activated cells), up-regulated, down-regulated, suppressed (detected in non-activated and not detected in activated cells). For up-regulated and down-regulated genes we have considered only those ones that showed at least a twofold change in the level of mRNA expression in two independent experiments (fold change≧2; FIG. 15).

Differences in expression are calculated by dividing the intensity values (AvgDiff) of genes from treated cells by intensity values of genes from non-stimulated cells. Since not-detected genes do not have reliable intensity values, we could not use the fold change as a parameter for the expression analysis of induced and suppressed genes. Thus, the former were selected on the basis of the level of expression reached after stimulation (a minimum AvgDiff of 40 in two independent experiments), and the latter on the basis of the level of expression they had in unstimulated cells (a minimum AvgDiff of 40, suppressed in two independent experiments) (FIG. 15).

Although LPS and TNF-α were considered equivalent factors for DC maturation, D1 cells activated with these two different stimuli showed a very diverse gene expression program (FIG. 15). In Table 2 we have listed an example of the gene families differentially expressed or modulated in mature DC compared to non-stimulated cells.

TABLE 2

Differential gene expression analysis in LPS- and TNF-α-stimulated versus unstimulated D1 cells
Table 1. Differential gene expression analysis in LPS- and TNF-α-stimulated versus unstimulated D1 cells

| ID[1] | Gene name | LPS 6 h | LPS 18 h | TNFα 6 h | TNFα 18 h |
|---|---|---|---|---|---|
| Cell surface and membrane proteins | | | | | |
| L09754 | CD30L | NC | NC | I 36* | I 42* |
| U12763 | OX40L | NC | I 70 | NC | NC |
| M833312 | CD40 | I 345* | I 201* | NC | I 4.3* |
| M34510 | CD14 | U 11.6 | U 3.2 | NC | NC |
| Y08026 | 1AP3 | S 73** | S 73** | NC | S 73** |
| U10484 | Jaw1 | S 242** | S 242** | NC | D 2.6 |
| X93328 | F4-80 | D 2.6 | D 2.4 | NC | NC |
| Z16078 | CD53 | D 3.9 | D 7.3 | D 2 | D 2.3 |
| X68273 | Macrostatin | D 2.3 | D 2.1 | NC | NC |
| U47737 | TSA1 | D 4.1 | D 9.9 | NC | NC |
| U18372 | CD37 | D 3.5 | D 2.9 | NC | NC |
| U05265 | gp49 | NC | D 4.9 | D 2.9 | D 3.7 |
| L08115 | CD9 | NC | D 4.3 | D 2.9 | D 2.4 |
| X72910 | HSA-C | NC | D 5.5 | D 2.8 | D 2.5 |
| U25633 | TMP | S 165** | S 165** | NC | D 7.4 |
| Cell cycle and apoptosis | | | | | |
| D86344 | TIS | NC | I 273* | NC | NC |
| L49433 | c-1AP-I | I 71* | I 68* | NC | I 77* |
| L16846 | BTG1 | U 3.2 | D 2.4 | NC | NC |
| M83749 | cyclin D2 | U 3.7 | U 3.7 | NC | NC |
| U19860 | GAS | NC | U 2.8 | NC | NC |
| D50494 | RCK | U 3 | U 2.2 | NC | NC |
| M64403 | CYL-1 | D 2.4 | D 3.8 | NC | NC |
| U70210 | TR2L | NC | NC | D 2.4 | D 3.5 |
| U58633 | p34CDC2 | NC | D 5.5 | D 2.2 | D 3.2 |
| X82786 | Ki-67 | NC | D 6.4 | NC | D 2.6 |
| Z26580 | cyclin A | NC | S 147** | NC | NC |
| X66032 | cyclin B2 | NC | S 108** | NC | S 108** |
| X64713 | cyclin B1 | NC | S 47** | NC | S 47** |
| D86725 | mMCM2 | NC | S 125** | D 2.7 | NC |
| Z72000 | BTG3 | S 46** | S 46** | NC | S 46** |
| Antigen processing and presentation | | | | | |
| U60329 | PA28 | U 3.2 | U 3.2 | NC | NC |
| X97042 | UBcM4 | U 2.3 | U 2.6 | U 2.2 | U 2.6 |
| M55637 | TAP-1cas | NC | U 2.8 | NC | NC |
| U35323 | H-2Mβ2 | D 12.5 | D 9.2 | D 2.2 | D 2.2 |
| U35323 | H-2Mα | S 304** | S 304** | NC | NC |
| U35323 | H-2Mβ1 | D 6.9 | S 149** | NC | NC |
| D83585 | proteasome Z subunit | NC | NC | D 2.5 | D 2.2 |
| K01923 | I-Aα | D 2.8 | D 3.5 | NC | NC |
| V01527 | I-Aβ | NC | D 3.7 | NC | NC |
| Secreted molecules | | | | | |
| J03783 | IL-6 | I 45* | I 78* | NC | NC |
| M86671 | IL-12p40 | I 820* | I 759* | NC | NC |
| M64404 | IL-IRA | U 13.4 | U 9 | NC | NC |
| X03505 | serum amyloid | NC | I 256* | NC | I 67* |
| M15131 | IL-1β | D 82 | U 34.8 | U 7.4 | U 11.8 |
| M73061 | MIP-1α | D 3.9 | D 5.5 | NC | NC |
| X53798 | MIP-2 | U 20.2 | U 5.7 | NC | NC |
| U02298 | RANTES | U 3.7 | U 28 | U 3 | U 3.4 |
| X58861 | C1qα | S 628** | S 628** | NC | NC |
| X66295 | C1qC | D 15 | S 656** | D 3.7 | D 3.5 |
| X16151 | EtAI | S 485** | S 485** | NC | D 7.9 |
| M19681 | JE | D 5.9 | S 348 | D 6 | D 4.6 |
| X06086 | MEP | D 2.6 | D 2.9 | D 2 | S 126** |
| U50712 | MCP5 | S 83** | S 83** | S 83** | S 83** ⊕ |
| X83601 | PTX3 | D 3.8 | S 211** | D 3.6 | S 211** |
| M22531 | C1qB | D 8.7 | D 42.8 | D 2.4 | D 4.2 |
| M58004 | C10 | D 3.1 | D 6.5 | D 2.6 | D 5.2 |
| L19932 | βig-h3 | NC | D 5.1 | NC | NC |
| X12905 | properdin | D 4.7 | D 16.2 | D 2.2 | NC |

[1], accession number;
NC: No change in the level of expression;
I: induced (detected only in stimulated cells);
U: up-regulated;
D: down-regulated;
S: suppressed (detected only in unstimulated cells),
*AvgDiff reached after stimulation,
**AvgDiff in the baseline, values without asterisks represent the fold change in stimulated versuses unstimulated cells.

Genes Involved in Cell Cycle Control and Survival

Termination differentiation results in the growth arrest of proliferating cells. There are evidences that the cell cycle control in immature, splenic, mouse DC is not stringently regulated and small increase in cell number can be observed when they are plated over an irradiated stromal cell monolayer of fibroblasts and endothelial cells. Mature DC completely loose the proliferation capacity and die by apoptosis 8-9 days after activation.

A very similar differentiation process can also be induced in immature D1 cells that undergo growth arrest and terminal differentiation in vitro. An important difference between LPS- and TNF-α-activated D1 cells resided in the complexity of the pattern of genes involved in the control of cell cycle progression (Table 2). Cyclins are usually expressed during mitogenesis and they control cell proliferation. Cyclins A and B are involved in the control of G1/S and G2/M transition, respectively. LPS induced the suppression of type A and B cyclins, including genes like MCM2, which allow the initiation of DNA replication.

In contrast, TNF-α-activated D1 cells, showed exclusive suppression of cyclins necessary to pass the G2 phase (cyclin B1, cyclin B2), suggesting that they can still initiate DNA replication and that they could be arrested at a cell cycle checkpoint between S and G2. D-type cyclins have a different pattern of expression with respect to the other type of cyclins. They are induced in many different cell types by mitogens and are essential for G1 phase progression, but they have also been described to be induced by differentiation stimuli in megakariocytes facilitating their differentiation process. Moreover, cyclin D2 is induced in macrophages following the anti-mitogenic stimulus of LPS. Interestingly LPS but not TNF-α induces the up-regulation of D type cycling (Table 1). In addition, anti-proliferative genes, such as BTG1, GAS, RCK were exclusively up-regulated in LPS-activated D1 cells (Table 2).

This particular pattern of expression could suggest that only LPS was able to induce a definitive DC growth arrest. LPS-activated DC underwent irreversible growth arrest already 24 h after stimulation, whereas TNF-α-activated D1 cells showed only a strong proliferation slow down but not a definitive growth arrest (FIG. 16), with a doubling time of 130 h. These results imply that only LPS drives complete terminal differentiation of DC and that TNF-α induces only partial DC activation.

As is consistent with the observation that LPS is able to promote both DC maturation and survival of terminally differentiated DC, LPS-activated D1 cells also expressed anti-apoptotic genes, at late time points, such as TIS (topoisomerase-inhibitor suppressed). Moreover, mRNA coding for the c-IAP-1 protein (required together with TRAF-1 (up-regulated) and TRAF-2 (expressed) to inhibit TNF-α-induced apoptotic cell death) was observed in both TNF-α- and LPS- activated D1 cells.

Genes Involved in Antigen Processing and Peptide Loading on MHC Molecules

The survival of growth-arrested DC after LPS stimulation would be necessary to allow mature DC to migrate into lymphoid tissues and prime naive CDB+ and CD4+ T cells. To accomplish this task, DC should magnify their capacity to produce peptides from native protein antigens to be loaded on MHC class I and class II molecules. Interestingly, genes involved in the antigen presentation function showed a distinctive pattern of expression in LPS or TNF-α-activated D1 cells.

Only LPS up-regulated the PA2B proteasome activator and the TAP-1 molecule mRNA (Table 2). The PA2B protein dramatically increases the spectrum of peptides produced and the efficiency of the 20S proteasome, whereas the TAP-1 molecule is required to transfer proteasome-produced peptides from the cytosol to the endoplasmic reticulum. The proteasome activator was up-regulated already at 6 h after LPS activation, while TAP-1 up-regulation was measurable only at late time points.

This pattern of mRNA upregulation in D1 cells after LPS stimulation correlates well with the kinetic of MHC class I new biosynthesis in D1 cells, which peaks at 18 h after bacteria or LPS stimulation. In addition, LPS is more efficient than TNF-α in inducing the up-regulation of MHC class I molecules and the stability of peptide-MHC complex expression at the surface of DC can be extended from 24 to 72 h when DC are pretreated with LPS but not TNF-α. Thus, LPS-stimulation induces a remarkable activation of the entire intracellular apparatus necessary for class I antigen presentation function. We did not observe any class I mRNA up-regulation with the GENECHIP (i.e., DNA microarray) analysis. In fact, the class I oligonucleotide probes are specific for the H-2D molecule and the surface class I up-regulation observed in D1 cells, 18 h after challenge, was relative to the H-2K protein.

Concerning MHC class II genes, we have previously shown that the up-regulation of class II protein synthesis is very rapid, peaking as early as 1 h after DC activation and this is followed by a striking down-regulation. The GENECHIP (i.e., DNA microarray) approach validated the previous analysis of MHC protein expression during DC maturation, showing that class II molecule mRNA were down-regulated in LPS-stimulated D1 cells. Class II molecule mRNA are also down-regulated in LPS-stimulated human DC. Moreover, in agreement with the increased stability observed in peptide-MHC class II complexes in activated DC, the H-2M molecules, which regulate MHC class II loading with antigenic peptides, were either down-regulated or suppressed and, again, the level of down-regulation was more pronounced in LPS-treated compared to TNF-α-stimulated D1 cells. The down- regulation was already evident 6 h after LPS stimulation (Table 2).

This gene expression pattern implicates that LPS is more effective than TNF-α in inducing the reprogramming of presentation activity typical for mature DC. Taken as a whole, these data indicate that LPS but not TNF-α is sufficient to drive DC toward a stage of maturation appropriate for the immune response activation. Our observations are also supported by the finding that TNF-α-activated DC are, actually, rather inefficient in activating T cells in MLR assays in vitro and in conferring tumor protection in mouse models in vivo. This is also supported by the strong up-regulation of the mRNA coding for the well known leukocyte chemo-attractants RAN-TES, MIP1α and MIP2, in LPS-activated but not in TNF-α-treated D1 cells (Table 2).

A similar pattern of chemokines up-regulation at early and late time points after LPS stimulation has been also observed using RNase protection and chemotactic assays. Furthermore, LPS-but not TNF-α-stimulated D1 cells expressed interleukin (IL)-6 (Table 2 and FIG. 17). This cytokine is known to be involved in increasing the spectrum of peptides presented by DC, in leukocyte recruitment and in B cell differentiation.

Gene Involved in The Control of Inflammatory Responses

A physiological immune response originates from a well-controlled inflammatory response. Genes involved in activating and controlling the inflammation process are differentially regulated in DC matured in the presence of the two different stimuli (Table 2). In LPS-matured DC and in much lesser extent in TNF-α-treated cells is observed suppression or strong down-regulation of the complement molecule C1q (Table 2).

This protein is known to play a role in inflammatory responses by increasing phagocytic activity and microbial killing of macrophages and neutrophils, by enhancing B cell secretion of immunoglobulins and by inducing the expression of adhesion molecules on platelets. In addition the C1q molecule has been described as being the basis for fibroblast attachment and growth at sites of chronic inflammation. Recently a strong inflammatory role in the central nervous system has been attributed to C1q. Thus, the down-regulation of C1q transcription at late time points may be a way of controlling inflammatory processes.

Numerous in vivo studies indicate that the balance between IL-1 and IL-1RA is important in influencing the response to pathogens. A definite anti-inflammatory role has, indeed, been attributed to the IL-1RA molecule that has an important function in limiting organ damage subsequent to the host response to infection. In LPS-matured D1 a strong up-regulation of IL-1β together with IL-1 receptor antagonist (IL-1RA) mRNA expression is observed, both at early and late time points. Whereas in TNF-α-stimulated D1 cells only little IL-1β production and not IL-1RA expression is observed (Table 2). Thus, LPS-matured DC are likely to have an important role not only in stimulating but also in controlling the inflammatory response.

Another cytokine differentially expressed in LPS- activated compared to TNF-a-treated 01 cells is IL-12p40 (Table 2, FIG. 17). The IL-12p40 homodimer is an IL-12p75 antagonist in vitro and it acts as a potent immune-suppressant of Th1 response in vivo. It has been shown to induce a deviation of pancreas infiltrating CD4$^+$ T cells to the Th2 phenotype in NOD mice as well as to reduce the onset of spontaneous diabetes.

Together, the above data show clear differences in DC activation induced by distinct stimuli. TNF-α comes out as a mild alert stimulus unable to drive DC to terminal differentiation. The relevance of the stimuli used to induce DC maturation should be taken into account for DC-based therapies, since it is likely that the quality of activation may affect the final outcome of the clinical response.

Microarray approach allows quantitative and simultaneous analysis of gene expression of a large amount of genes. Many cellular processes are regulated by changes in mRNA levels. Thus systematic studies of gene expression patterns have proven to be extremely useful for studying cellular effects of natural stimuli and to be a powerful tool to identify molecular events and key pathways involved in specific cellular functions.

Although the invention has been described with reference to the presently preferred embodiment, it should be understood that various modifications can be made without departing from the spirit of the invention. Accordingly, the invention is limited only by the following claims.

What is claimed is:

1. A method of screening a compound for an effect on perturbation induced dendritic cell IL-2 production comprising: perturbing an immature dendritic cell (DC) by exposing the DC to a bacterial or yeast stimulus; incubating a compound with the perturbed DC; and detecting the effect of the compound on perturbation induced IL-2 expression in the DC, wherein an increase in the amount of perturbation induced IL-2 expression in the presence of the compound is indicative of stimulating perturbation induced dendritic cell IL-2 production and a decrease in the amount of perturbation induced IL-2 expression in the presence of the compound is indicative of inhibiting perturbation induced dendritic cell IL-2 production.

2. The method of claim 1, wherein the compound is a small molecule.

3. The method of claim 1, wherein the immature dendritic cell is a D1 cell, and wherein the cell is a growth factor dependent long term murine derived splenic cell.

4. The method of claim 1, wherein the yeast stimulation comprises contacting the dendritic cell with zymosan.

5. The method of claim 1, further comprising determining IL-2 expression by enzyme-linked immunosorbent assay (ELISA).

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial sequence
<220> FEATURE:
<223> OTHER INFORMATION: PCR primer

<400> SEQUENCE: 1
tcctcacagt gacctcaagt cc                                            22

<210> SEQ ID NO 2
<211> LENGTH: 22
<212> TYPE: DNA
<213> ORGANISM: Artificial sequence
<220> FEATURE:
<223> OTHER INFORMATION: PCR primer

<400> SEQUENCE: 2
tgacagaagg ctatccatct cc                                            22

<210> SEQ ID NO 3
<211> LENGTH: 22
<212> TYPE: DNA
<213> ORGANISM: Artificial sequence
<220> FEATURE:
<223> OTHER INFORMATION: PCR primer

<400> SEQUENCE: 3
catcgtgggc cgctctaggc ac                                            22

<210> SEQ ID NO 4
<211> LENGTH: 22
<212> TYPE: DNA
<213> ORGANISM: Artificial sequence
<220> FEATURE:
<223> OTHER INFORMATION: PCR primer

<400> SEQUENCE: 4
ccggccagcc aagtccagac gc                                            22

<210> SEQ ID NO 5
<211> LENGTH: 20
<212> TYPE: DNA
<213> ORGANISM: Artificial sequence
```

-continued

```
<220> FEATURE:
<223> OTHER INFORMATION: Oligo DNA containing the unmethylated CpG motif

<400> SEQUENCE: 5
tccatgacgt tcctgatgct                                                    20

<210> SEQ ID NO 6
<211> LENGTH: 20
<212> TYPE: DNA
<213> ORGANISM: Artificial sequence
<220> FEATURE:
<223> OTHER INFORMATION: Oligo DNA containing the unmethylated CpG motif

<400> SEQUENCE: 6
tccatgagct tcctgatgct                                                    20
```